US009882592B2

(12) United States Patent
O'Hagan et al.

(10) Patent No.: US 9,882,592 B2
(45) Date of Patent: Jan. 30, 2018

(54) METHOD, APPARATUS, AND COMPUTER PROGRAM PRODUCT FOR TAG AND INDIVIDUAL CORRELATION

(71) Applicant: ZIH Corp., Lincolnshire, IL (US)

(72) Inventors: James J. O'Hagan, Lincolnshire, IL (US); Michael A. Wohl, Lincoln, RI (US)

(73) Assignee: ZIH Corp., Lincolnshire, IL (US)

( * ) Notice: Subject to any disclaimer, the term of this patent is extended or adjusted under 35 U.S.C. 154(b) by 0 days.

(21) Appl. No.: 15/247,413

(22) Filed: Aug. 25, 2016

(65) Prior Publication Data

US 2016/0361595 A1  Dec. 15, 2016

Related U.S. Application Data

(63) Continuation of application No. 13/942,507, filed on Jul. 15, 2013, now abandoned.

(Continued)

(51) Int. Cl.
*H04B 1/10*    (2006.01)
*G06F 17/30*   (2006.01)
(Continued)

(52) U.S. Cl.
CPC ........... *H04B 1/1036* (2013.01); *A41D 1/002* (2013.01); *A41D 1/04* (2013.01); *A42B 3/30* (2013.01);
(Continued)

(58) Field of Classification Search
None
See application file for complete search history.

(56) References Cited

U.S. PATENT DOCUMENTS 3,732,500 A   5/1973  Dishal et al.
4,270,145 A   5/1981  Farina
(Continued)

FOREIGN PATENT DOCUMENTS

EP   1235077 A2   8/2002
EP   1241616 A2   9/2002
(Continued)

OTHER PUBLICATIONS

International Search Report and Written opinion from International Application No. PCT/US2014/040881 dated Nov. 4, 2014.
(Continued)

*Primary Examiner* — Laura Nguyen

(57) ABSTRACT

Provided herein are systems and computer readable media for associating environmental measurements with an individual using a plurality of sensors, a plurality of tags and a plurality of receivers disposed about a monitored area. Various embodiments of the invention include: receiving blink data from receivers positioned about the monitored area, wherein the blink data is generated by at least one tag carried by the individual; determining tag location data based on the blink data, wherein the tag location data comprises a tag location estimate; associating the tag location data with an individual profile; receiving a sensor signal from a sensor comprising environmental measurements associated with the individual; receiving a sensor location associated with the sensor; comparing the tag location estimate to the sensor location; determining a sensor-individual correlator based on the proximity between the tag location estimate and the sensor location; and associating the sensor-individual correlator with the environmental measurements.

21 Claims, 17 Drawing Sheets

Related U.S. Application Data

(60) Provisional application No. 61/831,990, filed on Jun. 6, 2013.

(51) Int. Cl.

| | | |
|---|---|---|
| *H04L 29/08* | (2006.01) | |
| *A63B 24/00* | (2006.01) | |
| *G06K 7/10* | (2006.01) | |
| *G08C 17/02* | (2006.01) | |
| *H04B 1/7097* | (2011.01) | |
| *H04W 4/02* | (2009.01) | |
| *A63B 71/06* | (2006.01) | |
| *G06K 9/00* | (2006.01) | |
| *G06F 19/00* | (2011.01) | |
| *G06N 5/02* | (2006.01) | |
| *H04L 12/26* | (2006.01) | |
| *G06Q 50/20* | (2012.01) | |
| *G09B 19/00* | (2006.01) | |
| *H04B 1/7163* | (2011.01) | |
| *H04B 1/719* | (2011.01) | |
| *G06Q 50/22* | (2012.01) | |
| *H04Q 9/00* | (2006.01) | |
| *A41D 1/00* | (2006.01) | |
| *A41D 1/04* | (2006.01) | |
| *A42B 3/30* | (2006.01) | |
| *G06K 17/00* | (2006.01) | |
| *G06Q 90/00* | (2006.01) | |

(52) U.S. Cl.
CPC ...... *A63B 24/0021* (2013.01); *A63B 24/0062* (2013.01); *A63B 71/06* (2013.01); *A63B 71/0619* (2013.01); *A63B 71/0622* (2013.01); *A63B 71/0686* (2013.01); *G06F 17/3087* (2013.01); *G06F 17/30864* (2013.01); *G06F 17/30876* (2013.01); *G06F 19/3437* (2013.01); *G06K 7/10227* (2013.01); *G06K 7/10297* (2013.01); *G06K 7/10306* (2013.01); *G06K 7/10366* (2013.01); *G06K 9/00342* (2013.01); *G06N 5/02* (2013.01); *G06Q 50/20* (2013.01); *G06Q 50/22* (2013.01); *G08C 17/02* (2013.01); *G09B 19/0038* (2013.01); *H04B 1/7097* (2013.01); *H04B 1/719* (2013.01); *H04B 1/71635* (2013.01); *H04B 1/71637* (2013.01); *H04L 43/04* (2013.01); *H04L 67/12* (2013.01); *H04Q 9/00* (2013.01); *H04W 4/02* (2013.01); *A63B 24/00* (2013.01); *A63B 2024/0025* (2013.01); *A63B 2220/12* (2013.01); *A63B 2220/836* (2013.01); *A63B 2225/50* (2013.01); *A63B 2225/54* (2013.01); *G06K 2017/0045* (2013.01); *G06Q 90/00* (2013.01)

(56) References Cited

U.S. PATENT DOCUMENTS

| | | |
|---|---|---|
| 5,046,133 A | 9/1991 | Watanabe et al. |
| 5,119,104 A | 6/1992 | Heller |
| 5,469,409 A | 11/1995 | Anderson et al. |
| 5,513,854 A | 5/1996 | Daver |
| 5,645,077 A | 7/1997 | Foxlin |
| 5,699,244 A | 12/1997 | Clark et al. |
| 5,901,172 A | 5/1999 | Fontana et al. |
| 5,920,287 A | 7/1999 | Belcher et al. |
| 5,930,741 A | 7/1999 | Kramer |
| 5,995,046 A | 11/1999 | Belcher et al. |
| 6,028,626 A | 2/2000 | Aviv |
| 6,121,926 A | 9/2000 | Belcher et al. |
| 6,176,837 B1 | 1/2001 | Foxlin |
| 6,204,813 B1 | 3/2001 | Wadell et al. |
| 6,366,242 B1 | 4/2002 | Boyd et al. |
| 6,380,894 B1 | 4/2002 | Boyd et al. |
| 6,593,885 B2 | 7/2003 | Wisherd et al. |
| 6,655,582 B2 | 12/2003 | Wohl et al. |
| 6,710,713 B1 | 3/2004 | Russo |
| 6,812,884 B2 | 11/2004 | Richley et al. |
| 6,836,744 B1 | 12/2004 | Asphahani et al. |
| 6,882,315 B2 | 4/2005 | Richley et al. |
| 7,009,638 B2 | 3/2006 | Gruber et al. |
| 7,190,271 B2 | 3/2007 | Boyd et al. |
| 7,263,133 B1 | 8/2007 | Miao |
| 7,667,604 B2 | 2/2010 | Ebert et al. |
| 7,671,802 B2 | 3/2010 | Walsh et al. |
| 7,710,322 B1 | 5/2010 | Ameti et al. |
| 7,739,076 B1 | 6/2010 | Vock et al. |
| 7,755,541 B2 | 7/2010 | Wisherd et al. |
| 7,899,006 B2 | 3/2011 | Boyd |
| 7,969,348 B2 | 6/2011 | Baker et al. |
| 8,009,727 B2 | 8/2011 | Hui et al. |
| 8,023,917 B2 | 9/2011 | Popescu |
| 8,077,981 B2 | 12/2011 | Elangovan et al. |
| 8,269,835 B2 | 9/2012 | Grigsby et al. |
| 8,279,051 B2 | 10/2012 | Khan |
| 8,289,185 B2 | 10/2012 | Alonso |
| 8,457,392 B2 | 6/2013 | Cavallaro et al. |
| 8,477,046 B2 | 7/2013 | Alonso |
| 8,568,278 B2 | 10/2013 | Riley et al. |
| 8,665,152 B1 | 3/2014 | Kling et al. |
| 8,696,458 B2 | 4/2014 | Foxlin et al. |
| 8,705,671 B2 | 4/2014 | Ameti et al. |
| 8,775,916 B2 | 7/2014 | Pulsipher et al. |
| 8,780,204 B2 | 7/2014 | DeAngelis et al. |
| 8,795,045 B2 | 8/2014 | Sorrells et al. |
| 8,842,002 B2 | 9/2014 | Rado |
| 8,989,880 B2 | 3/2015 | Wohl et al. |
| 9,014,830 B2 | 4/2015 | Wohl et al. |
| 9,081,076 B2 | 7/2015 | DeAngelis et al. |
| 9,185,361 B2 | 11/2015 | Curry et al. |
| 9,381,645 B1 | 7/2016 | Yarlagadda et al. |
| 2001/0010541 A1 | 8/2001 | Fernandez et al. |
| 2001/0030625 A1 | 10/2001 | Doles et al. |
| 2002/0004398 A1 | 1/2002 | Ogino et al. |
| 2002/0041284 A1 | 4/2002 | Konishi et al. |
| 2002/0114493 A1 | 8/2002 | McNitt et al. |
| 2002/0116147 A1 | 8/2002 | Vock et al. |
| 2002/0130835 A1 | 9/2002 | Brosnan |
| 2002/0135479 A1 | 9/2002 | Belcher et al. |
| 2003/0090387 A1 | 5/2003 | Lestienne et al. |
| 2003/0095186 A1 | 5/2003 | Aman et al. |
| 2003/0128100 A1 | 7/2003 | Burkhardt et al. |
| 2003/0163287 A1 | 8/2003 | Vock et al. |
| 2003/0227453 A1 | 12/2003 | Beier et al. |
| 2004/0022227 A1 | 2/2004 | Lynch et al. |
| 2004/0062216 A1 | 4/2004 | Nicholls et al. |
| 2004/0108954 A1 | 6/2004 | Richley et al. |
| 2004/0178960 A1 | 9/2004 | Sun |
| 2004/0189521 A1 | 9/2004 | Smith et al. |
| 2004/0249969 A1 | 12/2004 | Price |
| 2004/0260470 A1 | 12/2004 | Rast |
| 2004/0260828 A1 | 12/2004 | Price |
| 2005/0026563 A1 | 2/2005 | Leeper et al. |
| 2005/0031043 A1 | 2/2005 | Paquelet |
| 2005/0059998 A1 | 3/2005 | Norte et al. |
| 2005/0073418 A1 | 4/2005 | Kelliher et al. |
| 2005/0075079 A1 | 4/2005 | Jei et al. |
| 2005/0093976 A1 | 5/2005 | Valleriano |
| 2005/0148281 A1 | 7/2005 | Sanchez-Castro et al. |
| 2005/0207617 A1 | 9/2005 | Sarnoff |
| 2006/0067324 A1 | 3/2006 | Kim |
| 2006/0139167 A1 | 6/2006 | Davie et al. |
| 2006/0164213 A1 | 7/2006 | Burghard et al. |
| 2006/0252476 A1 | 11/2006 | Bahou |
| 2006/0264730 A1 | 11/2006 | Stivoric et al. |
| 2006/0271912 A1 | 11/2006 | Mickle et al. |
| 2006/0281061 A1 | 12/2006 | Hightower et al. |
| 2007/0091292 A1 | 4/2007 | Cho et al. |
| 2007/0176749 A1 | 8/2007 | Boyd et al. |
| 2007/0296723 A1 | 12/2007 | Williams |

(56) References Cited

U.S. PATENT DOCUMENTS

| | | |
|---|---|---|
| 2008/0065684 A1 | 3/2008 | Zilberman |
| 2008/0106381 A1 | 5/2008 | Adamec et al. |
| 2008/0113787 A1 | 5/2008 | Alderucci |
| 2008/0129825 A1 | 6/2008 | DeAngelis et al. |
| 2008/0140233 A1 | 6/2008 | Seacat |
| 2008/0186231 A1 | 8/2008 | Aljadeff et al. |
| 2008/0204248 A1 | 8/2008 | Winget et al. |
| 2008/0224866 A1* | 9/2008 | Rehman ............. G08B 13/2417 340/572.1 |
| 2008/0262885 A1 | 10/2008 | Jain et al. |
| 2008/0266131 A1 | 10/2008 | Richardson et al. |
| 2008/0269016 A1 | 10/2008 | Ungari et al. |
| 2008/0281443 A1 | 11/2008 | Rogers |
| 2008/0285805 A1 | 11/2008 | Luinge et al. |
| 2008/0291024 A1 | 11/2008 | Zhang et al. |
| 2009/0048044 A1 | 2/2009 | Oleson et al. |
| 2009/0141736 A1 | 6/2009 | Becker |
| 2009/0231198 A1 | 9/2009 | Walsh et al. |
| 2010/0026809 A1 | 2/2010 | Curry |
| 2010/0045508 A1 | 2/2010 | Ekbal et al. |
| 2010/0054304 A1 | 3/2010 | Barnes et al. |
| 2010/0060452 A1 | 3/2010 | Schuster et al. |
| 2010/0080163 A1 | 4/2010 | Krishnamoorthi et al. |
| 2010/0150117 A1 | 6/2010 | Aweya et al. |
| 2010/0250305 A1* | 9/2010 | Lee .................. G06Q 10/06316 705/7.26 |
| 2010/0278386 A1 | 11/2010 | Hoeflinger |
| 2010/0283630 A1 | 11/2010 | Alsono |
| 2010/0328073 A1 | 12/2010 | Nikitin et al. |
| 2011/0025847 A1 | 2/2011 | Park et al. |
| 2011/0054782 A1 | 3/2011 | Kaahui et al. |
| 2011/0063114 A1 | 3/2011 | Ikoyan |
| 2011/0064023 A1 | 3/2011 | Yamamoto et al. |
| 2011/0084806 A1 | 4/2011 | Pekins et al. |
| 2011/0134240 A1 | 6/2011 | Anderson et al. |
| 2011/0140970 A1 | 6/2011 | Fukagawa et al. |
| 2011/0151953 A1 | 6/2011 | Kim et al. |
| 2011/0159939 A1 | 6/2011 | Lin et al. |
| 2011/0169959 A1 | 7/2011 | DeAngelis et al. |
| 2011/0195701 A1 | 8/2011 | Cook et al. |
| 2011/0261195 A1 | 10/2011 | Martin et al. |
| 2011/0300905 A1 | 12/2011 | Levi |
| 2011/0320322 A1 | 12/2011 | Roslak et al. |
| 2012/0014278 A1 | 1/2012 | Ameti et al. |
| 2012/0015665 A1 | 1/2012 | Farley et al. |
| 2012/0024516 A1 | 2/2012 | Bhadurt et al. |
| 2012/0042326 A1 | 2/2012 | Jain et al. |
| 2012/0057634 A1 | 3/2012 | Shi et al. |
| 2012/0057640 A1 | 3/2012 | Shi et al. |
| 2012/0065483 A1 | 3/2012 | Chung et al. |
| 2012/0081531 A1 | 4/2012 | DeAngelis et al. |
| 2012/0112904 A1 | 5/2012 | Nagy et al. |
| 2012/0126973 A1* | 5/2012 | DeAngelis ......... A63B 24/0021 340/539.13 |
| 2012/0139708 A1 | 6/2012 | Paradiso et al. |
| 2012/0184878 A1 | 7/2012 | Najafi et al. |
| 2012/0212505 A1 | 8/2012 | Burroughs et al. |
| 2012/0218301 A1 | 8/2012 | Miller |
| 2012/0225676 A1 | 9/2012 | Boyd et al. |
| 2012/0231739 A1 | 9/2012 | Chen et al. |
| 2012/0246795 A1 | 10/2012 | Scheffler et al. |
| 2012/0256745 A1 | 10/2012 | Plett et al. |
| 2012/0268239 A1 | 10/2012 | Ljung et al. |
| 2013/0003860 A1 | 1/2013 | Sasai et al. |
| 2013/0021142 A1 | 1/2013 | Matsui et al. |
| 2013/0021206 A1 | 1/2013 | Hach et al. |
| 2013/0041590 A1 | 2/2013 | Burich et al. |
| 2013/0066448 A1* | 3/2013 | Alonso .................. H04Q 9/00 700/91 |
| 2013/0076645 A1 | 3/2013 | Anantha et al. |
| 2013/0096704 A1 | 4/2013 | Case |
| 2013/0115904 A1 | 5/2013 | Kapoor et al. |
| 2013/0138386 A1 | 5/2013 | Jain et al. |
| 2013/0142384 A1 | 6/2013 | Ofek |
| 2013/0147608 A1 | 6/2013 | Sadr |
| 2013/0197981 A1 | 8/2013 | Vendetti et al. |
| 2013/0257598 A1 | 10/2013 | Kawaguchi et al. |
| 2013/0339156 A1 | 12/2013 | Sanjay et al. |
| 2014/0055588 A1 | 2/2014 | Bangera et al. |
| 2014/0062728 A1 | 3/2014 | Soto et al. |
| 2014/0145828 A1 | 5/2014 | Bassan-Eskenazi |
| 2014/0156036 A1 | 6/2014 | Huang |
| 2014/0170607 A1 | 6/2014 | Hsiao et al. |
| 2014/0221137 A1 | 8/2014 | Krysiak et al. |
| 2014/0301427 A1 | 10/2014 | Rabbath et al. |
| 2014/0320660 A1 | 10/2014 | DeAngelis et al. |
| 2014/0345375 A1* | 11/2014 | Hassell, Jr. ............. G01F 17/00 73/149 |
| 2014/0361875 A1 | 12/2014 | O'Hagan et al. |
| 2014/0361890 A1 | 12/2014 | O'Hagan et al. |
| 2014/0361906 A1 | 12/2014 | Hughes et al. |
| 2014/0361928 A1 | 12/2014 | Hughes et al. |
| 2014/0364141 A1 | 12/2014 | O'Hagan et al. |
| 2014/0364973 A1 | 12/2014 | O'Hagan et al. |
| 2014/0364977 A1 | 12/2014 | Wohl et al. |
| 2014/0365415 A1 | 12/2014 | Stelfox et al. |
| 2014/0365639 A1 | 12/2014 | Wohl et al. |
| 2014/0365640 A1 | 12/2014 | Wohl et al. |
| 2015/0002272 A1 | 1/2015 | Alonso et al. |
| 2015/0057981 A1 | 2/2015 | Gross |
| 2015/0085111 A1 | 3/2015 | Lavery |
| 2015/0097653 A1 | 4/2015 | Gibbs et al. |
| 2015/0355311 A1 | 12/2015 | Hughes et al. |
| 2015/0358852 A1 | 12/2015 | Richley et al. |
| 2015/0360133 A1 | 12/2015 | MacCallum et al. |
| 2015/0375041 A1 | 12/2015 | Richley et al. |
| 2015/0375083 A1 | 12/2015 | Stelfox et al. |
| 2015/0378002 A1 | 12/2015 | Hughes et al. |
| 2015/0379387 A1 | 12/2015 | Richley |
| 2016/0008693 A1 | 1/2016 | Cronin |
| 2016/0059075 A1* | 3/2016 | Molyneux ............ A43B 1/0054 700/91 |
| 2016/0097837 A1 | 4/2016 | Richley et al. |

FOREIGN PATENT DOCUMENTS

| | | |
|---|---|---|
| EP | 1253438 A2 | 10/2002 |
| EP | 1503513 A1 | 2/2005 |
| EP | 2474939 A1 | 11/2012 |
| WO | WO 98/05977 | 2/1998 |
| WO | WO 99/61936 A1 | 12/1999 |
| WO | WO 01/08417 | 2/2001 |
| WO | WO 2006/022548 | 3/2006 |
| WO | WO 2010/083943 | 7/2010 |
| WO | WO 2015/051813 A1 | 4/2014 |
| WO | WO 2014/197600 | 12/2014 |

OTHER PUBLICATIONS

International Search Report and Written opinion from International Application No. PCT/US2014/040940 dated Dec. 17, 2014.
Complaint before the United States District Court of Massachusetts, Civil Action No. 1:15-cv-12297, *Lynx System Developers, Inc. et al. V. Zebra Enterprise Solutions Corporation et al.*, filed Jun. 10, 2015.
International Search Report and Written Opinion from International Application No. PCT/US2014/041062 dated Oct. 1, 2014.
International Search Report and Written Opinion from International Application No. PCT/US2014/040947 dated Oct. 9, 2014.
Fontana, R.J., Richley, E., Barney, J., "Commercialization of an Ultra Wideband Precision Assest Location System", 2003 IEEE Conference on Ultra Wideband Systems and Technologies, Nov. 16-19, 2003.
Guéziec, A., "Tracking a Baseball Pitch for Broadcast Television," Computer, Mar. 2002, pp. 38-43 <http://www.trianglesoftware.com/pitch_tracking.htm>.
CattleLog Pro, eMerge Interactive, Inc., Sebastian, FL, 2004.
Marchant, J., "Secure Animal Indetification and Source Verification", JM Communications, UK, 2002.
"A guide to Using NLIS Approved Ear Tags and Rumen Boluses", National Livestock Identification Scheme, Meat & Livestock Australia Limited, North Sydney, Australia, May 2003.

(56) References Cited

OTHER PUBLICATIONS

King L., "NAIS Cattle ID Pilot Projects Not Needed, Since Proven Advanced Technology Already Exisits", ScoringSystem, Inc., Sarasota, FL, Dec. 27, 2005. (www.prweb.com/releases2005/12prweb325888.htm).

"RFID in the Australian Meat and Livestock Industry", Allflex Australia Pty Ltd., Capalaba, QLD (AU), Data Capture Suppliers Guide, 2003-2004.

Swedberg, Claire, "USDA Reseachers Develop System to Track Livestock Feeding Behavior Unobtrusively", RFID Journal, Jul. 18, 2013.

Invitation to Pay Additional Fees/Partial International Search Report for PCT/IB2015/054099 dated Oct. 6, 2015.

Swedberg, C., "N.J. Company Seeks to Market Passive Sensor RFID Tags," RFID Journal, Jun. 14, 2011, pp. 1-2 <http://www.rfidjournal.com/articles/pdf?8527>.

International Search Report and Written Opinion for International Application No. PCT/IB2015/054099 dated Dec. 9, 2015.

U.S. Appl. No. 14/296,703, filed Jun. 5, 2014; In re: Alonso et al., entitle Method and Apparatus for Associating Radio Frequency Identification Tags with Participants.

U.S. Appl. No. 61/895,548, filed Oct. 25, 2013, In re: Alonso et al., entitled "Method, Apparatus, and Computer Program Product for Collecting Sporting Event Data Based on Real Time Data for Proximity and Movement of Objects."

International Search Report and Written Opinion for International Application No. PCT/IB2015/059264 dated Feb. 10, 2016.

Jinyun Zhang et al., "UWB Systems for Wireless Sensor Networks", Proceedings of the IEEE, IEEE. New York, US, vol. 97, No. 2, Feb. 1, 2009 (Feb. 1, 2009), pp. 313-331.

International Search Report and Written Opinion for International Application No. PCT/US2015/034267 dated Sep. 25, 2015.

International Search Report and Written Opinion for International Application No. PCT/IB2015/054103 dated Aug. 14, 2015.

Cheong, P. et al., "Synchronization, TOA and Position Estimation for Low-Complexity LDR UWB Devices", Ultra-Wideband, 2005 IEEE International Conference, Zurich, Switzerland Sep. 5-8, 2005, Piscataway, NJ, USA, IEEE, Sep. 5, 2005, pp. 480-484.

International Search Report and Written Opinion for International Application No. PCT/IB2015/054213 dated Aug. 6, 2015.

Wang, Y. et al., "An Algorithmic and Systematic Approach from Improving Robustness of TOA-Based Localization", 2013 IEEE 10th International Conference on High Performance Computing and Communications & 2013 IEEE, Nov. 13, 2013, pp. 2066-2073.

Guvenc, I. et al., "A Survey on TOA Based Wireless Localization and NLOA Mitigation Techniques", IEEE Communications Surveys, IEEE, New York, NY, US, vol. 11, No. 3, Oct. 1, 2009, pp. 107-124.

International Search Report and Written Opinion for International Application PCT/IB2015/054102 dated Nov. 4, 2015.

"Seattleite wins top prize in Microsoft's Super Bowl tech Contest", San Francisco AP, Komonews.com, Feb. 6, 2016. <http://komonews.com/news/local/seattleite-wins-top-prize-in-microsofts-super-bowl-tech-contest>.

Bahle et al., "I See You: How to Improve Wearable Activity Recognition by Leveraging Information from Environmental Cameras," Pervasive Computing and Communications Workshops, IEEE International Conference, (Mar. 18-22, 2013).

Teixeira et al., "Tasking Networked CCTV Cameras and Mobile Phones to Identify and Localize Multiple People," Ubicomp '10 Proceedings of the 12th ACM International Conference on Ubiquitous Computing, pp. 213-222 (Sep. 26-29, 2010).

Complaint before the United States District Court of Massachusetts, Civil Action No. 1:15-cv-12297, *Lynx System Developers, Inc. et al. V. Zebra Enterprise Solutions Corporation et al.*, filed Mar. 23, 2016.

Defendant's Answer to Complaint before the United States District Court of Massachusetts, Civil Action No. 1:15-cv-12297, *Lynx System Developers, Inc. et al. V. Zebra Enterprise Solutions Corporation et al.*, filed Apr. 6, 2016.

International Search Report for International Application No. PCT/US2014/053647 dated Dec. 19, 2014.

International Search Report and Written Opinion for International Application No. PCT/US2016/035614 dated Sep. 15, 2016.

Zhu et al., "A Real-Time Articulated Human Motion Tracking Using Tri-Axis Inertial/Magnetic Sensors Package," IEEE Transactions on Neural Systems and Rehabilitation Engineering, vol. 12, No. 2, Jun. 2004, pp. 295-302.

\* cited by examiner

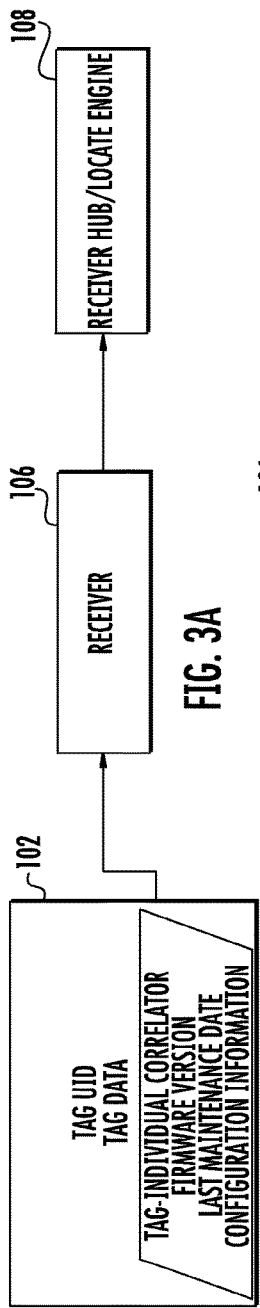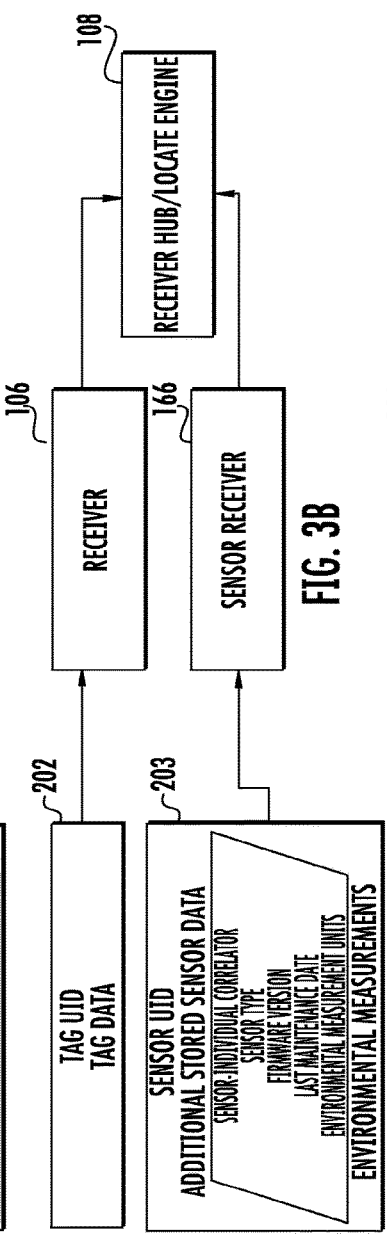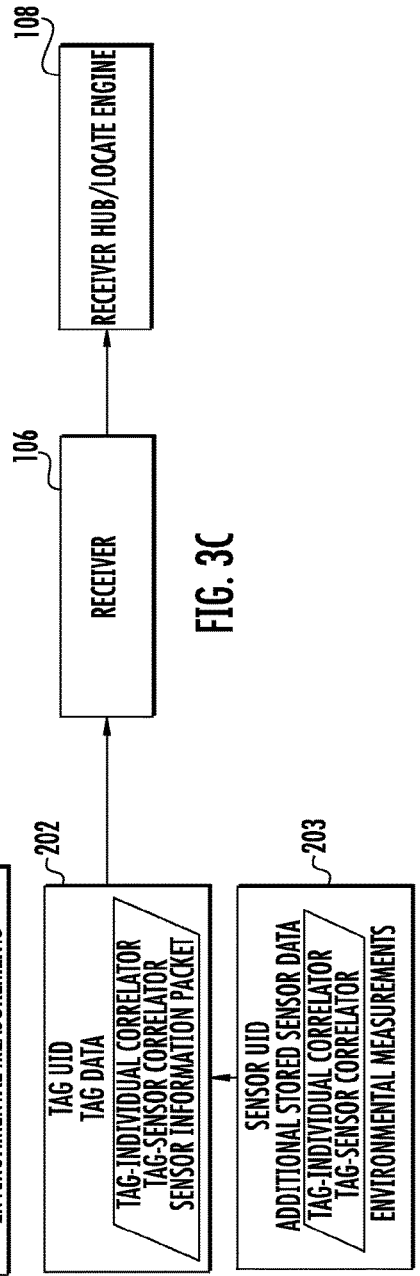

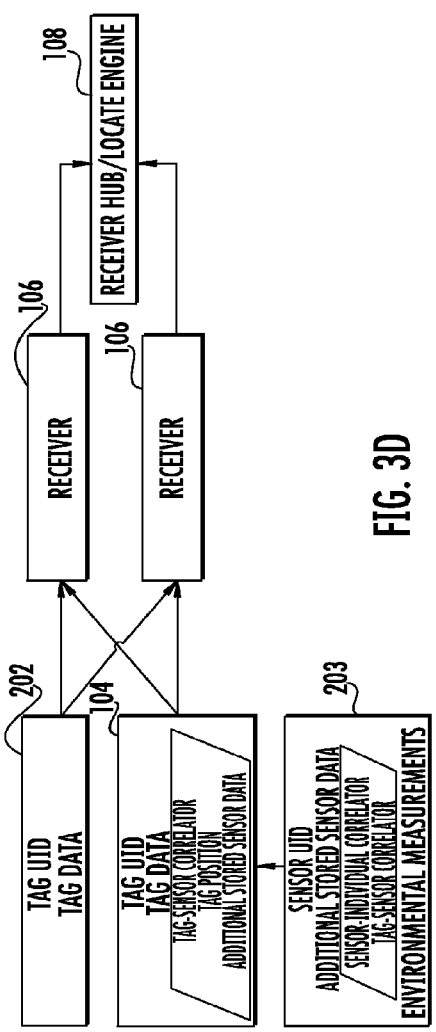
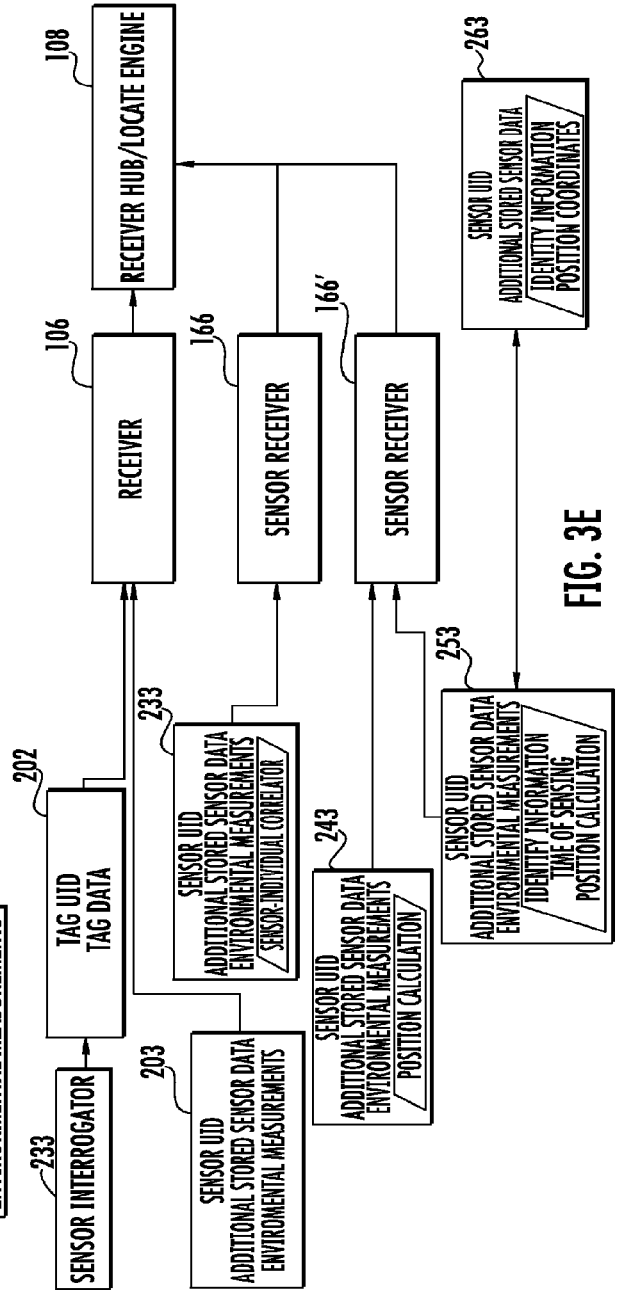
FIG. 3D
FIG. 3E

| TAG UID | INDIVIDUAL |
|---|---|
| 1 | JIM |
| 2 | ED |
| 3 | ED |
| 4 | ANDY |

FIG. 5A

| INDIVIDUAL | PERFORMANCE | | |
|---|---|---|---|
| | AHA | AHB | AHC |
| JIM | 5 | 3 | .2 |
| ED | 5 | 5 | .4 |
| ANDY | 6 | 4 | .1 |

FIG. 5B

| INDIVIDUAL | ROLE |
|---|---|
| JIM | OFFENSIVE LINE |
| ED | QUARTERBACK |
| ANDY | RUNNING BACK |

FIG. 5C

| ROLE | PERFORMANCE | | |
|---|---|---|---|
| | AHA | AHB | AHC |
| OFFENSIVE LINE | 5 | 3 | .2 |
| QUARTERBACK | 5 | 5 | .4 |
| RUNNING BACK | 6 | 4 | .1 |
| DEFENSIVE BACK | 6 | 2 | .25 |

FIG. 5D

| INDIVIDUAL | ROLE | PERFORMANCE | | |
|---|---|---|---|---|
| | | AHA | AHB | AHC |
| JIM | OFFENSIVE LINE | 4 | 3 | .2 |
| JIM | DEFENSIVE LINE | 6 | 3 | .3 |
| ED | QUARTERBACK | 5 | 4 | .05 |
| ANDY | RECEIVER | 6 | 2 | .4 |
| ANDY | RUNNING BACK | 6 | 5 | .15 |

FIG. 5E

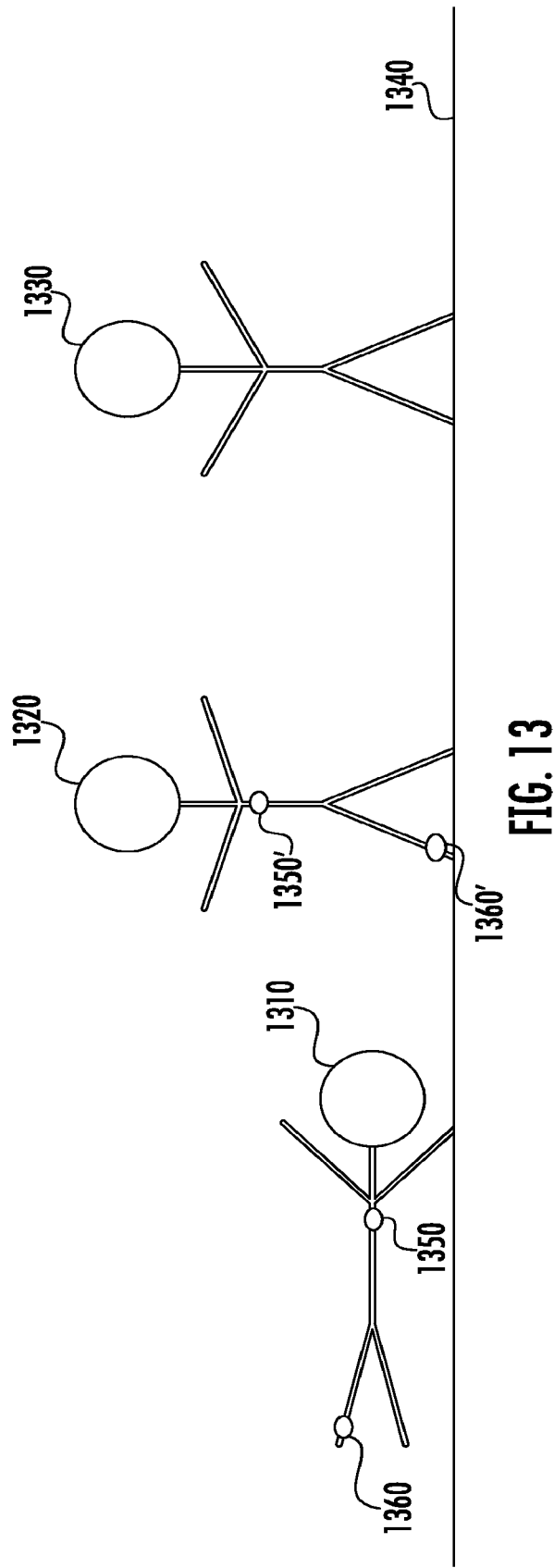

METHOD, APPARATUS, AND COMPUTER PROGRAM PRODUCT FOR TAG AND INDIVIDUAL CORRELATION

CROSS-REFERENCE TO RELATED APPLICATION

This application is a continuation of U.S. patent application Ser. No. 13/942,507 filed Jul. 15, 2013, which claims priority from and the benefit of the filing date of U.S. Provisional Patent Application No. 61/831,990 filed Jun. 6, 2013, the contents of all of which are incorporated by reference in their entirety herein.

FIELD

Embodiments of the invention relate, generally, to monitoring the health, fitness, operation, and performance of individuals using a radio frequency ("RF") location system.

BACKGROUND

Individuals (e.g., persons, patients, athletes, animals, machines, etc.) may encounter circumstances whereby their health, fitness, operation, or performance becomes limited or compromised. Applicant has discovered problems associated with current methods and systems for monitoring the health, fitness, operation, or performance of individuals. Through applied effort, ingenuity, and innovation, Applicant has solved the identified problems by developing a solution that is embodied by the present invention, which is described in detail below.

BRIEF SUMMARY

In general, embodiments of the present invention provided herein include systems, methods and computer readable media for monitoring and determining status information concerning the health, fitness, operation, and performance of individuals using a RF location system and for tag and individual correlation.

In one embodiment a method for monitoring an individual associated with a radio frequency (RF) location tag is provided, the method may comprise receiving tag derived data comprising tag location data and blink data, wherein the tag location data is determined based at least in part on the blink data, receiving sensor derived data indicative of at least one of a health, a fitness, an operation level, or a performance level for the individual, receiving a tag-individual correlator associated with the individual, receiving a tag-sensor correlator associated with the RF location tag, and matching the tag-sensor correlator with the tag-individual correlator to associate the sensor-derived data with the individual. In one embodiment, the tag-individual correlator is received from an individual database. In one embodiment, the tag-individual correlator is determined from the blink data. In one embodiment, the tag-sensor correlator is determined from the blink data.

In another embodiment a method for associating an environmental measurement with an individual is provided, the method comprising associating an individual location with the individual, receiving, from a sensor, a sensor signal comprising one or more environmental measurements indicative of at least one of a health, a fitness, an operation level, or a performance level for the individual, associating a sensor location with the sensor, and determining a sensor-individual correlator based on the individual location being within a threshold distance of the sensor location.

In one embodiment, associating the individual location with the individual comprises receiving a tag signal comprising blink data from a radio frequency (RF) location tag associated with the individual, and determining the individual location associated with the individual based at least in part on the blink data. In one embodiment, associating the individual location with the individual comprises receiving, from a second sensor associated with the individual, a second sensor signal comprising a position calculation, the position calculation determined by a triangulation positioner, and determining the individual location associated with the individual based at least in part on the position calculation.

In one embodiment, associating the individual location with the individual comprises receiving, from a second sensor associated with the individual, a second sensor signal comprising position information, the position information accessed from a proximity label, and determining the individual location associated with the individual based at least in part on the position information. In one embodiment, associating the sensor location with the sensor comprises receiving a tag signal comprising blink data from a radio frequency (RF) location tag associated with the sensor, and determining the sensor location associated with the sensor based at least in part on the blink data.

In one embodiment, associating the sensor location with the sensor comprises receiving a tag signal comprising blink data from a radio frequency (RF) reference tag associated with the sensor, wherein said blink data includes a tag unique identification number, determining a location of the RF reference tag from a Geographical Information System based at least, in part, on the tag unique identification number, and determining the sensor location associated with the sensor based on the location of the RF reference tag. In another embodiment the method may further comprise receiving a differential global positioning system (DGPS) correction signal, and determining the sensor location based on the DGPS correction signal.

In one embodiment, the sensor signal received from the sensor further comprises a position calculation determined by a triangulation positioner, wherein the sensor location associated with the sensor is determined at least in part on the position calculation. In one embodiment, the sensor signal received from the sensor further comprises position information read from a proximity label, wherein the sensor location associated with the sensor is determined at least in part on the position information. In one embodiment a method may further comprise receiving a differential global positioning system (DGPS) correction signal, and determining the individual location associated with the individual based on the DGPS correction signal. In another embodiment the method may further comprise receiving a differential global positioning system (DGPS) correction signal, and determining the sensor location based on the DGPS correction signal.

In another embodiment a method for associating an environmental measurement with an individual is provided, the method comprising associating an individual location with the individual, receiving, from a sensor, a sensor signal comprising one or more environmental measurements indicative of at least one of a health, a fitness, an operation level, or a performance level for the individual, associating a sensor location with the sensor, and associating the sensor with the individual based on the individual location being within a threshold distance of the sensor location. In another embodiment the method may further comprise associating a sensor information packet, derived from the sensor signal, with the individual.

In another embodiment a computer program product for monitoring an individual associated with a radio frequency (RF) location tag may be provided, the computer program product comprising at least one computer-readable storage medium having computer-executable program code instructions stored therein, the computer-executable program code instructions comprising program code instructions for receiving tag derived data comprising tag location data and blink data, wherein the tag location data is determined based at least in part on the blink data, receiving sensor derived data indicative of at least one of a health, a fitness, an operation level, or a performance level for the individual, receiving a tag-individual correlator associated with the individual, receiving a tag-sensor correlator associated with the RF location tag, and matching the tag-sensor correlator with the tag-individual correlator to associate the sensor-derived data with the individual.

In one embodiment, the tag-individual correlator is received from an individual database. In one embodiment, the tag-individual correlator is determined from the blink data. In one embodiment, the tag-sensor correlator is determined from the blink data.

In another embodiment a computer program product for associating an environmental measurement with an individual may be provided, the computer program product comprising at least one computer-readable storage medium having computer-executable program code instructions stored therein, the computer-executable program code instructions comprising program code instructions for associating an individual location with the individual, receiving, from a sensor, a sensor signal comprising one or more environmental measurements indicative of at least one of a health, a fitness, an operation level, or a performance level for the individual, associating a sensor location with the sensor, and determining a sensor-individual correlator based on the individual location being within a threshold distance of the sensor location.

In one embodiment, associating the individual location with the individual comprises receiving a tag signal comprising blink data from a radio frequency (RF) location tag associated with the individual, and determining the individual location associated with the individual based at least in part on the blink data. In one embodiment, associating the individual location with the individual comprises receiving, from a second sensor associated with the individual, a second sensor signal comprising a position calculation, the position calculation determined by a triangulation positioner, and determining the individual location associated with the individual based at least in part on the position calculation.

In one embodiment, associating the individual location with the individual comprises receiving, from a second sensor associated with the individual, a second sensor signal comprising position information, the position information accessed from a proximity label, and determining the individual location associated with the individual based at least in part on the position information. In one embodiment, associating the sensor location with the sensor comprises receiving a tag signal comprising blink data from a radio frequency (RF) location tag associated with the sensor, and determining the sensor location associated with the sensor based at least in part on the blink data.

In one embodiment, associating the sensor location with the sensor comprises receiving a tag signal comprising blink data from a radio frequency (RF) reference tag associated with the sensor, wherein said blink data includes a tag unique identification number, determining a location of the RF reference tag from a Geographical Information System based at least, in part, on the tag unique identification number, and determining the sensor location associated with the sensor based on the location of the RF reference tag. In one embodiment, the computer-executable program code instructions further comprise program code instructions for receiving a differential global positioning system (DGPS) correction signal, and determining the individual location associated with the individual based on the DGPS correction signal. In one embodiment, the computer-executable program code instructions further comprise program code instructions for receiving a differential global positioning system (DGPS) correction signal, and determining the sensor location based on the DGPS correction signal.

In one embodiment, the sensor signal received from the sensor further comprises a position calculation determined by a triangulation positioner, wherein the sensor location associated with the sensor is determined at least in part on the position calculation. In one embodiment, the sensor signal received from the sensor further comprises position information read from a proximity label, wherein the sensor location associated with the sensor is determined at least in part on the position information. In one embodiment, the computer-executable program code instructions further comprise program code instructions for receiving a differential global positioning system (DGPS) correction signal, and determining the sensor location based on the DGPS correction signal.

In another embodiment an apparatus for monitoring an individual associated with a radio frequency (RF) location tag may be provided, the apparatus comprising a processor and a memory having computer code stored therein, the computer code configured, when executed by the processor, to cause the apparatus to receive tag derived data comprising tag location data and blink data, wherein the tag location data is determined based at least in part on the blink data, receive sensor derived data indicative of at least one of a health, a fitness, an operation level, or a performance level for the individual, receive a tag-individual correlator associated with the individual, receive a tag-sensor correlator associated with the RF location tag, and match the tag-sensor correlator with the tag-individual correlator to associate the sensor-derived data with the individual.

In one embodiment, the tag-individual correlator is received from an individual database. In one embodiment, the tag-individual correlator is determined from the blink data. In one embodiment, the tag-sensor correlator is determined from the blink data. In one embodiment, the tag-sensor correlator is determined from the sensor-derived data.

In another embodiment an apparatus for associating an environmental measurement with an individual may be provided, the apparatus comprising a processor and a memory having computer code stored therein, the computer code configured, when executed by the processor, to cause the apparatus to associate an individual location with the individual, receive, from a sensor, a sensor signal comprising one or more environmental measurements indicative of at least one of a health, a fitness, an operation level, or a performance level for the individual, associate a sensor location with the sensor, and determine a sensor-individual correlator based on the individual location being within a threshold distance of the sensor location.

In one embodiment, associating the individual location with the individual comprises receiving a tag signal comprising blink data from a radio frequency (RF) location tag associated with the individual, and determining the individual location associated with the individual based at least in part on the blink data. In one embodiment, associating the individual location with the individual comprises receiving, from a second sensor associated with the individual, a second sensor signal comprising a position calculation, the position calculation determined by a triangulation positioner, and determining the individual location associated with the individual based at least in part on the position calculation.

In one embodiment, associating the individual location with the individual comprises receiving, from a second sensor associated with the individual, a second sensor signal comprising position information, the position information accessed from a proximity label, and determining the individual location associated with the individual based at least in part on the position information. In one embodiment, associating the sensor location with the sensor comprises receiving a tag signal comprising blink data from a radio frequency (RF) location tag associated with the sensor, and determining the sensor location associated with the sensor based at least in part on the blink data.

In one embodiment, associating the sensor location with the sensor comprises receiving a tag signal comprising blink data from a radio frequency (RF) reference tag associated with the sensor, wherein said blink data includes a tag unique identification number, determining a location of the RF reference tag from a Geographical Information System based at least, in part, on the tag unique identification number, and determining the sensor location associated with the sensor based on the location of the RF reference tag.

In one embodiment, the sensor signal received from the sensor further comprises a position calculation determined by a triangulation positioner, wherein the sensor location associated with the sensor is determined at least in part on the position calculation. In one embodiment, the computer code is further configured, when executed by the processor, to cause the apparatus to receive a differential global positioning system (DGPS) correction signal, and determine the sensor location based on the DGPS correction signal.

In one embodiment, the sensor signal received from the sensor further comprises position information read from a proximity label, wherein the sensor location associated with the sensor is determined at least in part on the position information. In one embodiment, the computer code is further configured, when executed by the processor, to cause the apparatus to receive a differential global positioning system (DGPS) correction signal, and determine the sensor location based on the DGPS correction signal.

In another embodiment an apparatus for associating an environmental measurement with an individual may be provided, the apparatus comprising a processor and a memory having computer code stored therein, the computer code configured, when executed by the processor, to cause the apparatus to associate an individual location with the individual, receive, from a sensor, a sensor signal comprising one or more environmental measurements indicative of at least one of a health, a fitness, an operation level, or a performance level for the individual, associate a sensor location with the sensor, and associate the sensor with an individual based on the individual location being within a threshold distance of the sensor location.

In another embodiment an apparatus for associating an environmental measurement with an individual may be provided, the apparatus comprising a processor and a memory having computer code stored therein, the computer code configured, when executed by the processor, to cause the apparatus to associate an individual location with the individual, receive, from a sensor, a sensor signal comprising a sensor information packet, associate a sensor location with the sensor, and associate the sensor information packet with the individual based on the individual location being within a threshold distance of the sensor location.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

FIGS. 3A-3E are block diagrams showing the input and output of receivers in accordance with an example embodiment;

FIGS. 5A-5E are block diagrams showing contents of one or more of an individual database and a role database in accordance with an example embodiment;

FIG. 13 is an example illustration showing how the use of tag data may be utilized to monitor the health, fitness, operation, or performance of an individual, in accordance with an example embodiment;

DETAILED DESCRIPTION

Figure 1:
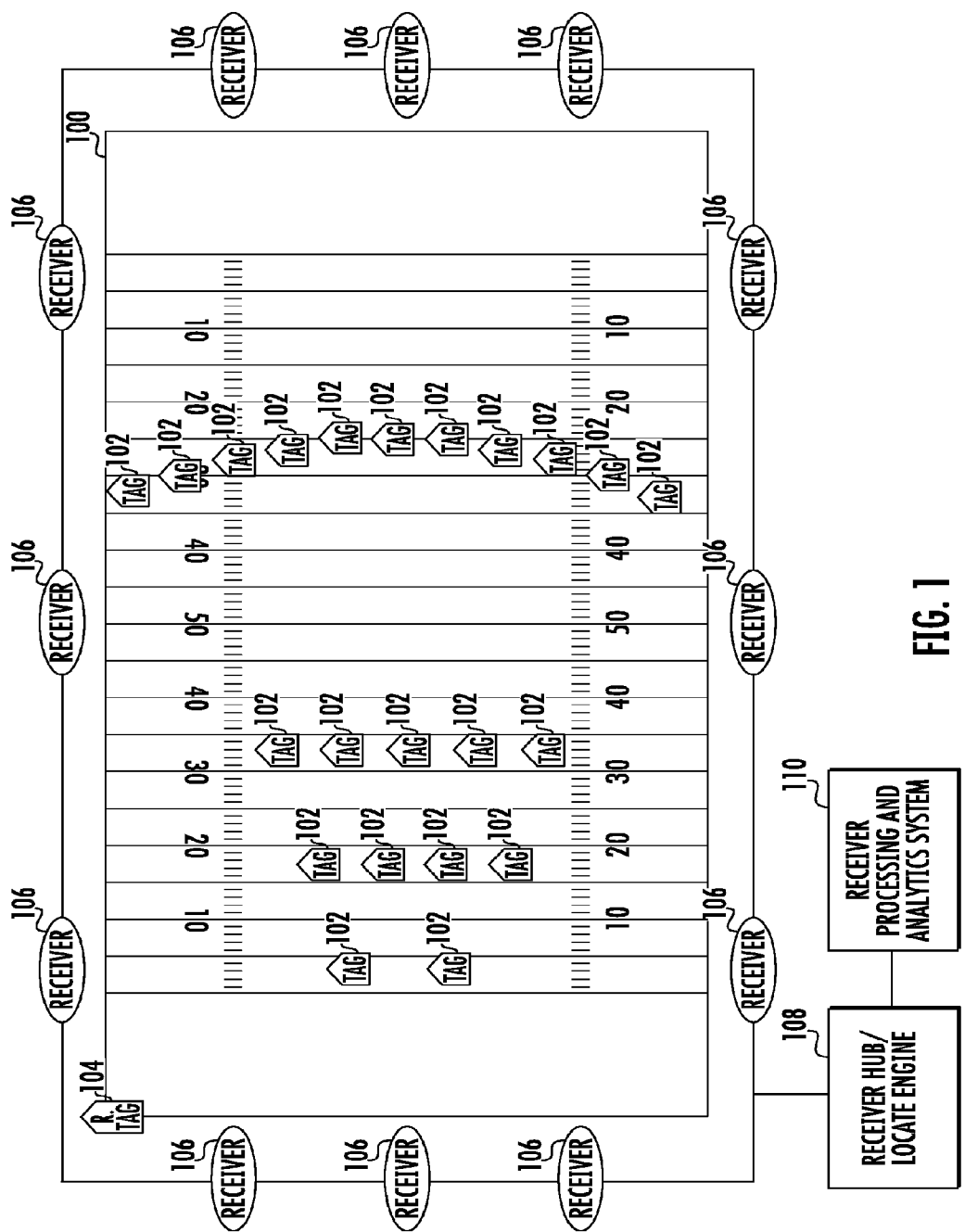
FIG. 1 is block diagram of a RF location system that is configured to monitor the health, fitness, operation, and performance of individuals in accordance with an example embodiment.

Embodiments of the present invention now will be described more fully hereinafter with reference to the accompanying drawings, in which some, but not all embodiments of the inventions are shown. Indeed, embodiments of the invention may be embodied in many different forms and should not be construed as limited to the embodiments set forth herein; rather, these embodiments are provided so that this disclosure will satisfy applicable legal requirements. Like numbers refer to like elements throughout.

As used herein, the terms "data," "content," "information" and similar terms may be used interchangeably to refer to data capable of being captured, transmitted, received, displayed and/or stored in accordance with various example embodiments. Thus, use of any such terms should not be taken to limit the spirit and scope of the disclosure. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, and/or the like.

Brief Overview

The methods, apparatus and computer program products described herein are operable to monitor the health, fitness, operation, and performance of individuals. In some embodiments, the health, fitness, operation, and performance of individuals are monitored based on highly accurate location and/or position data associated with the monitored individuals. Such highly accurate location and/or position data may be further improved with the use of sensor data to provide real-time health, fitness, operation, and performance information concerning the monitored individuals.

The term "individual" as used herein refers to a person, patient, athlete, an animal, a machine (e.g., a race car), or other entity having health, fitness, operation, or performance levels that may be deemed appropriate for remote monitoring.

Health may generally refer to a condition (e.g., healthy, sick, injured, tired, stressed, dehydrated, dizzy) of an individual. Health may include, but is not limited to, identifying whether an individual is healthy and if not, which of one or more conditions the individual may be afflicted with (e.g., the flu). A health model may include, but is not limited to, particular sensor data and associated thresholds or ranges of health related parameters that may indicate one or more conditions.

Fitness may generally refer to whether an individual or object is capable or suitable for performing a function. Fitness may include, but is not limited to, an ability to perform a function. A fitness model may include, but is not limited to, particular sensor data and associated thresholds or ranges of fitness parameters that may indicate one or more functions. For example, if sensor data indicates a stride length of 20+ feet and/or a sustained heart rate of 220+ beats per minutes, an associated fitness model may indicate a horse is performing such feats, and may then look to functions horses may perform. Operation may generally relate to the practical application of a process. Operation may include, but is not limited to, identifying whether an individual is injured or not, and if so, with what injury an individual may be afflicted with (e.g., sprained ankle) and/or at what level may the individual operate at. An operation model may include, but is not limited to, particular sensor data and associated thresholds or ranges that may indicate one or more injuries and/or a percentage of optimal operation. As an example, an individual athlete may take a mental test which can be used as a baseline operation model. If the individual athlete then takes a similar mental test after a head injury and performance differs significantly from the first mental test, the individual may be diagnosed as being in a dizzy or disoriented condition and may predict that the injury cause of the condition is a concussion.

Performance may include, but is not limited to, the manner or quality of functioning or an indication of a performance level. In one embodiment, performance may be generally described as a vector of measurements as discussed in greater detail below. A performance model may include, but is not limited to, particular sensor data and associated thresholds or ranges that may indicate performance quality and/or one or more performance levels. In the concussion example, the mental test defines the measurements for the operation model. When the athlete takes the initial test, the measurements are recorded, establishing the baseline performance level. When the athlete takes the second test, the measurements are recorded, establishing a second performance level. Comparing the second performance level to the baseline performance level involves comparing at least some of the measurements from the second test to the corresponding measurements from the first test.

There are many reasons why one may wish to monitor the health, fitness, operation, and performance of individuals in real time or near-real time. For example, one may wish to make sure that if a person is hurt that someone else is alerted to provide aid, e.g., a parent, a trainer, a paramedic or other health care professional. In some cases, it may be obvious that a person is hurt (e.g., they fall down, cry, scream, or become unconscious). In other circumstances, their injuries may be less obvious (e.g., stimulus response times may be slowed, they may limp, or they may otherwise move or perform abnormally). In still other circumstances, health, fitness, operation, and performance degradations may only be determined using sensors making appropriate measurements (e.g., heart rate, breathing, body temperature, blood chemistry, etc.). In certain circumstances, multiple measurements may be needed to identify degradations.

With the advent of location tracking in sports, it is possible to use precise position information to facilitate monitoring of health and fitness of players, referees, bat boys, coaches, mascots, beer vendors, racing sausages, or even fans in new ways that are easier, faster, and can provide additional information. In this regard, dynamics/kinetics models may be utilized also. A dynamics/kinetics model may include, but is not limited to, position information and associated actions. For example, location data indicating a track shape may indicate an action of "running on a track" or the like. In another embodiment, actions may include or be indicative of non-actions, such as lying down or standing still. In another example, multi-dimensional position information that includes arm/hand position and leg/foot position could indicate that a person is running, lying on the ground, or positioned in a three-point football stance.

Various embodiments of the invention are directed to monitoring the health, fitness, operation, and performance of individuals using a RF location system that is configured to aggregate location information with other sensor data. In this regard, such embodiments are configurable to provide alerts, analytics, and statistics that may be used to diagnose, treat, and improve the health, fitness, operation, and performance of individuals.

Example RF Location System Architecture

FIG. 1 illustrates a radio frequency locating system useful for determining the location of an object (e.g. a football player on a football field) by determining RF location tag 102 (e.g., a ultra-wide band (UWB) location tag) location information at each receiver 106 (e.g., UWB reader, etc.); a timing reference clock to synchronize the frequency of counters within each receiver 106; and, in some examples, a reference tag 104, preferably a UWB transmitter, positioned at known coordinates to enable phase offset between counters to be determined. The systems described herein may be referred to as either "multilateration" or "geolocation" systems; terms which refer to the process of locating a signal source by solving for the mathematical intersection of multiple hyperbolae determined by the difference of arrival times of a signal received at multiple receivers.

In some examples, the system comprising at least the tags 102 and the receivers 106 is configured to provide two dimensional and/or three dimensional precision localization (e.g., subfoot resolutions), even in the presence of multipath interference, due in part to the use of short nanosecond duration pulses whose time-of-flight can be accurately determined using detection circuitry, such as in the receivers 106, which can trigger on the leading edge of a received waveform. In some examples, this short pulse characteristic allows necessary data to be conveyed by the system at a higher peak power, but lower overall power levels, than a wireless system configured for high data rate communications, yet still operate within local regulatory requirements which may limit overall power levels.

In some examples, the tags 102 may operate with an instantaneous −3 dB bandwidth of approximately 400 MHz and an average transmission rate below a 187.5 kHz regulatory cutoff. In such examples, the predicted maximum range of the system, operating at 6.0 GHz, is roughly 311 meters. Such a configuration advantageously satisfies constraints applied by regulatory bodies related to peak and average power densities (e.g., effective isotropic radiated power density), while still optimizing system performance related to range and interference. In further examples, tag transmissions with a −3 dB bandwidth of approximately 400 MHz yields, in some examples, an instantaneous pulsewidth of roughly 2.5 nanoseconds which enables a resolution to better than 30 centimeters.

Referring again to FIG. 1, the object to be located has an attached RF location tag 102, preferably a tag having a UWB transmitter, that transmits a signal comprising a burst (e.g., 72 pulses at a burst rate of 1 Mb/s), and optionally, a burst having a tag data packet that may include tag data elements that may include, but are not limited to, a tag unique identification number (tag UID), other identification information, a sequential burst count, stored tag data, or other desired information for object or personnel identification, inventory control, etc. In some embodiments, the tag data packet may include a tag-individual correlator that can be used to associate a specific individual with a specific tag. In some examples, the sequential burst count (e.g., a packet sequence number) from each tag 102 may be advantageously provided in order to permit, at a receiver hub 108, correlation of time of arrival (TOA) measurement data from various receivers 106.

In some examples, the RF location tag 102 may employ UWB waveforms (e.g., low data rate waveforms) to achieve extremely fine resolution because of their extremely short pulse (i.e., sub-nanosecond to nanosecond, such as a 2 ns (ins up and Ins down)) durations. As such, the tag data packet may be of a short length (e.g., 72-112 bits in some example embodiments), that advantageously enables a higher throughput and higher transmission rates. In some examples, higher throughput and/or higher transmission rates may result in larger datasets for filtering to achieve a more accurate location estimate. In some examples, rates of up to approximately 2600 updates per second can be accommodated without exceeding regulatory requirements. Alternatively or additionally, in some examples, the length of the tag data packets, in conjunction with other system functionality, may also result in a longer battery life (e.g., a 3.0 v 1 A-hr lithium cell battery may result in a tag battery life in excess of 3.8 years).

In some examples, one or more other tags, such as a reference tag 104, may be positioned within and/or about a monitored area, such as monitored area 100 illustrated herein as a football field. In some examples, the reference tag 104 may be configured to transmit a signal that is used to measure the relative phase (e.g., the count of free-running counters) of non-resettable counters within the receivers 106.

One or more (preferably four or more) receivers 106 are also at locations with predetermined coordinates within and/or around the monitored area 100. In some examples, the receivers 106 may be connected in a "daisy chain" fashion to advantageously allow for a large number of receivers 106 to be interconnected over a significant monitored area in order to reduce and simplify cabling, reduce latency, provide power and/or the like. Each of the receivers 106 includes a receiver for receiving transmissions, such as UWB transmissions, and preferably, a packet decoding circuit that extracts a time of arrival (TOA) timing pulse train, transmitter ID, packet number and/or other information that may have been encoded in the tag transmission signal (e.g., material description, personal information, etc.) and is configured to sense signals transmitted by the tags 102 and one or more reference tags 104 (if present).

Each receiver 106 includes a time measuring circuit that measures time differences of arrival (TDOA) of tag bursts. The time measuring circuit is phase-locked (e.g., phase differences do not change and therefore respective frequencies are identical) with a common digital reference clock signal distributed via cable connection from a receiver hub 108 having a central timing reference clock generator. The reference clock signal establishes a common timing reference for the receivers 106. Thus, multiple time measuring circuits of the respective receivers 106 are synchronized in frequency, but not necessarily in phase. While there typically may be a phase offset between any given pair of receivers in the receivers 106, the offset is readily determined through use of a reference tag 104. Alternatively or additionally, each receiver may be synchronized wirelessly via virtual synchronization without a dedicated physical timing channel.

In some example embodiments, the receivers 106 are configured to determine various attributes of the received signal. Since measurements are determined at each receiver 106, in a digital format, rather than analog, signals are transmittable to the receiver hub 108. Advantageously, because packet data and measurement results can be transferred at high speeds to a receiver memory, the receivers 106 can receive and process tag (and corresponding object)

locating signals on a nearly continuous basis. As such, in some examples, the receiver memory allows for a high burst rate of tag events (i.e., tag data packets) to be captured.

Data cables or wireless transmissions may convey measurement data from the receivers 106 to the receiver hub 108 (e.g., the data cables may enable a transfer speed of 2 Mbps). In some examples, measurement data is transferred to the receiver hub at regular polling intervals.

As such, the receiver hub 108 determines or computes tag location (i.e., object location) by processing TDOA measurements related to multiple data packets detected by the receivers 106. In some example embodiments, the receiver hub 108 may be configured to resolve the coordinates of a tag using nonlinear optimization techniques. The receiver hub 108 may also be referred to herein as a locate engine or a receiver hub/locate engine.

In some examples, the system described herein may be referred to as an "over-specified" or "over-determined" system. As such, the receiver hub 108 may then calculate one or more valid (i.e., most likely) locations based on a set of measurements and/or one or more incorrect (i.e., less likely) locations. For example, a location may be calculated that is impossible due the laws of physics (e.g., a tag on a football player that travels more than 100 yards in 1 second) or may be an outlier when compared to other determined locations. As such one or more algorithms or heuristics may be applied to minimize such error.

One such algorithm for error minimization, which may be referred to as a time error minimization algorithm, may be described as $$\varepsilon = \sum_{j=1}^{N} \sum_{k=j+1}^{N} \left\{ (t_j - t_k) - \frac{1}{c} \left[ \frac{[(x-x_j)^2 + (y-y_j)^2 + (z-z_j)^2]^{\frac{1}{2}} -}{[(x-x_k)^2 + (y-y_k)^2 + (z-z_k)^2]^{\frac{1}{2}}} \right] \right\}^2$$

where N is the number of receivers, c is the speed of light, $x_{j,k}$, $y_{j,k}$ and $z_{j,k}$ are the coordinates of the receivers and $t_{j,k}$ are the arrival times received at each of the receivers. Note that only time differences may be received at receiver 106 in some example embodiments. The starting point for the minimization is obtained by first doing an area search on a coarse grid of x, y and z over an area defined by the user. This is followed by a localized steepest descent search.

Another or second algorithm for error minimization, which may be referred to as a distance error minimization algorithm, may be defined by:

$$\varepsilon = \sum_{j=1}^{N} \left[ [(x-x_j)^2 + (y-y_j)^2 + (z-z_j)^2]^{\frac{1}{2}} - c(t_j - t_0) \right]^2$$

where time and location differences are replaced by their non-differential values by incorporating an additional unknown dummy variable, $t_0$, which represents an absolute time epoch. The starting point for this algorithm is fixed at the geometric mean location of all active receivers. No initial area search is needed, and optimization proceeds through the use of a Davidon-Fletcher-Powell (DFP) quasi-Newton algorithm in some examples.

In order to determine the coordinates of a tag (T), in some examples and for calibration purposes, a reference tag (e.g., reference tag 104) is positioned at a known coordinate position $(x_T, y_T, z_T)$.

In further example embodiments, a number N of receivers $\{R_j: j=1, \ldots, N\}$ (e.g., receivers 106) are positioned at known coordinates $(x_{R_j}, y_{R_j}, z_{R_j})$, which are respectively located at distances, such as:

$$d_{R_j} = \sqrt{(x_{R_j} - x_T)^2 + (y_{R_j} - y_T)^2 + (z_{R_j} - z_T)^2}$$

from a reference tag.

Each receiver $R_j$ utilizes, for example, a synchronous clock signal derived from a common frequency time base, such as clock generator. Because the receivers are not synchronously reset, an unknown, but constant offset $O_j$ exits for each receiver's internal free running counter. The value of the offset $O_j$ is measured in terms of the number of fine resolution count increments (e.g., a number of nanoseconds for a one nanosecond resolution system).

The reference tag is used to calibrate the radio frequency locating system as follows:

The reference tag emits a signal burst at an unknown time $\tau_R$. Upon receiving the signal burst from the reference tag, a count $N_{R_j}$ as measured at receiver $R_j$ is given by $$N_{R_j} = \beta \tau_R + O_j + \beta d_{R_j}/c$$

where c is the speed of light and $\beta$ is the number of fine resolution count increments per unit time (e.g., one per nanosecond). Similarly, each object tag $T_i$ of each object to be located transmits a signal at an unknown time $\tau_i$ to produce a count $$N_{ij} = \beta \tau_i + O_j + \beta d_{ij}/c$$

at receiver $R_j$ where $d_{ij}$ is the distance between the object tag $T_i$ and the receiver at receiver $R_j$. Note that $\tau_i$ is unknown, but has the same constant value for receivers of all receivers $R_j$. Based on the equalities expressed above for receivers $R_j$ and $R_k$ and given the reference tag information, differential offsets expressed as differential count values are determined as follows:

$$N_{R_j} - N_{R_k} = (O_j - O_k) + \beta \left( \frac{d_{R_j}}{c} - \frac{d_{R_k}}{c} \right) \text{ or}$$

$$(O_j - O_k) = (N_{R_j} - N_{R_k}) - \beta \left( \frac{d_{R_j}}{c} - \frac{d_{R_k}}{c} \right) = \Delta_{jk}$$

$\Delta_{jk}$ is constant as long as $d_{Rj} - d_{Rk}$ remains constant, (which means the receivers and tag are fixed and there is no multipath situation) and $\beta$ is the same for each receiver. Note that $\Delta_{jk}$ is a known quantity, since $N_{R_j}$, $N_{R_k}$, $\beta$, $d_{R_j}/c$, and $d_{R_k}/c$ are known. That is, the differential offsets between receivers $R_j$ and $R_k$ may be readily determined based on the reference tag transmissions. Thus, again from the above equations, for an object tag ($T_i$) transmission arriving at receivers $R_j$ and $R_k$:

$$N_{ij} - N_{ik} = (O_j - O_k) + \beta(d_{ij}/c - d_{ik}/c) = \Delta_{jk} + \beta(d_{ij}/c - d_{ik}/c)$$

or, $$d_{ij} - d_{ik} = (c/\beta)[N_{ij} - N_{ik} - \Delta_{jk}].$$

The process further includes determining a minimum error value $E_i$, for each object tag $T_i$, according to the functional relationship:

$$E_i = \min_{(x,y,z)} \sum_j \sum_{k>j} \left[ (d_{ij} - d_{ik}) - (dist(T_{x,y,z}, R_j) - dist(T_{x,y,z}, R_k)) \right]^2$$

-continued $$\text{where } dist(T_{x,y,z}, R_j) = \sqrt{(x_{R_j} - x)^2 + (y_{R_j} - y)^2 + (z_{R_j} - z)^2}$$

is the Euclidean distance between point (x,y,z) and the coordinates of the $j^{th}$ receiver $R_j$. The minimization solution (x',y',z') is the estimated coordinate position for the $i^{th}$ tag at $t_0$.

In an example algorithm, this proceeds according to:

$$\varepsilon = \sum_{j=1}^{N} \left[ [(x - x_j)^2 + (y - y_j)^2 + (z - z_j)^2]^{\frac{1}{2}} - c(t_j - t_0) \right]^2$$

where each arrival time, $t_j$, is referenced to a particular receiver (receiver "1") as follows:

$$t_j = \frac{1}{\beta}(N_j - N_1 - \Delta_{j_k})$$

and the minimization is performed over variables (x, y, z, $t_0$) to reach a solution (x', y', z', $t_0$').

In some example embodiments, the location of a tag 102 (e.g., tag location data) may then be output to the receiver processing and analytics system 110 for further processing to advantageously provide visualizations, predictive analytics and/or the like.

Individuals Equipped with Location Tags and Sensors

FIG. 1 shows a monitored area 100. The monitored area 100 comprises a plurality of positions at one or more time epochs. The plurality of positions may be divided into one or more zones. Each zone may be described by one or more coordinate systems, such as a local NED (North-East-Down) system, a latitude-longitude system, or even a yard line system as might be used for an American football game. A location is a description of a position, or a plurality of positions, within the monitored area. For example, a field marker at the intersection of the south goal line and west out of bounds line at Bank of America Stadium in Charlotte, N.C. could be described as {0,0,0} in a local NED system, or 35.225336 N 80.85273 W longitude 751 ft. altitude on a latitude-longitude system, or simply "Panthers Goal Line" in a yard line system. Because different types of locating systems or different zones within a single locating system may use different coordinate systems, a Geographical Information System may be used to associate location data.

Figure 2A:
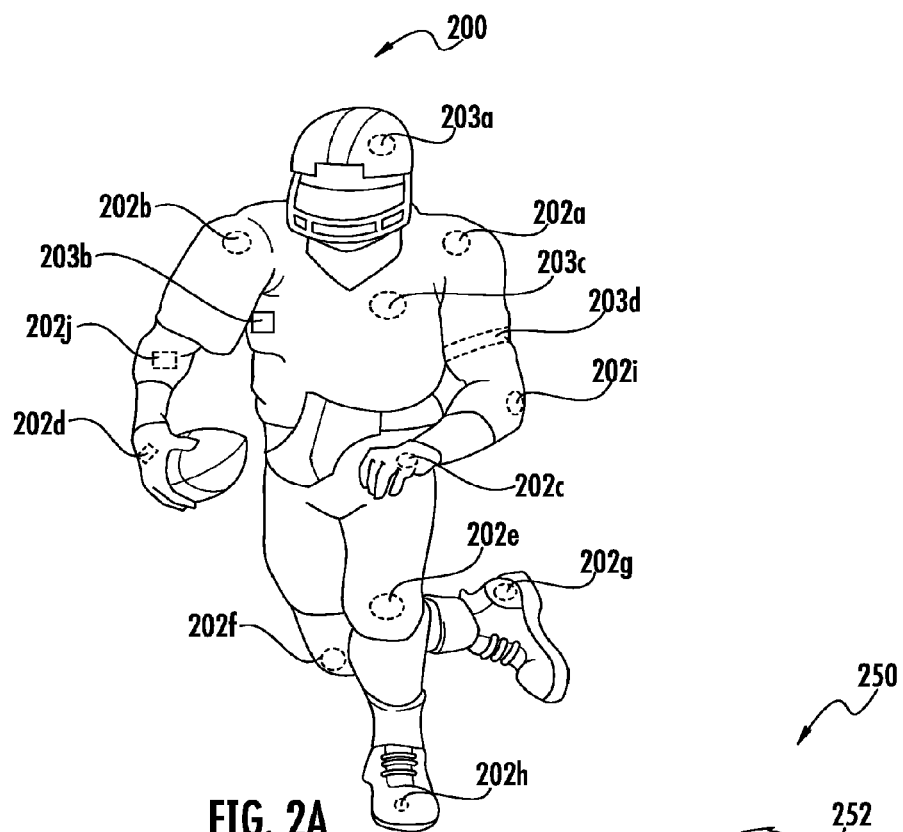
FIGS. 2A and 2B are example illustrations of individuals equipped with an exemplary arrangement of tags and sensors in accordance with some example embodiments.
Figure 2B:
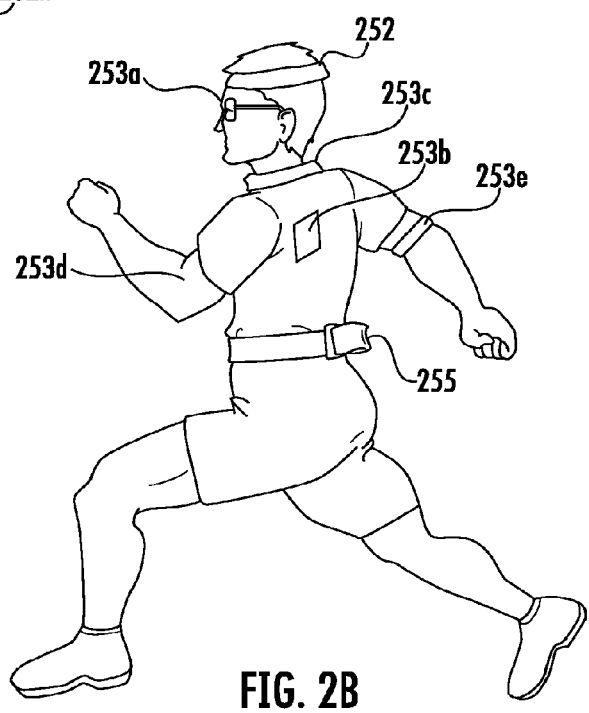

FIGS. 2A and 2B illustrate example individuals equipped with tags and/or sensors that are configured to transmit signals to receivers of a RF location system. As will be apparent to one of ordinary skill in the art in view of this disclosure, the composition and arrangement of the tags and sensors used on a selected individual may change based on the health, fitness, operation, and performance parameters that are intended for monitoring, as well as practical considerations regarding the equipment to be worn.

FIG. 2A depicts an individual 200, shown here for exemplary purposes as a football player, equipped with a number of tags 202a-j and sensors 203a-d. The term "sensor" as used herein refers to any device that detects, measures, indicates or records a parameter associated with an individual's health, fitness, operation, or performance.

The depicted individual 200 is equipped with a plurality of tags 202a-j (e.g., the RF location tags 102 discussed in connection with FIG. 1) to provide robust location data for determining information concerning the body motion kinetics of the tagged individual 200. In particular, the individual 200 is equipped with tags 202a and 202b positioned proximate to the individual's shoulder area (here under shoulder pads), tags 202c and 202d positioned in gloves proximate to the individual's hands, tags 202e and 202f positioned in knee pads proximate to the individual's knees, tags 202g and 202h positioned in shoes proximate to the individual's feet, and tags 202i and 202j positioned in sleeves or elbow pads proximate to the individual's elbows.

As discussed above, each tag may be a device configured for transmitting a signal, for example, a UWB signal that includes a TOA timing pulse, and optionally, a tag data packet that may include, but is not limited to, ID information (e.g., tag UID), a sequential burst count or other desired information. The tag signals (e.g., blink data) may be collected and used, e.g., by the receiver hub 108 of FIG. 1, to determine tag location data at one or more times, which may in turn be used, e.g., by the receiver processing and analytics system 110 of FIG. 1, to determine location data and body motion kinetics of the tagged individual. The tag signal may include analog and/or digital data.

While FIG. 2A illustrates an example embodiment employing multiple tags 202a-j, one of ordinary skill in the art will readily appreciate that more or fewer tags 202 may be used. For example, in one embodiment where simple location of the individual is all that is desired (as opposed to information concerning the motion of arms, legs, or other tagged appendages), a single tag may be used (as shown in FIG. 2B).

The individual 200 depicted in FIG. 2A is further equipped with a plurality of sensors 203a-d. In particular, the individual is equipped with sensor 203a, which is an accelerometer positioned in a helmet proximate to the individual's head; sensor 203b, which is a body temperature sensor positioned in a jersey under the individual's arm; sensor 203c, which is a heart rate sensor positioned in a shoulder pads breastplate proximate to the individual's chest; and sensor 203d, which is a blood pressure sensor positioned on an arm band proximate to the individual's arm. Similarly, one or more sensors could be used, perhaps together with dimensional data, to measure the motion of appendages of the individual, to measure relative motion of appendages relative to one or more tags, or to measure aspects of a tag, such as motion, direction, or acceleration, temperature, etc. Dimensional data could include anatomical dimension information such as, for example, the measured length of individual appendages (femur, arm, finger, wheel circumference) or combined dimensions (height, stride, wingspan, body length), or equipment dimensions (shoe, wristband, shirt, lance, spear, pole, bat) or other measured or calculated dimensions as may be useful in determining expected or actual motion.

FIG. 2B shows a second individual 250, shown here for exemplary purposes as a runner, equipped with a tag 252 and a number of sensors 253a-e. The depicted tag 252 is positioned on a head band proximate to the individual's head to encourage better transmission performance (i.e., better line of sight RF communication) of the tag to a receiver. The individual 250 is equipped with sensor 253a, which is an eye dilation sensor positioned in glasses proximate to the individual's eyes; sensor 253b, which is a hydration sensor configured to monitor sweat loss or sweat loss rate and positioned in a body suit or shirt proximate to the individual's back; sensor 253c, which is a sensor for measuring contextual data, such an accelerometer for measuring acceleration, ambient temperature sensor or like for measuring outside temperature, humidity, barometric pressure, wind speed, air quality or composition, or the like and which is positioned in a shirt collar proximate to the individual's neck; sensor 253d, which is a blood pressure monitor positioned on an arm band proximate to the individual's arm; and sensor 253e, which is a blood chemistry sensor configured for monitoring levels of one or more of carbon dioxide, oxygen, potassium, calcium, sodium, hematocrit, temperature and pH and positioned on an arm band proximate to the individual's arm.

The depicted individual 250 is further equipped with a power supply 255 positioned on a belt proximate to the individual's waist. The depicted power supply may be disposed in electrical communication (perhaps through wires sewn into clothing, etc.) with the tag and/or sensors 253a-e to provide primary or back-up power to such devices. In other embodiments (such as that shown in FIG. 2A), each of the tags and sensors may include their own power supply (e.g., battery). In one embodiment, each tag includes a battery while each of the sensors draws power from a common power supply (not shown).

While FIGS. 2A and 2B depict a particular type of individual, namely, athletes, various other types of individuals are contemplated in connection with the embodiments herein described. As will be apparent to one of ordinary skill in the art in view of this disclosure, each individual may be equipped with a different array of tags and sensors. For example, and without limitation, were the selected individual a race car for motor sports applications, such individual may be equipped with a tag positioned proximate to the car's roof, a fuel sensor positioned proximate a fuel tank, a temperature sensor, an RPM sensor, etc., positioned within the car's engine compartment, and a brake sensor positioned proximate to the car's brake system.

In various embodiments (including those shown in FIGS. 2A and 2B), each sensor may include a transmitter for transmitting a sensor signal comprising, for example, a sensor information packet to one or more receivers (such as receivers 106 of FIG. 1). The sensor information packet may include, but is not limited to, a sensor unique identification number (sensor UID), other identification information, stored sensor data, one or more environmental measurements, or other desired information for object or personnel identification. The sensor information packet may include analog information, digital data, or both. In some embodiments, the sensor information packet may include a sensor-individual correlator that can be used to associate a specific individual with a specific sensor. In one embodiment, multiple sensors may share a common transmitter that buffers and transmits the sensor information packet from various sensors at regular intervals or, in alternate embodiments, when interrogated by a remote receiver.

In still other embodiments, one or more sensors may be disposed in wired or wireless communication with one or more tags and, thus, may leverage the transmitters of the one or more tags to package and relay the sensor information packet to one or more remote receivers. In an embodiment where a tag transmits the sensor information packet to one or more remote receivers, the tag may incorporate the sensor information packet into the tag-data packet, such that the transmitted tag-data packet may include both the sensor information packet and tag data elements. In some embodiments, the transmitted tag-data packet may include a tag-sensor correlator that can be used to associate a specific sensor with a specific tag.

As may be appreciated by one skilled in the art in view of this disclosure, the one or more sensors may be configured specifically for attachment to an individual as a worn sensor. For example, one or more sensors may be sewn or woven into fabric. For a participant in a sporting event, that fabric could be part of a uniform or referee outfit. For an individual in a sausage race, the sensor could be attached to the lederhosen or sombrero portion of the sausage costume. For a fan, the sensor might be worn as a wristband or nametag. In another embodiment, one or more sensors may be inserted under a layer of skin or swallowed. In another example embodiment, one or more sensors may be part of a computing application or large medical diagnostic device that the individual patient sits by or lays next to in order to provide physical data.

The one or more sensors may be powered wirelessly by an RF interrogator or may be powered by a dedicated battery or capacitor mounted within or proximate to the sensor itself. In another embodiment, power may be provided by wire or wirelessly by a location tag, a separate power source worn on the athlete's body, or by environmental activity, such as solar power, kinetic energy, shock, or motion. In another embodiment, power may be provided from a wall outlet. In an embodiment in which power is not internal to the sensor or provided wirelessly, power may be carried to the sensor over the skin, via a cable, or via a woven fabric.

As will be apparent to one of ordinary skill in the art in view of this disclosure, once the tags and sensors of FIGS. 2A and 2B are positioned on individuals, they may, in some embodiments, be correlated to such individuals. For example, in some embodiments, unique tag or sensor identifiers (unique IDs such as tag UIDs or sensor UIDs) may be correlated to an individual profile (e.g., John Smith—80 year old male patient, Fred Johnson—28 year old triathlete, Cinco—chorizo costume with sombrero, or ID 027—race car number 27) and stored to a remote database accessible to the receiver processing and analytics system as discussed in greater detail below. Each individual profile may further include or be correlated with a variety of data including, but not limited to, biometric data (e.g., height, weight, health data, etc.), ambient sensor data, and other data that may be apparent to one of skill in the art in view of the foregoing description. In some embodiments, the tags or sensors may be associated with an individual before they are positioned on an individual, such as when a nametag is printed or when a RF locating tag is placed on shoulder pads which will likely be worn by a particular athlete.

Tag ID and Sensor Data Transmission Architecture

FIGS. 3A, 3B, 3C, 3D, and 3E show block diagrams of various different architectures that may be utilized in transmitting signals from one or more tags and sensors to one or more receivers of a receiver processing and analytics system in accordance with embodiments of the invention. In some embodiments, the depicted architectures may be used in connection with the receiver processing and analytics system 110 of FIG. 1. More than one of these architectures may be used together in a single system.

FIG. 3A shows a RF location tag 102, such as that shown in FIG. 1, which may be configured to transmit a tag signal to one or more receivers 106. The one or more receivers 106 may transmit a receiver signal to the receiver hub/locate engine 108.

The depicted RF location tag 102 may generate or store a tag UID and/or tag data as shown. The tag data may include useful information such as the installed firmware version, last tag maintenance date, configuration information, and/or a tag-individual correlator. The tag-individual correlator may comprise data that indicates that a monitored individual is associated with the RF location tag 102 (e.g., name, uniform number and team, biometric data, tag position on individual, i.e., right wrist). As will be apparent to one of skill in the art in view of this disclosure, the tag-individual correlator may be stored to the RF location tag 102 when the tag is registered or otherwise associated with an individual. While shown as a separate field for illustration purposes, one of ordinary skill in the art may readily appreciate that the tag-individual correlator may be part of any tag data or even omitted from the tag.

The tag signal data transmitted from RF location tag 102 to receiver 106 may include "blink data" as it is transmitted at selected intervals. This "blink rate" may be set by the tag designer or the system designer to meet application requirements. In some embodiments, the blink rate is consistent for one or all tags and, in other embodiments, the blink rate may data dependent (i.e., change based on the data transmitted). Blink data includes characteristics of the tag signal that allow the tag signal to be recognized by the receiver 106 so the location of the RF location tag 102 may be determined by the locating system. Blink data may also comprise one or more tag data packets. Such tag data packets may include any data from the tag 102 that is intended for transmission such as, for example in the depicted embodiment, a tag UID, tag data, and a tag-individual correlator. In the case of TDOA systems, the blink data may be or include a specific pattern, code, or trigger that the receiver 106 (or downstream receiver processing and analytics system) detects to identify that the transmission is from a RF location tag 102 (e.g., a UWB tag).

The depicted receiver 106 receives the tag signal, which includes blink data and tag data packets as discussed above. In one embodiment, the receiver 106 may pass the received tag signal directly to the receive hub/locate engine 108 as part of its receiver signal. In another embodiment, the receiver 106 could perform some basic processing on the received tag signal. For instance, the receiver could extract blink data from the tag signal and transmit the blink data to the receive hub/locate engine 108. The receiver could transmit a time measurement to the receive hub/locate engine 108 such as a TOA measurement and/or a TDOA measurement. The time measurement could be based on a clock time generated or calculated in the receiver, it could be based on a receiver offset value as explained above, it could be based on a system time, and/or it could be based on the time difference of arrival between the tag signal of the RF location tag 102 and the tag signal of a RF reference tag (e.g., tag 104 of FIG. 1). The receiver 106 could additionally or alternatively determine a signal measurement from the tag signal (such as a received signal strength indication (RSSI), a direction of signal, signal polarity, or signal phase) and transmit the signal measurement to the receive hub/locate engine 108.

FIG. 3B shows a RF location tag 202 and sensor 203, such as those worn on an individual's person as shown in FIG. 2, which may be configured to transmit tag signals and sensor signals, respectively, to one or more receivers 106, 166. The one or more receivers 106, 166 may then transmit receiver signals to the receiver hub/locate engine 108. One or more receivers 106, 166 may share physical components, such as a housing or antenna.

The depicted RF location tag 202 may comprise a tag UID and tag data (such as a tag-individual correlator) and transmit a tag signal comprising blink data as discussed in connection with FIG. 3A above. The depicted sensor 203 may generate and/or store a sensor UID, additional stored sensor data (e.g., a sensor-individual correlator, sensor type, sensor firmware version, last maintenance date, the units in which environmental measurements are transmitted, etc.), and environmental measurements. The "additional stored sensor data" of the sensor 203 may include any data that is intended for transmission, including but not limited to a RF location tag 202, a reference tag (e.g., 104 of FIG. 1), a sensor receiver, a receiver 106, and/or the receiver/hub locate engine 108.

The sensor-individual correlator may comprise data that indicates that a monitored individual is associated with the sensor 203 (e.g., name, uniform number and team, biometric data, sensor position on individual, i.e., right wrist). As will be apparent to one of skill in the art in view of this disclosure, the sensor-individual correlator may be stored to the sensor 203 when the sensor is registered or otherwise associated with an individual. While shown as a separate field for illustration purposes, one of ordinary skill in the art may readily appreciate that the sensor-individual correlator may be part of any additional stored sensor data or omitted from the sensor altogether.

Sensors such as sensor 203 that are structured according to embodiments of the invention may sense or determine one or more environmental conditions (e.g. temperature, pressure, pulse, heartbeat, rotation, velocity, acceleration, radiation, position, chemical concentration, voltage) and store or transmit "environmental measurements" that are indicative of such conditions. To clarify, the term "environmental measurements" includes measurements concerning the environment proximate the sensor including, without limitation, ambient information (e.g., temperature, position, humidity, etc.) and information concerning an individual's health, fitness, operation, and/or performance. Environmental measurements may be stored or transmitted in either analog or digital form and may be transmitted as individual measurements, as a set of individual measurements, and/or as summary statistics. For example, temperature in degrees Celsius may be transmitted as {31}, or as {33, 32, 27, 22, 20, 23, 27, 30, 34, 31}, or as {27.9}. In some embodiments, the sensor-individual correlator could be determined at least in part from the environmental measurements.

In the depicted embodiment, RF location tag 202 transmits a tag signal to receiver 106 and sensor 203 transmits a sensor signal to sensor receiver 166. The sensor signal may comprise one or more sensor information packets. Such sensor information packets may include any data or information from the sensor 203 that is intended for transmission such as, for example in the depicted embodiment, sensor UID, additional stored sensor data, sensor-individual correlator, and environmental measurements. A receiver signal from receiver 106 and a sensor receiver signal from sensor receiver 166 may be transmitted via wired or wireless communication to receiver hub/locate engine 108 as shown.

FIG. 3C depicts a sensor 203 communicating through a RF location tag 202 in accordance with various embodiments. In one embodiment, the sensor 203 may be part of (i.e., reside in the same housing or assembly structure) of the RF location tag 202. In another embodiment, the sensor 203 may be distinct from (i.e., not resident in the same housing or assembly structure) the RF location tag 202 but configured to communicate wirelessly or via wired communication with the RF location tag 202.

In one embodiment, the RF location tag 202, the sensor 203, or both, may generate and/or store a tag-sensor correlator that indicates an association between a RF location tag 202 and a sensor 203 (e.g., tag UID/sensor UID, distance from tag to sensor in a particular stance, set of sensors associated with a set of tags, sensor types associated with a tag, etc.). In the depicted embodiment, both the RF location tag 202 and the sensor 203 store the tag-sensor correlator.

In the depicted embodiment, sensor 203 transmits a sensor signal to RF location tag 202. The sensor signal may comprise one or more sensor information packets as discussed above. The sensor information packets may comprise the sensor UID, a sensor-individual correlator, additional stored sensor data, the tag-sensor correlator, and/or the environmental measurements. The RF location tag 202 may store some portion or some or all of the sensor information packets locally and may package the sensor information packets into one or more tag data packets for transmission to receiver 106 as part of a tag signal or simply pass them along as part of its tag signal.

FIG. 3D illustrates an example communication structure for a reference tag 104 (e.g., reference tag 104 of FIG. 1), an RF location tag 202, a sensor 203, and two receivers 106 in accordance with one embodiment. The depicted reference tag 104 is a RF location tag and thus may include tag data, a tag UID, and/or the like and is capable of transmitting tag data packets. In some embodiments, the reference tag 104 may form part of a sensor and may thus be capable of transmitting sensor information packets.

The depicted sensor 203 transmits a sensor signal to RF reference tag 104. The RF reference tag 104 may store some portion or some or all of the sensor information packets locally and may package the sensor information packets into one or more tag data packets for transmission to receiver 106 as part of a tag signal, or simply pass them along as part of its tag signal.

As was described above in connection with FIG. 1, the receivers 106 of FIG. 3D are configured to receive tag signals from the RF location tag 202 and the reference tag 104. Each of these tag signals may include blink data, which may comprise tag UIDs, tag data packets, and/or sensor information packets. The receivers 106 each transmit receiver signals via wired or wireless communication to the receiver hub/locate engine 108 as shown.

FIG. 3E illustrates an example communication structure between an RF location tag 202, a plurality of receivers 106, and a variety of sensor types including, without limitation, a sensor 203, a diagnostic device 233, a triangulation positioner 243, a proximity positioner 253, and a proximity label 263 in accordance with various embodiments. In the depicted embodiment, none of the sensors 203, 233, 243, 253 form part of an RF location tag 202 or reference tag 104. However, each may comprise a sensor UID and additional stored sensor data. Each of the depicted sensors 203, 233, 243, 253 transmits sensor signals comprising sensor information packets.

In the depicted embodiment, receiver 106 is configured to receive a tag signal from RF location tag 202 and a sensor signal directly from sensor 203. In such embodiments, sensor 203 may be configured to communicate in a communication protocol that is common to RF location tag 202 as will be apparent to one of ordinary skill in the art in view of this disclosure.

FIG. 3E depicts one type of sensor referred to herein as a "proximity interrogator". The proximity interrogator 223 can include circuitry operative to generate a magnetic, electromagnetic, or other field that is detectable by a RF location tag 202. While not shown in FIG. 3E, a proximity interrogator 223 may include a sensor UID and other sensor data or information as discussed above.

In some embodiments, the proximity interrogator 223 is operative as a proximity communication device that can trigger a RF location tag 202 (e.g., when the RF location tag 202 detects the field produced by the proximity interrogator 223) to transmit blink data under an alternate blink pattern or blink rate. The RF location tag can initiate a preprogrammed (and typically faster) blink rate to allow more location points for tracking an individual. In some embodiments, the RF location tag may not transmit a tag signal until triggered by the proximity interrogator 223. In some embodiments the RF location tag 202 may be triggered when the RF location tag 202 moves near (e.g., within communication proximity to) a proximity interrogator 223. In some embodiments, the RF location tag may be triggered when the proximity interrogator 223 moves near to the RF location tag 202. In other embodiments, the RF location tag 202 may be triggered when a button is pressed or a switch is activated on the proximity interrogator 223 or on the RF location tag itself. For example, a proximity interrogator 223 could be placed at the start line of a racetrack. Every time a car passes the start line, a car-mounted RF location tag 202 senses the signal from the proximity interrogator and is triggered to transmit a tag signal indicating that a lap has been completed. As another example, a proximity interrogator 223 could be placed at a Gatorade cooler. Each time an athlete fills a cup from the cooler an athlete-mounted RF location tag 202 senses the signal from the proximity interrogator and is triggered to transmit a tag signal indicating that Gatorade has been consumed. As another example, a proximity interrogator 223 could be placed on a medical cart. When paramedics use the medical cart to pick up an athlete and move her to the locker room, an athlete-mounted RF location tag 202 senses the signal from the proximity interrogator and is triggered to transmit a tag signal indicating that they have been removed from the game. As explained, any of these post-triggered tag signals may differ from pre-triggered tag signals in terms of any aspect of the analog and/or digital attributes of the transmitted tag signal.

FIG. 3E depicts another type of sensor that is generally not worn by an individual but is referred to herein as a "diagnostic device". However, like other sensors, diagnostic devices may measure one or more environmental conditions and store corresponding environmental measurements in analog or digital form.

While the depicted diagnostic device 233 is not worn by an individual, it may generate and store a sensor-individual correlator for association with environmental measurements taken in connection with a specific individual. For example, in one embodiment, the diagnostic device 233 may be a blood pressure meter that is configured to store as environmental measurements blood pressure data for various individuals. Each set of environmental measurements (e.g., blood pressure data) may be stored and associated with a sensor-individual correlator.

The depicted diagnostic device 233 is configured to transmit a sensor signal comprising sensor information packets to a sensor receiver 166. The sensor information packets may comprise one or more of the sensor UID, the additional stored data, the environmental measurements, and/or the sensor-individual correlator as discussed above. The sensor receiver 166 may associate some or all of the data from the sensor information packets with other stored data in the sensor receiver 166 or with data stored or received from other sensors, diagnostic devices, RF location tags 102, or reference tags. The sensor receiver 166 transmits a sensor receiver signal to a receiver hub/locate engine 108.

Another type of sensor shown in FIG. 3E is a triangulation positioner 243. A "triangulation positioner" is a type of sensor that senses position. The depicted triangulation positioner 243 includes a sensor UID, additional stored sensor data, and environmental measurements as discussed above.

In some embodiments, a triangulation positioner (also known as a global positioning system (GPS) receiver) receives clock data transmitted by one or more geostationary satellites (a satellite in a known or knowable position) and/or one or more ground based transmitters (also in known or knowable positions), compares the received clock data, and computes a "position calculation". The position calculation may be included in one or more sensor information packets as environmental measurements.

In another embodiment, a triangulation positioner comprises one or more cameras or image-analyzers that receive emitted or reflected light or heat, and then analyzes the received images to determine the location of an individual or sensor. Although a triangulation positioner may transmit data wirelessly, it is not a RF location tag because it does not transmit blink data or a tag signal that can be used by a receiver hub/locate engine 108 to calculate location. In contrast, a triangulation positioner senses position and computes a position calculation that may then be used as environmental measurements by the receiver hub/locate engine 108.

In one embodiment, a triangulation positioner could be combined with a RF location tag or reference tag (not shown). In such embodiments, the triangulation positioner could compute and transmit its position calculation via the RF location tag to one or more receivers. However, the receiver hub/locate engine would calculate tag location based on the blink data received as part of the tag signal and not based solely on the position calculation. The position calculation would be considered as environmental measurements and may be included in associated sensor information packets.

As will be apparent to one of ordinary skill in the art, position calculations (e.g., GPS receiver position calculations) are not as accurate as the location calculations (e.g., UWB waveform based location calculations) performed by receiver hub/locate engines structured in accordance with various embodiments of the invention. That is not to say that position calculations may not be improved using known techniques. For example, a number of influences, including atmospheric conditions, can cause GPS accuracy to vary over time. One way to control this is to use a differential global positioning system (DGPS) comprising one or a network of stationary triangulation positioners that are placed in a known position, and the coordinates of the known position are stored in memory as additional stored sensor data. These triangulation positioners receive clock data from geostationary satellites, determine a position calculation, and broadcast a difference between the position calculation and the stored coordinates. This DGPS correction signal can be used to correct for these influences and significantly reduce location estimate error. Exemplary use of DGPS correction may be found in commonly owned U.S. Pat. No. 7,755,541, which is hereby incorporated by reference herein in its entirety.

Another type of sensor shown in FIG. 3E is a proximity detector 253. A "proximity detector" is a type of sensor that senses identity within an area (e.g., a local area) that is small with respect to the monitored area 100 of FIG. 1. Many different ways of sensing identity (e.g., a unique ID or other identifier for a sensed object or individual) would be apparent to one of ordinary skill in the art in view of this disclosure including, without limitation, reading a linear bar code, reading a two-dimensional bar code, reading a near field communication (NFC) tag, reading a RFID tag such as a UHF tag, HF tag, or low frequency tag, an optical character recognition device, a biometric scanner, or a facial recognition system.

In some embodiments, a proximity detector senses an attribute of an individual (or an individual's wristband, tag, label, card, badge, clothing, uniform, costume, phone, ticket, etc.). The identity sensed by a proximity detector may be stored locally at the proximity detector 253 as shown and transmitted as environmental measurements via one or more sensor information packets to a sensor receiver 166.

In some embodiments, a proximity detector 253 may have a defined position, which is often stationary, and may be associated with a location in the monitored area 100 of FIG. 1. For example, a proximity detector 253 could be located at a finish line of a race track, an entrance gate of a stadium, with a diagnostic device, at a goal line or goal post of a football field, at a base or home plate of a baseball diamond, or a similar fixed location. In such embodiments where the proximity detector is stationary, the position coordinates of the proximity detector and a sensor UID could be stored to a monitored area database (not shown) that is accessible by one or more of the receivers 106, 166, the receiver hub/locate engine 108, and/or other components of the receiver processing and analytics system 110. In embodiments where the proximity detector is movable, a position calculation could be determined with a triangulation positioner, or the proximity detector could be combined with a RF location tag and located by the receiver hub/locate engine 108. While shown as separate fields for illustration purposes in FIG. 3E, identify information and position calculation could comprise part of the additional stored sensor data, the environmental measurements, or both.

In one embodiment, the proximity detector could be associated with a reference tag (e.g., tag 104 of FIG. 1) whose position is recorded in the monitored area database. In other embodiments, the proximity detector is movable, such that it may be transported to where it is needed. For example, a proximity detector 253 could be located on a medical cart, first down marker, a diagnostic device, go kart, forklift, or carried by a paramedic or security guard. In an embodiment where the proximity detector 253 is movable it would typically be associated with a RF location tag or triangulation positioner so that location (for a RF location tag) or position (for a triangulation positioner) can be determined at the time identity is sensed.

In the embodiment where the proximity detector includes a RF location tag, the receiver hub/locate engine 108 would locate the associated RF location tag, and the tag data/sensor data filter 112 would associate the tag location data for the associated RF location tag as the position of the proximity detector, while determining the identity of an associated individual from any received sensor information packets. In the alternate embodiment where the proximity detector includes a triangulation positioner, the triangulation positioner would compute a position calculation that could be stored as additional stored sensor data and/or environmental measurements, and transmitted as one or more sensor information packets. In one embodiment, sensor information packets for a proximity detector may include both sensed identity information and a position calculation.

Another type of sensor shown in FIG. 3E is a proximity label 263. A proximity label has a fixed position and an identification code (e.g., a sensor UID). The proximity label 263 may further comprise additional stored sensor data as shown. The depicted proximity label 263 is configured to be read by proximity detector 253. In some embodiments, proximity detector 253 may be further configured to write information to proximity label 263.

A proximity label 263 may be a sticker, card, tag, passive RFID tag, active RFID tag, NFC tag, ticket, metal plate, electronic display, electronic paper, inked surface, sundial, or otherwise visible or machine readable identification device as is known in the art. The coordinates of the position of the proximity label 263 are stored such that they are accessible to the receive hub/locate engine 108. For example, in one embodiment, the position coordinates of a proximity label 263 could be stored in a field database or monitored area database accessible via a network, or stored locally as additional stored data in the proximity detector 253.

In some embodiments, a position of the proximity label 263 is encoded into the proximity label 263 itself. For example, coordinates of a position of the proximity label 263 could be encoded into a passive RFID tag that is placed in that position. As another example, the coordinates of a position of the proximity label 263 could be encoded into a printed barcode that is placed in that position. As another example, a proximity label 263 comprising a NFC tag could be encoded with the location "end zone", and the NFC tag could be placed at or near an end zone at Bank of America stadium. In some embodiments, the stored coordinates of the proximity label 263 may be offset from the actual coordinates of the proximity label 263 by a known or determinable amount.

In one embodiment, a proximity label 263 such as an NFC tag may be encoded with a position. When a sensor such as a proximity detector approaches the NFC tag it may read the position, then transmit the position in a sensor information packet to the sensor receiver 166' and eventually to the receiver hub/locate engine 108. In another embodiment, a proximity label 263 such as a barcode label may be encoded with an identification code. When a smartphone with a proximity detector (such as a barcode imager) and a triangulation positioner (such as a GPS chip, GPS application, or similar device) approaches the barcode label it may read the identification code from the barcode, determine a position calculation from received clock data, then transmit the identity and the position calculation to sensor receiver 166' and eventually to the receiver hub/locate engine 108 as part of one or more sensor information packets.

In the depicted embodiment, triangulation positioner 243 and proximity detector 253 are each configured to transmit sensor signals carrying sensor information packets to sensor receiver 166'. The depicted sensors 243, 253, like any sensor discussed herein, may transmit sensor signals via wired or wireless communication protocols. For example, any proprietary or standard wireless protocol (e.g., 802.11, Zigbee, ISO/IEC 802.15.4, ISO/IEC 18000, IrDA, Bluetooth, CDMA, or any other protocol) could be used for the sensor signals. Alternatively or additionally, any standard or proprietary wired communication protocol (e.g., Ethernet, Parallel, Serial, RS-232, RS-422, USB, Firewire, $I^2C$, etc.) may be used. Similarly, sensor receiver 166', and any receiver discussed herein, may use similar wired and wireless protocols to transmit receiver signals to the receiver hub/locate engine.

In one embodiment, upon receiving sensor signals from the triangulation positioner 243 and the proximity detector 253, the sensor receiver 166' may associate some or all of the data from the received sensor information packets with other data stored to the sensor receiver 166', or with data stored or received from other sensors (e.g., sensor 203), diagnostic devices 233, RF location tags 102, or RF reference tags 104. Such associated data is referred to herein as "associated sensor data". In the depicted embodiment, the sensor receiver 166' is configured to transmit some or all of the received sensor information packets and any associated sensor data to the receiver hub/locate engine 108 at part of a sensor receiver signal.

In one embodiment, a smartphone comprising a proximity detector (such as a barcode imager) and a triangulation positioner (such as a GPS chip) may associate an identification code determined from a barcode with a position calculation from received clock data as associated sensor data and transmit a sensor information packet that includes such associated sensor data to the receiver hub/locate engine 108. In another embodiment, the smartphone could transmit a first sensor information packet including the identification code and the smartphone's unique identifier to another sensor receiver, the smartphone could transmit a second sensor information packet including the position calculation and the smartphone's unique identifier to the sensor receiver, and the sensor receiver could associate the position calculation with the identification code based on the common smartphone unique identifier and transmit such associated sensor data to the receiver hub/locate engine 108. In another embodiment, the sensor receiver could determine a first time measurement associated with the first sensor information packet and a second time measurement associated with the second sensor information packet that, in conjunction with the sensor UID, could be used, by the receiver hub/locate engine 108, to associate the first sensor information packet with the second sensor information packet.

In one embodiment, the receiver hub/locate engine 108 receives receiver signals from the receiver 106 and sensor receiver signals from the sensor receivers 166, 166'. In the depicted embodiment, receiver 106 may receive blink data from the RF location tag 102 and transmits to the receiver hub/locate engine 108 some or all of the blink data, perhaps with additional time measurements or signal measurements. In some embodiments, time measurements or signal measurements may be based on a tag signal received from a RF reference tag (e.g., reference tag 104 of FIG. 1). The receiver hub/locate engine 108 collects the blink data, time measurements (e.g. time of arrival, time difference of arrival, phase), and/or signal measurements (e. g. signal strength, signal direction, signal polarization, signal phase) from the receivers 106 and computes tag location data for the tags 102 as discussed above in connection with FIG. 1. In some embodiments, the receivers 106 may be configured with appropriate RF filters, such as to filter out potentially interfering signals or reflections proximate the field of play or other area to be monitored.

The receiver hub/locate engine 108 may also access stored data or clock data from local storage and from a network location. The receiver hub/locate engine 108 uses this information to determine tag location data for each RF location tag. It may also associate data derived or extracted from tag signals transmitted from one or more RF location tags with information or data derived or extracted from sensor signals transmitted from one or more sensors.

In addition to the TOA or TDOA systems previously described, other real-time location systems (RTLS) such as received signal strength indication based systems could potentially be implemented by a receiver hub/locate engine 108. Any RTLS system using RF location tags, including those described herein, could require considerable processing by the receiver hub/locate engine 108 to determine the tag location data from the blink data received from the tags. These may require time measurement and/or signal measurement in addition to blink data, which preferably includes a tag UID. In contrast, in other systems, such as global position systems (GPS) systems, location data is determined based upon the position calculation transmitted from a GPS transmitter (also referred to as a GPS receiver or GPS tag) which includes calculated information about the location where the tag was positioned (i.e., coordinates determined at the tag via satellite signal triangulation, etc.) when the position calculation was determined or stored. Thus, GPS information typically refers to additional information that is transmitted along with a GPS transmitter ID before the transmission is received by a sensor receiver.

A GPS host device or back-end server may receive the GPS information and simply parse the position calculation (as opposed to calculating the position information at the host device) and the GPS transmitter ID into a data record. This data record may be used as a GPS position calculation, or it could be converted to a different coordinate system to be used as a GPS position calculation, or it could be processed further with DGPS information to be used as a GPS position calculation.

Returning to FIG. 3C, the depicted RF location tag 202 is used to convey (sometimes called backhaul) sensor information packets to a receiver 106. In some embodiments, while not shown, multiple sensors 203 may transmit sensor signals carrying sensor information packets to RF location tag 202. Such received sensor information packets may be associated with blink data that is transmitted to receiver 106.

In one embodiment, the receiver hub/locate engine 108 may parse sensor information packets from received tag data packets and associate such sensor information packets with the RF location tag 202 that transmitted the sensor information packet. Thus, the receiver hub/locate engine 108 may be able to determine tag location data, which may comprise a location and other data (e.g., tag data, tag UID, tag-individual correlator, sensor-individual correlator, additional stored sensor data, environmental measurements, tag-sensor correlator, identity information, position calculation, etc.) from one or more tags or sensors. Such data and information may be transmitted to the receiver processing and analytics system 110.

In some embodiments, once the receiver hub/locate engine 108 determines a location estimate of a RF location tag 102 at the time epoch of the tag signal, the receiver hub/locate engine 108 can also associate a location estimate with the tag data packet included in the blink data of such tag signal. In some embodiments, the location estimate of the tag signal may be used as tag location data for the tag data packet. In some embodiments a Geographical Information System (GIS) may be used by the receive hub/locate engine 108 to refine a location estimate, or to map a location estimate in one coordinate system to a location estimate in a different coordinate system, to provide a location estimate for the tag data packet. In some embodiments the Geographical Information System may include a known location for one or more RF reference tags identifiable by a tag unique identification number.

In one embodiment, the location estimated for the tag data packet may be associated with any data in the tag data packet, including a tag UID, other tag data, and, if included, one or more sensor information packets, including sensor UID, additional stored sensor data, and environmental measurements. Since environmental measurements may include a position calculation from a triangulation positioner (e.g., a GPS device), the receiver hub/locate engine 108 could parse the position calculation and use it to refine a location estimate for the tag data packet.

Preferably, the receiver hub/locate engine 108 may access an individual database to determine tag-individual correlators or sensor-individual correlators. Individual data (e.g., an individual profile) may be stored in a server, in tag memory, in sensor memory, or in other storage accessible via a network or communication system, including tag data or additional stored sensor data as explained previously.

In some embodiments, by comparing data accessed using a sensor-individual correlator, the receiver hub/locate engine 108 may associate an individual with a sensor information packet received from a sensor, and/or may associate an individual with such sensor. Because the receiver hub/locate engine 108 may associate a sensor position estimate with a sensor information packet, the receiver hub/locate engine 108 may also estimate an individual position for the associated individual.

In another embodiment, by comparing data accessed using a tag-sensor correlator, the receiver hub/locate engine 108 may associate a sensor with a tag data packet received from a RF location tag 102. Because the receiver hub/locate engine 108 may associate a location estimate with a tag data packet, the receiver hub/locate engine 108 may also create a sensor location estimate for the associated sensor. By comparing a location estimate for a RF location tag with a sensor location estimate or a sensor position estimate, the receiver hub/locate engine 108 may associate a RF location tag with a sensor, or may associate a tag data packet with a sensor information packet. The receiver hub/locate engine 108 could also determine a new or refined tag-sensor correlator based on this association.

In still another embodiment, by comparing a location estimate for a RF location tag with an individual location estimate or an individual position estimate, the receiver hub/locate engine 108 may associate a RF location tag with an individual, or may associate a tag data packet with an individual. The receiver hub/locate engine 108 could also determine a new or refined tag-individual correlator based on this association.

In one embodiment, by comparing a location estimate for a sensor with an individual location estimate or an individual position estimate, the receiver hub/locate engine 108 may associate a sensor with an individual, or may associate a sensor information packet with an individual. The receiver hub/locate engine 108 could also determine a new or refined sensor-individual correlator based on this association.

Data derived or extracted from tag signals transmitted from one or more RF location tags is referred to herein as "tag derived data" and shall include, without limitation, tag data, tag UID, tag-individual correlator, tag-sensor correlator, tag data packets, blink data, time measurements (e.g. time of arrival, time difference of arrival, phase), signal measurements (e.g., signal strength, signal direction, signal polarization, signal phase) and tag location data (e.g., including tag location estimates). Information or data derived or extracted from sensor signals transmitted from one or more sensors is referred to herein as "sensor derived data" and shall include, without limitation, sensor UID, additional stored sensor data, sensor-individual correlator, environmental measurements, sensor information packets, position calculations (including sensor position estimates), position information, identity information, tag-sensor correlator, and associated sensor data. Data derived or extracted from stored individual data is referred to herein as "individual profile information" and shall include, without limitation, tag-individual correlator, sensor-individual correlator, identity information, name, uniform number and team, biometric data, tag position on individual. In various embodiments, the receiver hub/locate engine 108 may transmit tag derived data, sensor derived data, individual profile information, various combinations thereof, and/or any information from the GIS, the field database, the monitored area database, and the individual database to the receiver processing and analytics system 110.

Receiver Processing and Analytics System

Figure 4A:
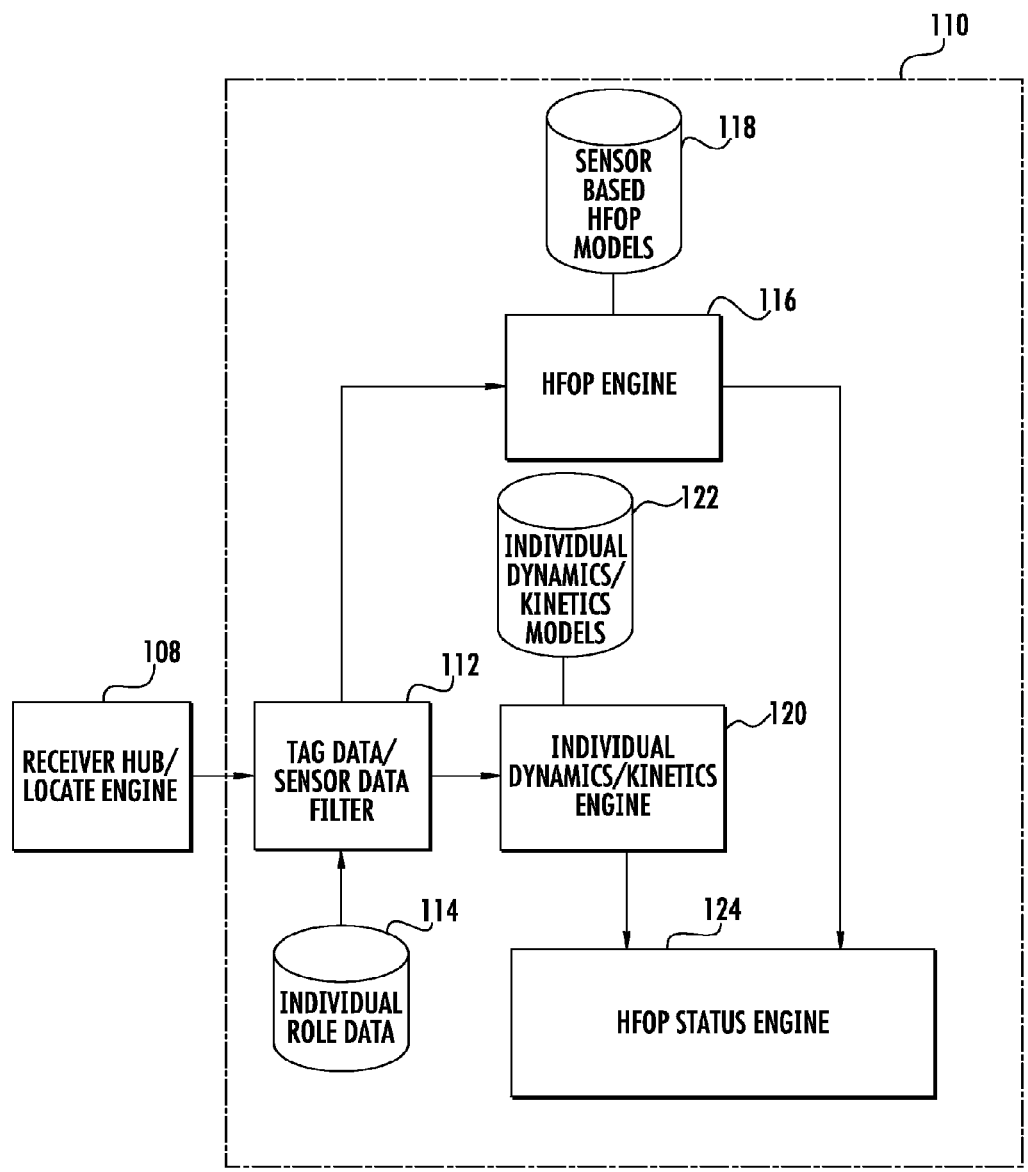
FIGS. 4A and 4B are block diagrams of receiver processing and analytics systems that are configured to monitor the health, fitness, operation, and performance of individuals in accordance with example embodiments.
Figure 4B:
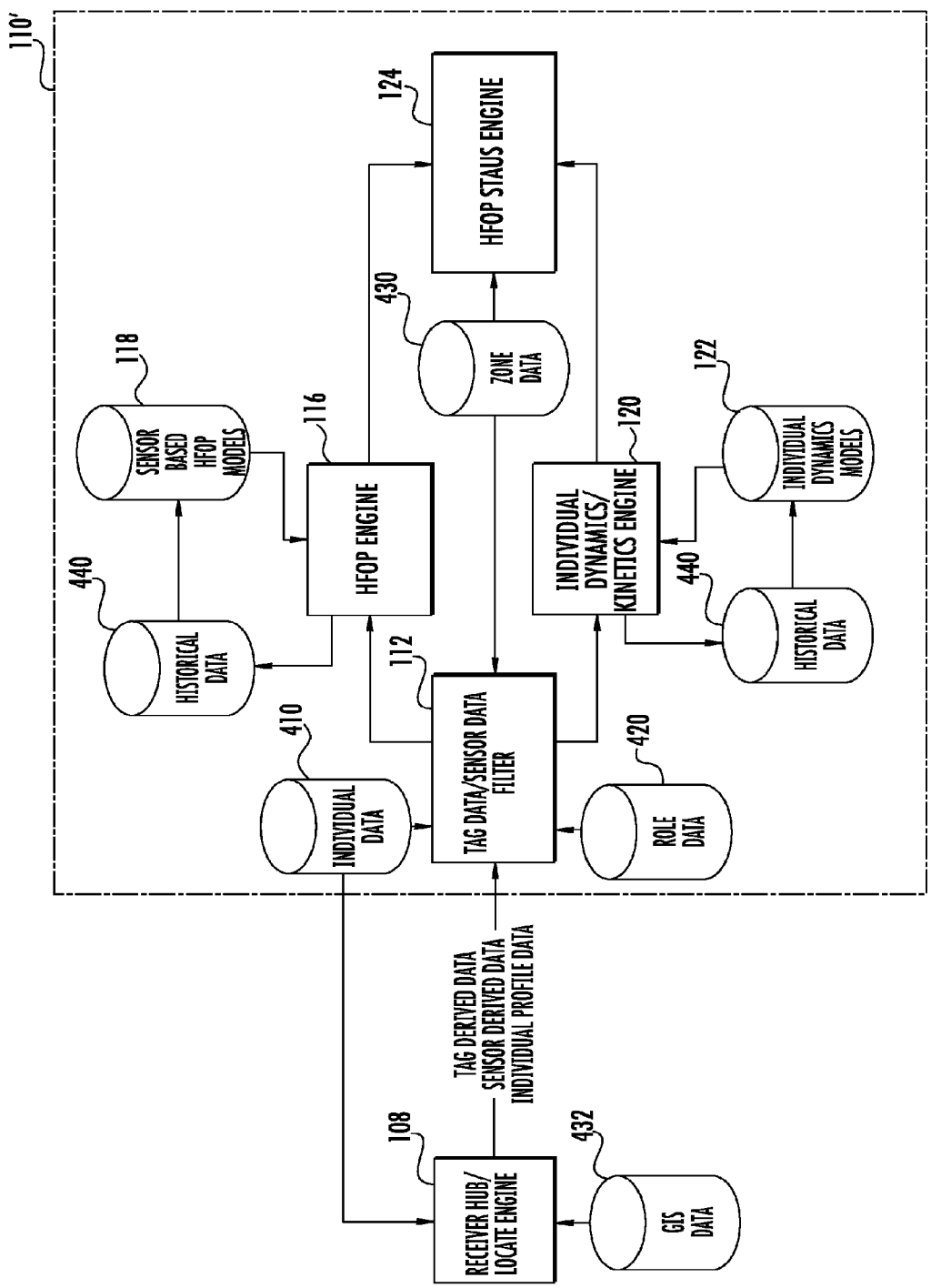

FIGS. 4A and 4B are block diagrams of two systems that may be specifically configured in accordance with an example embodiment of the present invention. As shown in FIG. 4A, receiver hub/locate engine 108 may be configured to access or receive receiver signals comprising tag derived data and sensor derived data from one or more receivers. In one example embodiment, the receiver hub/locate engine 108 may access or provide a data transmission link to each of one or more receivers in succession and download, for example, a plurality of TOA measurements, blink data, and sensor derived data having been buffered in the receiver since the receiver hub/locate engine 108 last accessed the data.

Receiver hub/location engine 108 may further be configured to provide tag location data and/or sensor derived data and/or individual profile information to the receiver processing and analytics system 110. The receiver processing and analytics system 110 may include a tag data/sensor data filter 112 configured for receiving the tag location data and sensor derived data and individual profile information from the receiver hub 108.

The tag data/sensor data filter 112 may be configured for associating tag derived data (including tag location data) and sensor derived data to a particular individual, filtering tag derived data from sensor derived data, and routing the tag location data and the sensor derived data to an individual dynamics/kinetics engine 120 and an HFOP engine 116, respectively.

The tag data/sensor filter 112 accesses an individual role database 114 to identify historical or contextual information related to the individual and/or role data for the individual (e.g., data indicating that a first individual is a particular football player in football game application, data indicating that a second individual is a particular patient in a hospital application, data indicating that a third individual is a race car in a motor sports application, etc.) In another embodiment, historical information related to the health, fitness, operation and/or performance of an individual may be provided by the individual role database 114. For example, a medical history may be provided for a particular individual by the individual role database 114.

The individual role database 114 may be populated with information (e.g., tag-individual correlators, sensor-individual correlators, tag-sensor correlators, etc.) that allows the tag data/sensor filter 112 to determine whether location tags and sensors are to be associated with or correlated to a particular individual. In one embodiment, the location tags and/or sensors comprise a unique identifier (e.g., tag UID, sensor UID) that is transmitted to the receiver hub/locate engine 108 and passed to the tag data/sensor data filter 112. That tag data/sensor data filter 112 uses the unique identifiers to correlate the tag and sensor derived data to individual profiles (e.g., individual data) stored to the individual role database 114. In another embodiment, the individual role database 114 is configured to associate the sensors and/or sensor derived data with a particular individual, which will be described in FIGS. 12A-12C.

The individual role database 114 may further include role information associated with individuals, location tags, and/or sensors. For example, particular individuals may be associated with a particular role (e.g., John Doe/quarterback).

The tag data/sensor data filter 112 may then be configured to filter tag derived data (including tag location data) from sensor derived data and provide sensor derived data to a health, fitness, operation and performance engine 116 (HFOP engine 116) and provide tag derived data to an individual dynamics/kinetics engine 120.

The HFOP engine 116 may be configured to receive sensor derived data from the tag data/sensor data filter 112. In one embodiment, the HFOP engine 116 may be further configured to receive historical or contextual information related to the individual and/or a role of the individual. The HFOP engine 116 may further be configured to access a sensor based HFOP models database 118. The sensor based HFOP models database 118 may be populated with historical sensor derived data related to individuals (e.g., a baseline snapshot of individual health parameters suggesting an individual is healthy, sick, injured, or the like). The historical data may be generated from capturing sensor derived data from an individual equipped with sensors. The sensor based HFOP models database 118 may, additionally or alternatively, be populated manually or programmatically populated with health related data from patient studies, machine diagnostics studies, and the like.

In one embodiment, historical information related to the health, fitness, operation and/or performance of a particular individual may be provided by the HFOP models database 118. That is, the HFOP models database 118 may include at least one of health history data, fitness history data, operation level history data, or performance level history data for an individual. The health history data, fitness history data, operation level history data, or performance level history data for the individual may be manually input (e.g., inputting that a particular individual has hypertension) or may be acquired by prior monitoring, thus capturing tag derived data and/or sensor derived data from a previous monitoring session.

In some embodiments, the HFOP engine 116 may aggregate data related to one or more sensors for a particular individual over a period of time (e.g., heart rate data for one play for a football player in a football game, sweat rate data for a runner during a race, blood pressure data for an elderly patient on a walk, etc.). Using the historical and contextual data related to the individual and/or role of the individual, the HFOP engine 116 may further be configured to access the sensor based HFOP models database 118 and determine a list of probable HFOP statuses. For example, high heart rate data for a football player during a play may indicate that the player currently engaged in a high level of exertion (e.g., HFOP status 1) or perhaps is experiencing the onset of a stroke (e.g., HFOP status 2). The HFOP engine 116 uses other sensor derived data from other sensors to determine whether HFOP status 1 is more or less probable than HFOP status 2. Such information is fed to the HFOP status engine 124 as discussed in greater detail below.

In one embodiment, the HFOP engine 116 may be configured to output one or more probable outcomes or alternative selected data of interest. In another embodiment, the HFOP engine 116 may also be configured to output the aggregated sensor derived data, the historical and contextual data related to the individual and/or the role of the individual related to one or more probable outcomes or selected data of interest. In still another embodiment, the HFOP engine 116 may be configured to output various health parameters for the individual per unit time.

The individual dynamics/kinetics engine 120 may be configured to receive tag derived data (including tag location data) from the tag data/sensor data filter 112. In one embodiment, the individual dynamics/kinetics engine 120 may further be configured to receive historical or contextual information related to the individual and/or a role of the individual. The individual dynamics/kinetics engine 120 may further be configured to access an individual dynamics/kinetics models database 122.

The individual dynamics/kinetics engine 120 may compare the tag location data and individual role data to individual dynamics/kinetics models to determine aspects of the individual dynamics or movement kinetics. The dynamics/kinetics model database 122 may comprise models of different aspects or dimensions that may be based on past tag location data (e.g., tags fixed to various appendages of a monitored individual) or other data generated by a model generation engine or other tools. The models may include, without limitation, models for a particular individual profile (e.g., John Smith), an individual type (e.g., quarterback, a horse, a stock car, etc.), and the like. Such models may consider all three dimensions (x, y, z) of the tag location data for each tag (e.g., 202 of FIG. 2A) and may further consider different tag position arrays (e.g., two tag implementations—one proximate each shoulder, eleven tag implementations—one proximate each shoulder, one proximate each elbow, one proximate each hand, one proximate each knee, one proximate each foot, and one proximate to the head, etc.).

The individual dynamics/kinetics models database 122 may be populated with actual tag data drawn from particular actions (e.g., running on a track, running in a soccer game, walking, throwing, running, limping, falling, spraining an ankle or the like). The historical data may be generated from capturing data from an individual equipped with location tags or sensors, performing actions and storing the data with the associated action. The individual dynamics/kinetics models database 122 may, additionally or alternatively, be populated with average or aggregate data that may indicate particular actions. In another embodiment, position history data, such as historical information related to the dynamic and/or kinetic information of a particular individual (e.g., John Smith), may be stored and provided by the individual dynamics/kinetics models database 122.

In one embodiment, the individual dynamics/kinetics engine 120 determines a multi-dimensional individual location per unit time (e.g., individual location data) for each individual based on the tag location data, the individual role data, and the individual dynamics/kinetics models. Such multi-dimensional individual location data may include (1) relative position of the individual relative to a monitored area (e.g., a field of play, race track, etc.), (2) general orientation of the individual (e.g., standing, squatting, laying the ground, sitting, etc.), and (3) a specific orientation of the individual and/or various appendages of the individual (e.g., preparing to pass, in a three-point stance, in a ball-carrying position, in a tackling position, negotiating a turn, etc.).

The individual dynamics/kinetics engine 120 uses the real time tag location data stream from the tag data/sensor data filter 112, as well as the individual role data, to provide accurate information about what a particular individual is doing in real time. In some embodiments, the individual dynamics/kinetics engine 120 may further use sensor derived data, received from the tag data/sensor data filter 112 in the depicted embodiment, to aid in determining not only where the individual is, but also how that individual's location is changing with time, velocity, acceleration, deceleration, orientation, or the like. For example, in one embodiment, the sensor derived data may comprise accelerometer data that may indicate that an individual (or portion of an individual) is accelerating or decelerating. The individual dynamics/kinetics engine 120 outputs multi-dimensional individual location data per unit time.

The HFOP engine 116 and the individual dynamics/kinetics engine 120 are each configured to output data streams to a health, fitness, operation and performance (HFOP) status engine 124. The HFOP status engine 124 is configured to receive the ranked list of probable HFOP statuses from the HFOP engine 116 and the multi-dimensional individual location data from the individual dynamics/kinetics engine 120 and determine health, fitness, operation, or performance statuses for the individual. For example, in one embodiment, the HFOP status engine 124 may determine that the football player having the high heart rate discussed above is likely experiencing the onset of a stroke because the received multi-dimensional individual location data suggests the player is sitting on a bench and has not recently undertaken a high level of physical exertion. In such an embodiment, the HFOP status engine 124 may be configured to send an alert to medical staff.

In some embodiments, the HFOP status engine 124 may further be configured to receive location data, sensor derived data, and historical or contextual data related to the individual and/or role of the individual related to the location data and associated probable actions. Such information may be used to establish a baseline of health, fitness, operation, or performance for a given individual that may be stored as part of the individual's profile data. In some embodiments, such baseline may include a baseline of health, fitness, operation, or performance parameters.

In some embodiments, the HFOP status engine 124 may be configured to determine a status (e.g., healthy, sick, injured, hurt, active, not active, powered down, etc.) by comparing real time (or near real time) data concerning an individual's health, fitness, operation, or performance parameters to a stored snapshot or pre-determined threshold.

In one embodiment, the HFOP status engine 124 may be configured for determining a HFOP status for the individual based on the comparing the tag derived data to individual dynamics/kinetics models and based on comparing the sensor derived data to at least one of health models, fitness models, operation level models, or performance level models. In one embodiment, HFOP status may be determined based on whether particular sensor derived data satisfies particular threshold values related to health, fitness, operation and/or performance models. HFOP status may additionally or alternatively be based on whether particular multi-dimensional individual location data satisfies particular threshold values (e.g., perhaps values based on an individual's baseline snapshot or generally published data regarding movements or positions of a "healthy" individual of a certain age) related to dynamics and/or kinetic information. As one skilled in the art would understand, satisfying a threshold may include exceeding a threshold in some embodiments (e.g., blood pressure may exceed "healthy" threshold) or may include falling below a threshold for some embodiments (e.g., sweat rate may fall below "healthy" rate indicating possible dehydration).

In one embodiment, the HFOP status engine 124 may be configured to associate the determined status and/or action with another type of data (e.g., associating each play that a player appears in with the player). In one embodiment, the HFOP status engine 124 may be configured to monitor, store or track one or more individuals, one or more of health, fitness, operation, or performance of an individual or individuals, and/or one or more zones or location systems for an individual. In another embodiment, the HFOP status engine 124 may be configured to monitor a location system for a pre-defined event, unexpected, and/or an abnormal event. An event may be a particular action in a given context or associated with particular sensor derived data.

In some embodiments, the HFOP status engine 124 may be configured to cause an alert in response to a determination of a pre-defined event (e.g., a stroke, an injury, etc.), unexpected event, and/or abnormal event. In another embodiment, an alert may be sent upon determining whether the determined HFOP status satisfies a threshold value. In some embodiments, particular tag derived data and/or sensor derived data may trigger an alert, and thus bypass a status determination (e.g., heart rate approaching zero, or 'flat lining'). In another embodiment, the HFOP status engine 124 may be configured for sending a message or action related information to a parent, trainer, doctor, nurse, paramedic or the like.

Determining a status (e.g., an HFOP status) can be done in many ways. A sensor-based HFOP model database or an individual dynamics kinetics model database can be used to collect various models. A model may have multiple attributes that are represented by data fields. As one skilled in the art of databases would understand, a particular model may be selected by choosing one or more fields of interest that correspond with field values known from the tag derived data and/or the sensor derived data and/or individual role data. By comparing the fields of interest with the known field values, a status can be determined.

One way to determine compare the fields of interest with the known field values is to match the field of interest to the known field value.

A second way to compare the fields of interest with the known field values is to develop a control chart. A control chart uses a known or estimated distribution of values from a population of observations for the field of interest to determine an average (mean) value and a standard deviation. The model designer may set the mean and standard deviation based on the field of interest, or on a calculated value related to the field of interest, such as the differential between the field of interest and a standard multi-variable regression model estimate based on the field of interest. Two control limits are established, an upper control limit at three standard deviations more than the mean, and a lower control limit at three standard deviations less than the mean (i.e., a number other than three may be chosen by the model designer). As known field values are determined, each can be added to the control chart. If an observation exceeds the control limits (either higher than the upper control limit or lower than the lower control limit) the status can be deemed to have changed. Also, if individual field values continue to increase or decrease at least seven (or another value chosen by the model designer) times, the data is said to be trending and the status can be deemed to have changed.

A third way to compare the fields of interest with the known field values is to cluster the values from a population of observations for the field of interest. Various clustering algorithms are known in the art, including incremental clustering algorithms, divide-and-conquer based clustering algorithms, data sampling and summarization techniques, Euclidean distance based clustering algorithms, and kernel clustering algorithms. This may have the benefit of significantly reducing the data storage required, as a very large number of observations can be characterized by a smaller number of multi-variable clusters. By comparing known field values to variables for each cluster, a probability that tag location data is the same status as other observations in that cluster can be determined.

A fourth way to compare the fields of interest with the known field values is to calculate a covariance between past observations for the field of interest and current observations for the known field values (e.g., tag derived data, sensor derived data, and/or identity/role data). If the covariance is above a threshold value (such as 0.97) the status can be matched to the selected model.

In some embodiments, if the status is changed such that an event is identified by the HFOP status engine 124 an alert may be generated. In some embodiments, if the status changes from an undetermined status to a determined status then an event may be indicated by the HFOP engine as an alert.

FIG. 4B shows another embodiment of a system that may be specifically configured in accordance with an example embodiment of the present invention. As many of the components are identical or similar to above described embodiments, repetition of the description of such components will be omitted.

In the depicted embodiment, receiver hub/locate engine 108 receives receiver signals and outputs tag derived data (including tag location data) and sensor derived data to a tag data/sensor data filter 112 of a receiver processing and analytics system 110' structured in accordance with one embodiment.

While in certain embodiments, the receiver hub/location engine 108 is configured to correlate tag location data to tag UID and optionally sensor UID, in the depicted embodiment, the tag data/sensor data filter 112 may be configured to perform one or more additional correlations or associations. For example, the tag data/sensor data filter 112 may be configured to associate the tag UID with an individual (e.g., Jane Smith), the tag UID with a role, the tag location data with an individual or role, and the like.

FIGS. 5A-5E show example embodiments of individual, role, and performance associations. FIG. 5A depicts a correlation of tag UIDs to individuals. In particular, tag UIDs 1-4 are correlated to individual names (e.g., Jim, Ed, and Andy). Notably, as discussed above, in some embodiments individuals may receive multiple tags and thus Ed is correlated to tags 2 and 3. As will be apparent to one of skill in the art, tag UIDs need not be correlated to actual names (i.e., alphanumeric characters) and may be correlated to unique identifiers that are themselves correlated to individuals. In some embodiments, sensor UIDs (not shown) may be similarly correlated to individuals. In some embodiments, one or more addresses or sets of instructions may be used to access tag UID and sensor UID correlations of the type shown in FIG. 5A. Such addresses and instructions may be referred to as tag-individual correlators and sensor-individual correlators.

In one embodiment, the tag data/sensor data filter 112 may associate an individual (e.g., an individual name, unique identifier, etc.) with the tag UID while also associating sensor derived data with the tag UID. In still other embodiments, the tag data/sensor data filter 112 may use a registration database to associate a tag UID with an individual.

In some embodiments, in order to monitor the health or fitness of an individual, which may be associated with a tag UID as shown in FIG. 5A, measured performance may be compared with anticipated performance. As described above, performance may be generally described as a vector of measurements or attributes, e.g., Attribute A, Attribute B, and Attribute C.

FIG. 5B depicts a correlation between individual and performance. For example, an actual or average performance by an individual in connection with Attributes A, B, and C may be correlated to each individual as shown. Additionally or alternatively, in another embodiment, such actual or average performance may be correlated to a role as shown in FIG. 5D. A typical or average performance may also be correlated to individual and to role as shown in FIG. 5E. Finally, an individual may be correlated to one or more roles as shown in FIG. 5C. To support such correlations, the tag data/sensor data filter 112 may be configured to access one or both of an individual database 410 and a role database 420, which are illustrated in FIG. 4B.

Figure 6A:
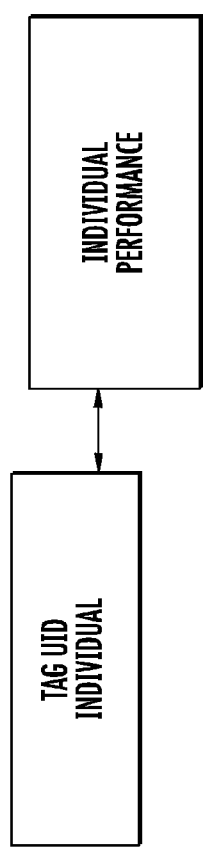
FIGS. 6A-6C are block diagrams showing data associations that may be used in accordance with an example embodiment.
Figure 6B:
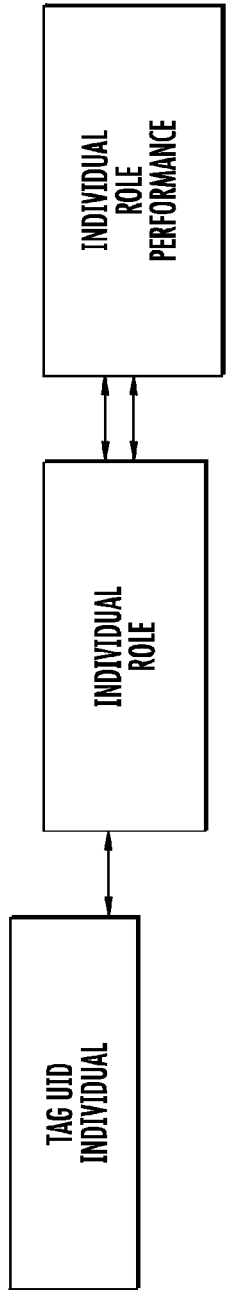
Figure 6C:
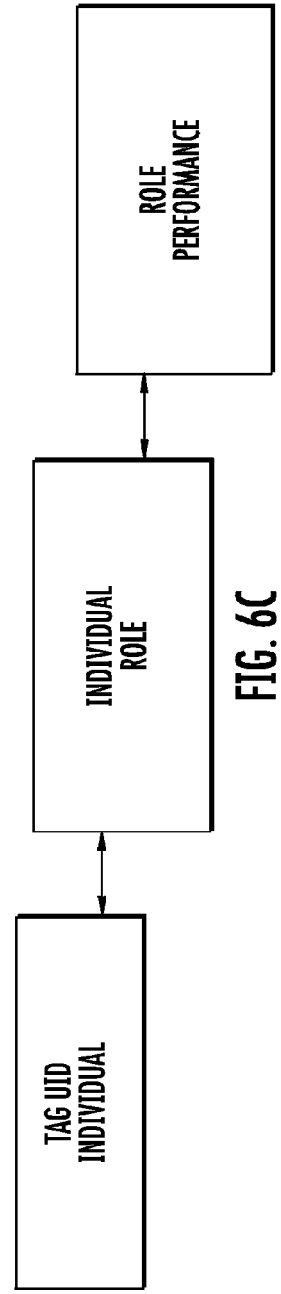

FIGS. 6A-6C show example embodiments for correlating tag UID, individual data, role data, and performance data. FIG. 6A illustrates how individual data (e.g., an individual identifier, name, etc.) may be used to correlate a tag UID to performance data. FIG. 6B illustrates how individual data (e.g., an individual identifier) may be used to correlate tag UID, role data, and performance data. FIG. 6C illustrates how individual data and role data may be used to correlate tag UID, and performance data.

Returning to FIG. 4B, the depicted tag data/sensor data filter 112 is configured to correlate tag derived data (including tag location data) and sensor derived data to individual data from individual database 410 and role data from role database 420. The tag data/sensor data filter 112 is configured, inter alia, to pass such correlated tag derived data, sensor derived data, individual data, and role date to the individual dynamics/kinetics engine 120.

In one embodiment, the individual dynamics/kinetics engine 120 is disposed in communication with historical data store 440 and individual dynamics/kinetics models database 122. The individual dynamics/kinetics models database 122 may be configured to store data related to an individual. For example, referring to the example above related to a human athlete individual who is standing, walking, or running, and where a tag is positioned at the individual's shoulder (e.g., tag 202a of FIG. 2A) and foot (e.g., tag 202g of FIG. 2A). The models database 122 may include a stature value of approximately four feet, which represents the distance or height between the shoulder and foot tags. Such stature value may be used by the system to identify, inter alia, when the individual is bent over, seated, etc. In another embodiment, the models database 122 may include a minimum stature value, e.g., 24 inches, which may represent a minimum distance or height expected between the shoulder and foot tags of even the shortest of individuals.

In one embodiment, the minimum stature value could vary by role (e.g., tagged football players may be expected to be taller than tagged horse racing jockeys, etc.). In another embodiment, the individual dynamics/kinetics engine 120 may calculate a stature value ($h_t$) at various times (t) by subtracting the height of tag 202g ($z_g$) from the height of tag 202a ($z_a$) (i.e., $h_t = z_a - z_g$) based on tag location data from the receiver hub/locate engine 108 and individual data from the tag data/sensor data filter 112. In an embodiment where individual data may be stored on the tag (e.g., 202a), the individual data may be forwarded through the receiver hub/locate engine 108 to the tag data/sensor data filter 112.

In one embodiment, the individual dynamics engine 120 may store the individual stature value $h_t$ as time series data in historical data store 440 or it could gather additional descriptive statistics such as a mode, median, standard deviation, number of observations for any or all of $h_t$, $z_a$ and $z_g$, and then store the descriptive statistics in historical data store 440. In one embodiment, time series data or descriptive statistics stored in historical data store 440 may include individual data or role data that may be used for additional context in building individual dynamic models as stored in the individual dynamics models database 122.

In one embodiment, during monitoring, the receiver hub/locate engine 108 may determine and collect tag derived data (including tag location information) and sensor derived data and provide such data to the tag data/sensor data filter 112. The tag data/sensor data filter 112 may access and/or utilize individual data from the individual data store 410 or role data from the role data store 420 before providing information to the individual dynamics engine 120.

In one embodiment, the individual dynamics engine 120 may be configured to calculate $h_T = z_{aT} - z_{gT}$ for a particular time T, and compare that to an expected value of h from the individual dynamics models 122. The results of the comparison are then provided to HFOP status engine 124, which may provide an alert to a coach, medic, parent or other appropriate personnel. In one embodiment, an alert may be provided if $z_{aT}$ is less than some small fraction of measured stature (e.g., the measured distance from the ground to a shoulder mounted tag) or if $z_{at}$ is less than some fraction of minimum stature (e.g., the expended or average distance from the ground to a shoulder mounted tag), suggesting that the athlete is crouched down or laying down. By considering $z_{aT} - z_{gT}$, in one embodiment, the system may determine that an individual is bent over or laying down, even if such individual is not on the ground.

In another embodiment, an alert may be provided if $h_T$ is less than some fraction of descriptive statistics such as the mode or median value of $h_t$ or $z_{at}$ for a selected individual or for a compilation of individuals with a similar role. In another embodiment, an alert may be provided if $h_t$ is less than the mean value of $h_t$ minus 3 times the standard deviation of $h_t$ suggesting that the recent value of $h_t$ differs from past observations more than would be expected from random measurement variation. In another embodiment, a control chart for h could be constructed based on historical values of $h_t$, and multiple observations of $h_T$ may be compared to the control chart. Using well-established methods of statistical process control, a trend of increasing $h_T$, decreasing $h_T$, or observations of $h_T$ beyond established control limits may be used to initiate an alert. Although the preceding examples have been used to describe various embodiments of the invention, it should be appreciated that one skilled in the art may utilize additional embodiments.

In some embodiments, the HFOP status engine 124 may be configured to access zone data from a zone data store 430 to determine whether or how to produce an alert. The term zone data as used herein refers to data or other information that might define one or more geographic or environmental areas, zones, or sectors. Such "zones" may or may not correlate to any real-world boundaries (e.g., a room may be divided into four zones regardless of whether any actual boundaries, i.e., partitions, walls, etc., exist in the room). In one embodiment, an individual may be located in one of multiple zones in an area monitored by a RTLS system, such as the system described with reference to FIG. 1. HFOP status engine 124 may be configured to utilize one or more rules for providing an alert depending on zone data. For example, a first rule may apply when an athlete is on the field of play (e.g., send an alert when the athlete is sitting for more than 15 seconds), which may differ from the rules for providing an alert when an athlete is on the sidelines or when an athlete is in the clubhouse.

In some embodiments, the tag data/sensor data filter 112 may use zone data from the zone data store 430 to determine whether the individual (or tag(s) associated with the individual) is positioned in a particular zone. The HFOP status engine 124 may use information about the zone stored in zone data store 430 in determining whether to produce an alert for any embodiment described herein.

As discussed in connection with FIG. 4A above, the tag data/sensor data filter 112 may be configured to filter tag derived data (including tag location data) from sensor derived data and provide sensor derived data to a health, fitness, operation and performance engine 116 (HFOP engine 116) and provide tag derived data (including tag location data) to an individual dynamics/kinetics engine 120.

In some embodiments, sensor derived data may additionally or alternatively be used as a determining factor by the HFOP status engine 124. For instance, as discussed above, the HFOP status engine sensor-based HFOP models 118 may be created and/or utilized to show that the typical body temperature for a human athlete individual is approximately 37 degrees Celsius. The model may be further refined (or one or more other models provided) based on data collected during a registration process. For example a model may be refined in which a body temperature is measured by a sensor (and transmitted as environment measurements) and later associated with the individual as individual data. In another embodiment, sensor derived data may be stored based on an individual's role, for example body temperature may be stored based on the athlete's role. In another embodiment, sensor derived data (e.g., body temperature) may be stored as historical time-series data or descriptive statistics data based on multiple sensor readings.

In one embodiment, during a monitoring process, a sensor (e.g., a GPS equipped smartphone having a barcode imaging application) may be capable of communicating both sensor derived data and a position calculation or position information as in FIG. 3E, or, a sensor (e.g., a thermometer) may be configured to communicate sensor derived data to which a tag is able to append tag derived data as discussed in connection with FIGS. 3C and 3D.

In one embodiment, the tag data/sensor data filter 112 may obtain tag derived data (including tag location data) and sensor derived data from the receiver hub/locate engine 108 or from a combination of the receiver hub/locate engine 108 and stored data accessed from the individual data store 410, the role data store 420, and the zone data store 430. In one embodiment, the tag data/sensor data filter 112 may provide sensor derived data (such as the temperature measured by a thermometer) to the HFOP engine 116 where it may be utilized in a comparison to sensor-based HFOP models accessed from the HFOP models database 118. In one embodiment, results of the comparison may then be provided to HFOP status engine 124, which may then provide an alert to a coach, medic, parent or other appropriate personnel.

In another embodiment, tag location data and the relative position of the applicable sensor or sensors (as may be determined based on the tag location data or sensor based position calculations or position information) may be used to determine if the athlete's temperature was measured orally, under the arm, or rectally. The sensor derived data and tag derived data (including tag location data) may be used by the HFOP engine 116 to compare to the measured temperature data to sensor-based HFOP models correlated to body temperature measurement position. The results of this comparison may then be provided to HFOP status engine 124, which may provide an alert.

Again, as discussed above, individual data such as Jim or Mary, role data such as water boy or running back, or zone data such as Lambeau Field or sauna may also be provided by the tag data/sensor data filter 112 to the HFOP engine 116 in order to add context to the sensor derived data, such as temperature measured by the thermometer.

In some embodiments, sensor derived data from sensors not associated with the individual (e.g., taken by sensors not mounted to the individual but still routed wired or wirelessly to the receiver hub/locate engine 108) may also be collected by the tag data/sensor data filter 112 and provided to the HFOP engine 116 and/or individual dynamics engine 120. For instance, an ambient temperature thermometer sensor could provide important context to determining an appropriate body temperature at the HFOP engine 116 or determining an appropriate amount of time spent by the water cooler to the individual dynamics engine 120.

Health, Fitness, Operation, and Performance Monitoring

FIGS. 7, 8, 9, 10, 11, 12A-12C, and 14 illustrate example flowcharts of the example operations performed by a method, apparatus and computer program product in accordance with an embodiment of the present invention. It will be understood that each block of the flowcharts, and combinations of blocks in the flowcharts, may be implemented by various means, such as hardware, firmware, processor, circuitry and/or other devices associated with execution of software including one or more computer program instructions.

Figure 15:
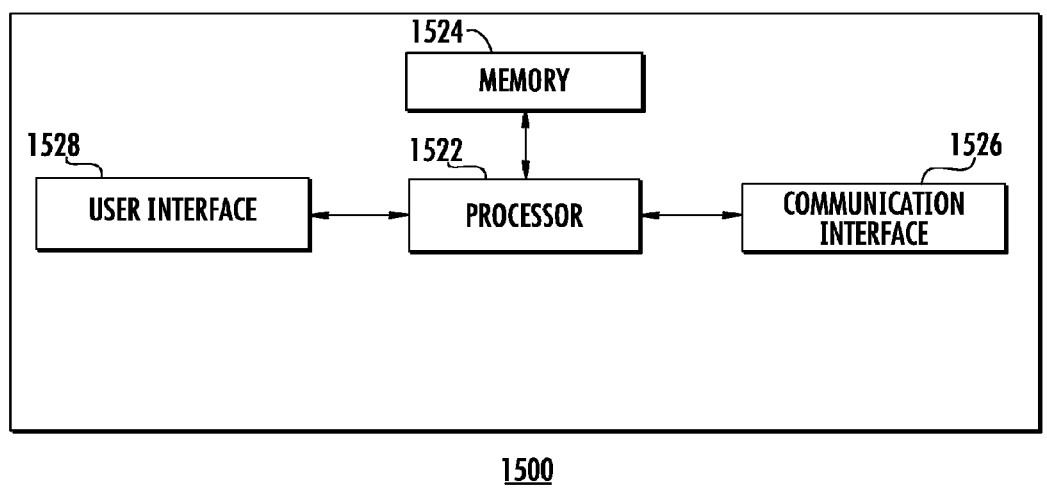
FIG. 15 is a block diagram of an apparatus that may be specifically configured in accordance with an example embodiment of the present invention.

For example, in reference to FIG. 15, one or more of the procedures described herein may be embodied by computer program instructions. In this regard, the computer program instructions which embody the procedures described above may be stored by a memory 1524 of an apparatus employing an embodiment of the present invention and executed by a processor 1522 in the apparatus.

As will be appreciated by one of ordinary skill in the art, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s).

As such, the operations of FIGS. 7, 8, 9, 10, 11, 12A-12C, and 14 when executed, convert a computer or processing circuitry into a particular machine configured to perform an example embodiment of the present invention. Accordingly, the operations of FIGS. 7, 8, 9, 10, 11, 12A-12C, and 14 define an algorithm for configuring a computer or processing to perform an example embodiment. In some cases, a general purpose computer may be provided with an instance of the processor which performs the algorithms of FIGS. 7, 8, 9, 10, 11, 12A-12C, and 14 to transform the general purpose computer into a particular machine configured to perform an example embodiment.

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

In some embodiments, certain ones of the operations herein may be modified or further amplified as described below. Moreover, in some embodiments additional optional operations may also be included. It should be appreciated that each of the modifications, optional additions or amplifications below may be included with the operations above either alone or in combination with any others among the features described herein.

Receiver Processing and Analytics System Processes

Figure 7:
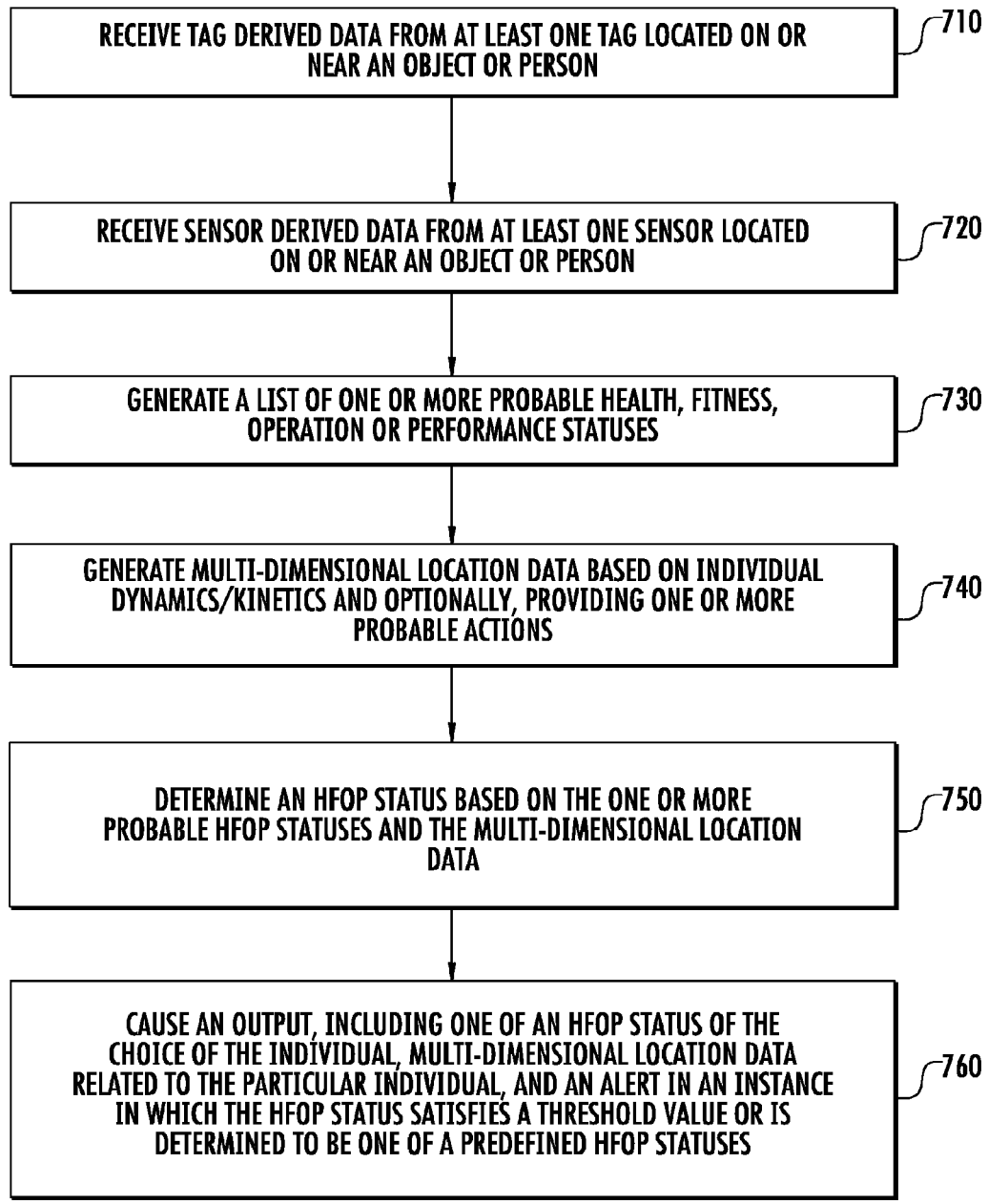
FIG. 7 is a flowchart illustrating a method for monitoring the health, fitness, operation, and performance of individuals in accordance with an example embodiment.

FIG. 7 shows an example method that may be executed by one or more machines (some examples of which are discussed in connection with FIGS. 1, 2, 4A, 4B, and 15) to monitor the health, fitness, operation, or performance of individuals, in accordance with some embodiments discussed herein.

As shown in block 710 of FIG. 7, an apparatus, such as a receiver processing and analytics system 110 or 110', may be configured for accessing, capturing, and/or receiving data from a receiver hub/locate engine. In one embodiment, tag derived data may be received from at least one location tag located on or near an object or individual. In yet another embodiment, tag derived data may be downloaded from a memory (e.g., hard drive, thumb drive or the like).

As shown in block 720 of FIG. 7, an apparatus, such as receiver processing and analytics system 110 or 110', may be configured for accessing, capturing, and/or receiving data from a receiver hub/locate engine 108. In one embodiment, sensor derived data may be received from at least one sensor located on or near an object or person. In yet another embodiment, sensor derived data may be downloaded from a memory (e.g., hard drive, thumb drive or the like).

As shown in block 730 of FIG. 7, an apparatus, such as receiver processing and analytics system 110 or 110' and/or, more specifically an HFOP engine, may be configured for determining a probable list of HFOP statuses related to a health, fitness, operation, and performance of individual or object based on associated sensor derived data. In one embodiment, historical and/or contextual information may be utilized. In another embodiment, sensor based health, fitness, operation, and/or performance models may be accessed and/or utilized in the determination. In one embodiment, one or more probable statuses related to the health, fitness, operation and/or performance of an individual may be determined.

As shown in block 740 of FIG. 7, an apparatus, such as receiver processing and analytics system 110 and/or, more specifically an individual dynamics/kinetics engine, may be configured to determine aspects of the individual dynamics or movement kinetics including, without limitation, individual location data. In one embodiment, the apparatus may be configured for determining at least one status related to individual dynamics or movement kinetics based on associated individual location data. In one embodiment, historical and/or contextual information may be utilized. In another embodiment, the dynamics/kinetics model database 122 may comprise models of different aspects or dimensions that may be utilized. In one embodiment, at least one probable status or a list of probable statuses related to the individual dynamics or movement kinetics of an individual may be determined.

As shown in block 750 of FIG. 7, an apparatus, such as receiver processing and analytics system 110 and/or, more specifically an HFOP status engine, may be configured for determining at least one status from a probable list of statuses based on at least one of an HFOP status (or probable list of HFOP statuses) related to a health, fitness, operation, and performance of an individual and a status (or probable list of statuses) related to individual dynamics or movement kinetics. In one embodiment, historical and/or contextual information may be utilized in the determination of a status.

As shown in block 760 of FIG. 7, an apparatus, such as receiver processing and analytics system 110 and/or, more specifically an HFOP status engine, maybe configured for causing an output. The output may include one of an HFOP status of an individual, multi-dimensional location data related to a particular individual, and an alert in an instance in which the HFOP status satisfies a threshold value or is determined to be one of a number of predefined HFOP statuses. For example, an output may include transmitting data to a processing system that displays action related data (e.g., a graphical user interface for tracking or monitoring one or more individuals).

In another embodiment, the apparatus may be configured for causing an alert in response to determining a presence of a particular status, such as for example, unexpected status, an abnormal status, or a pre-defined status (e.g., stroke, injury, etc.).

In one embodiment, that apparatus may be configured for sending a message and/or status related information to a parent, trainer, doctor, nurse, paramedic or the like. The message may indicate, for example, that help is requested and/or required. The message and/or information may comprise the location of the first individual. In another embodiment, the message or information may comprise information related to the abnormal or unexpected status, or the pre-defined status that was determined.

Tag Data/Sensor Data Filter Processing

Figure 8:
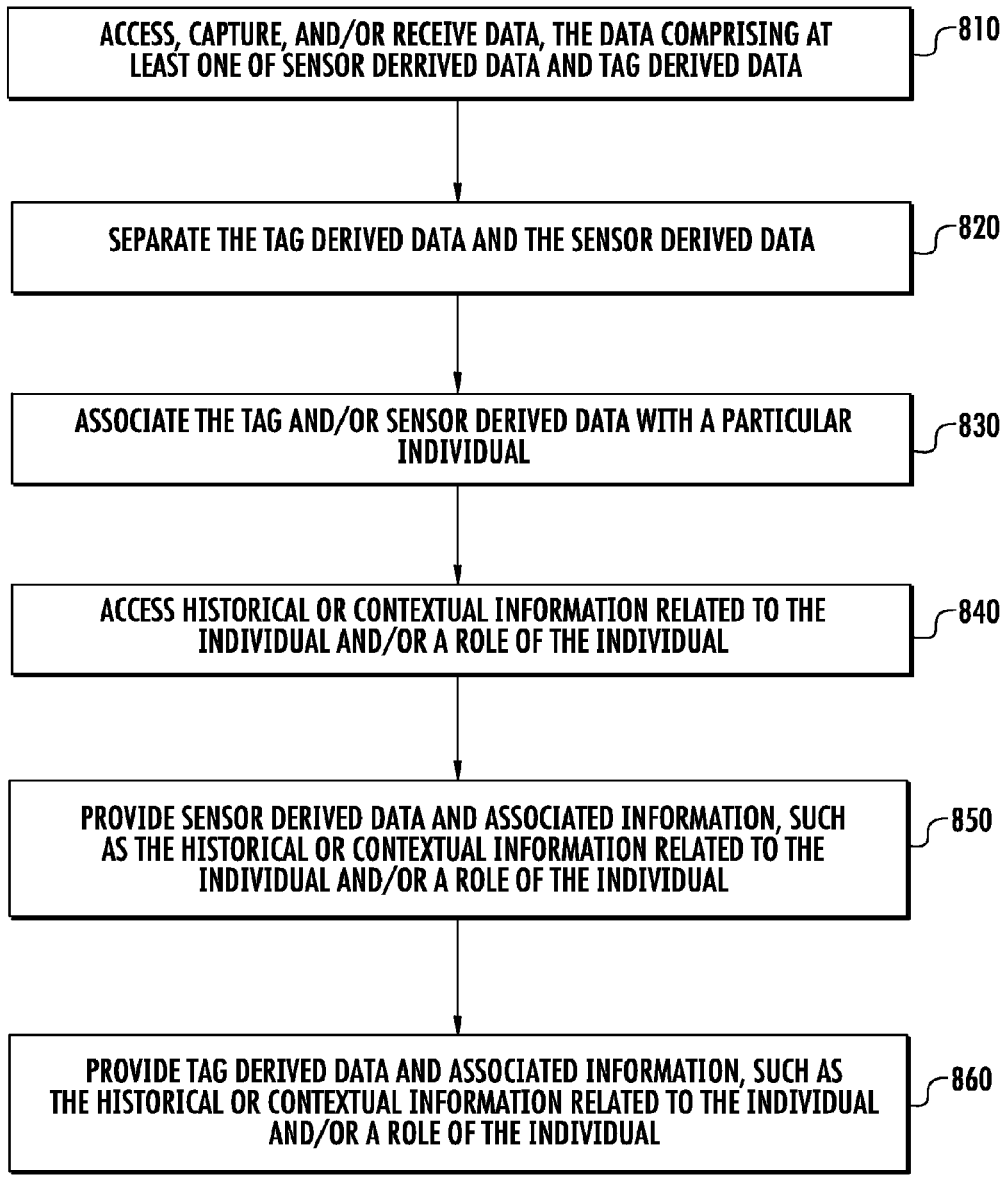
FIG. 8 is a flowchart illustrating a method for use in a tag data/sensor data filter in accordance with an example embodiment.

FIG. 8 shows an example method that may be executed by one or more machines (some examples of which are discussed in connection with FIGS. 1, 4A and 4B) to separate tag derived data and sensor derived data, associate such data with an individual and provide the data to the appropriate processing engine, in accordance with some embodiments discussed herein.

As shown in block 810 of FIG. 8, an apparatus, such as a tag data/sensor data filter 112 or receiver processing and analytics system 110 or 110', may be configured for accessing, capturing, and/or receiving data from a receiver hub/locate engine 108. In another embodiment, the data may be packetized data including one or both of tag derived data (including tag location data) and sensor derived data. The data may be associated with a capture time. In another embodiment, tag derived data and/or sensor derived data may be downloaded from a memory (e.g., hard drive, thumb drive or the like).

As shown in block 820 of FIG. 8, an apparatus, such as a tag data/sensor data filter 112 or receiver processing and analytics system 110 or 110', may be configured for separating the tag derived data (e.g., tag location data) and the sensor derived data.

As shown in block 830 of FIG. 8, an apparatus, such as a tag data/sensor data filter 112 or a sensor processing and distribution system 110 or 110', may be configured for associating the tag and/or sensor derived data with a particular individual.

The association may be performed by identifying an identifier (e.g., a tag-individual correlator, sensor-individual correlator, etc.) included in the packetized data associated with particular tag derived data and/or sensor derived data. The identifier may then be checked against individual identifier data by accessing an individual role database. The individual role database 114, as described earlier, may include data associating unique identifiers to particular individuals, and/or particular individuals to particular roles.

As shown in block 840 of FIG. 8, an apparatus, such as a tag data/sensor data filter 112 or receiver processing and analytics system 110 or 110', may be configured for accessing historical or contextual information related to the individual and/or a role of the individual.

As shown in block 850 of FIG. 8, an apparatus, such as a tag data/sensor data filter 112 or a sensor processing and distribution system 110 or 110', may be configured for providing sensor derived data and associated information, such as the historical or contextual information related to the individual and/or a role of the individual, to a HFOP engine 116.

As shown in block 860 of FIG. 8, an apparatus, such as a tag data/sensor data filter 112 or receiver processing and analytics system 110 or 110', may be configured for providing tag derived data and associated information, such as the historical or contextual information related to the individual and/or a role of the individual, to an individual dynamics/kinetics engine 120.

Health, Fitness, Operation, and Performance Engine Processing

Figure 9:
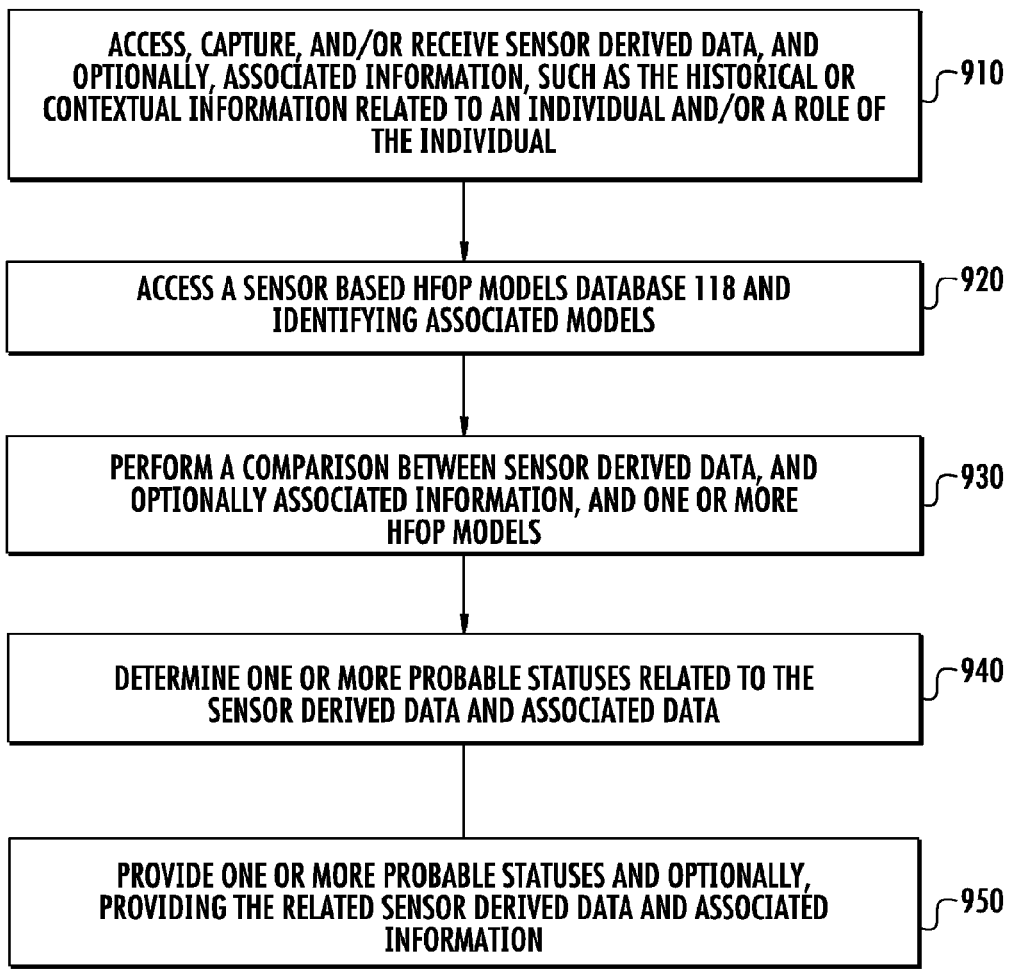
FIG. 9 is a flowchart illustrating a method for use in a health, fitness, operation and performance engine, in accordance with an example embodiment.

FIG. 9 shows an example method that may be executed by one or more machines (some examples of which are discussed in connection with FIGS. 1, 4A and 4B) to determine one or more probable actions associated with sensor derived data related to an individual, in accordance with some embodiments discussed herein.

As shown in block 910 of FIG. 9, an apparatus, such as a HFOP engine 116 or receiver processing and analytics system 110 or 110', may be configured for accessing, capturing, and/or receiving sensor derived data. In some embodiments, the apparatus may be configured for receiving sensor derived data, and associated information, such as the historical or contextual information related to an individual and/or a role of the individual.

As shown in block 920 of FIG. 9, an apparatus, such as a HFOP engine 116 or receiver processing and analytics system 110 or 110', may be configured for accessing a sensor based HFOP models database 118 and identifying associated models. As described earlier, the sensor based HFOP models database 118 may be populated with historical sensor derived data related to individuals (e.g., a baseline snapshot of individual health parameters suggesting an individual is healthy, sick, injured, or the like). HFOP models database 118 may include at least one of health history data, fitness history data, operation level history data, or performance level history data for an individual.

Identifying historical sensor derived data and/or associated models may be performed by comparing sensor derived data and associated information received from an individual to sensor derived data and associated information related to a historical sensor derived data and/or models comprising a combination of historical sensor derived data (e.g., heart rate, breathing rate etc. related to a stroke). In some circumstances, the comparison may yield a match with a particular model. In other circumstances, no precise match is identified but the comparison identifies one or more models most likely associated with the received sensor derived data and associated information (e.g., individual data, role data, etc.).

As shown in block 930 of FIG. 9, an apparatus, such as a HFOP engine 116 or receiver processing and analytics system 110 or 110', may be configured for performing a comparison between sensor derived data, and optionally associated information, and one or more HFOP models. The HFOP engine 116 may be configured to aggregate data related to one or more sensors for a particular individual over a period of time and utilize the aggregated data in the comparison.

As shown in block 940 of FIG. 9, an apparatus, such as a HFOP engine 116 or receiver processing and analytics system 110 or 110', may be configured for determining one or more probable statuses related to the sensor derived data and optionally, the associated data, based on the comparison of block 930.

As shown in block 950 of FIG. 9, an apparatus, such as a HFOP engine 116 or receiver processing and analytics system 110 or 110', may be configured for providing one or more probable statuses to a HFOP status engine 124. In some embodiments, one or more probable actions are provided in conjunction with the related sensor derived data and associated data.

Individual Dynamics/Kinetics Engine Processing

Figure 10:
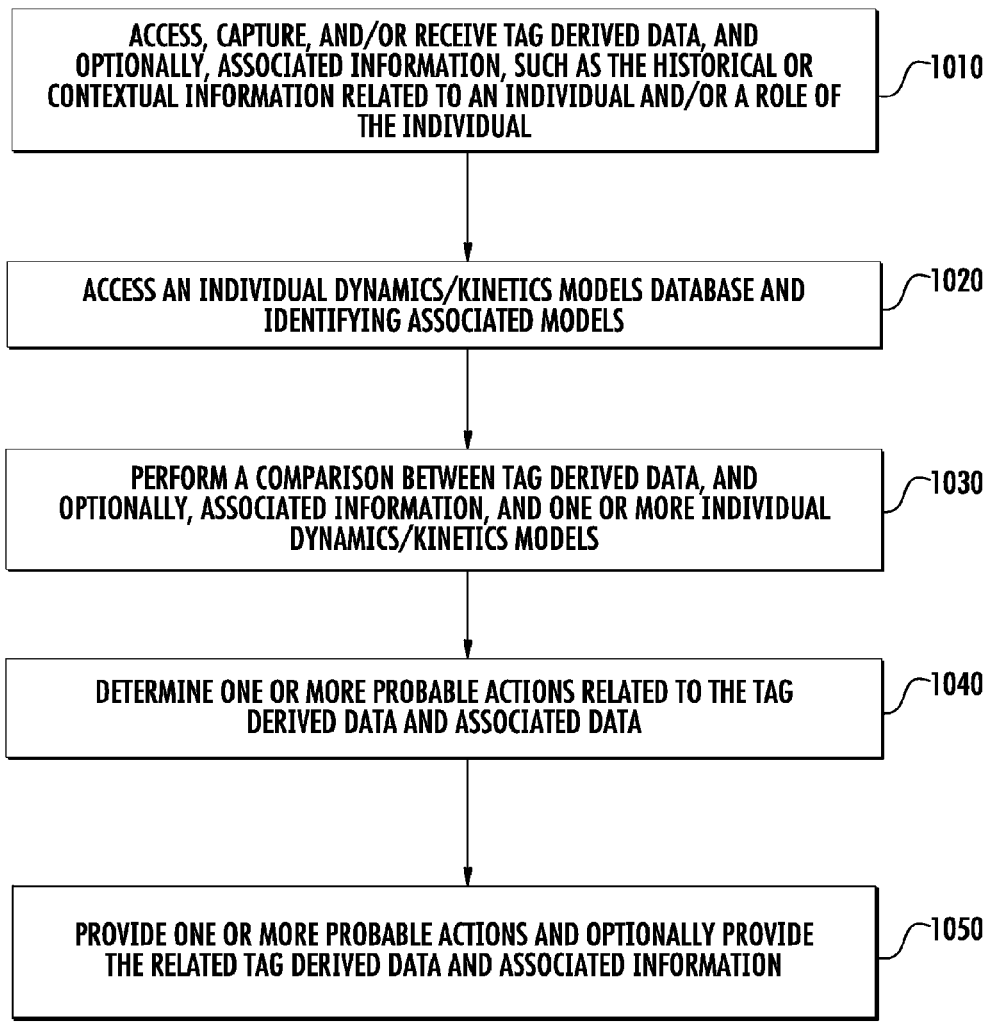
FIG. 10 is a flowchart illustrating a method for use in an individual dynamics/kinetics engine in accordance with an example embodiment.

FIG. 10 shows an example method that may be executed by one or more machines (some examples of which are discussed in connection with FIGS. 1 and 2) to provide multi-dimensional individual location information per unit time, in accordance with some embodiments discussed herein.

As shown in block 1010 of FIG. 10, an apparatus, such as an individual dynamics/kinetics engine 120 or receiver processing and analytics system 110 or 110', may be configured for accessing, capturing, and/or receiving tag derived data (including tag location data). In some embodiments, the apparatus may be configured for receiving tag derived data, and associated information, such as the historical or contextual information related to an individual and/or a role of the individual.

As shown in block 1020 of FIG. 10, an apparatus, such as an individual dynamics/kinetics engine 120 or receiver processing and analytics system 110 or 110', may be configured for accessing an individual dynamics/kinetics model database 122 and identifying aspects of the individual dynamics or movement kinetics and/or associated models.

Identifying associated models may be performed by comparing tag derived data and associated information received from an individual to tag derived data and associated information related to a model. While no model may be a match, the apparatus may be configured to identify similar models or those most closely associated with a particular individual, position, or role.

As shown in block 1030 of FIG. 10, an apparatus, such as an individual dynamics/kinetics engine 120 or receiver processing and analytics system 110 or 110', may be configured for performing a comparison between tag derived data (including tag location data) and one or more individual dynamics/kinetics models. In some embodiments, a comparison is performed utilizing the associated information.

In one example, the individual dynamics/kinetics engine 120 is configured to determine a multi-dimensional individual location per unit time (e.g., individual location data) for an individual based on the tag location data, the individual role data, and the individual dynamics/kinetics models. Such multi-dimensional individual location may include (1) relative position of the individual relative to a monitored area (e.g., a field of play, race track, etc.) or zone, (2) general orientation of the individual (e.g., standing, squatting, laying the ground, sitting, etc.), and (3) a specific orientation of the individual including the orientation of one or more appendages (e.g., preparing to pass, in a three-point stance, in a ball-carrying position, in a tackling position, negotiating a turn, etc.).

The individual dynamics/kinetics engine 120 uses the real time tag location data stream from the tag data/sensor data filter 112, as well as the individual role data to provide accurate information about what a particular individual is doing in real time. Thus, as shown in block 1040 of FIG. 10, an apparatus, such as an individual dynamics/kinetics engine 120 or receiver processing and analytics system 110 or 110', may be configured for determining one or more probable actions, or optionally non-actions, related to the individual dynamics or movement kinetics of the individual.

As shown in block 1050 of FIG. 10, an apparatus, such as an individual dynamics/kinetics engine 120 or receiver processing and analytics system 110 or 110', may be configured for providing multi-dimensional individual position information per unit time (e.g., individual location data). In one embodiment, the individual dynamics/kinetics engine 120 may be configured for providing one or more probable actions to a HFOP status engine 124. In some embodiments, one or more probable actions are provided in conjunction with the related tag data and associated data.

Health, Fitness, Operation, and Performance Engine Processing

Figure 11:
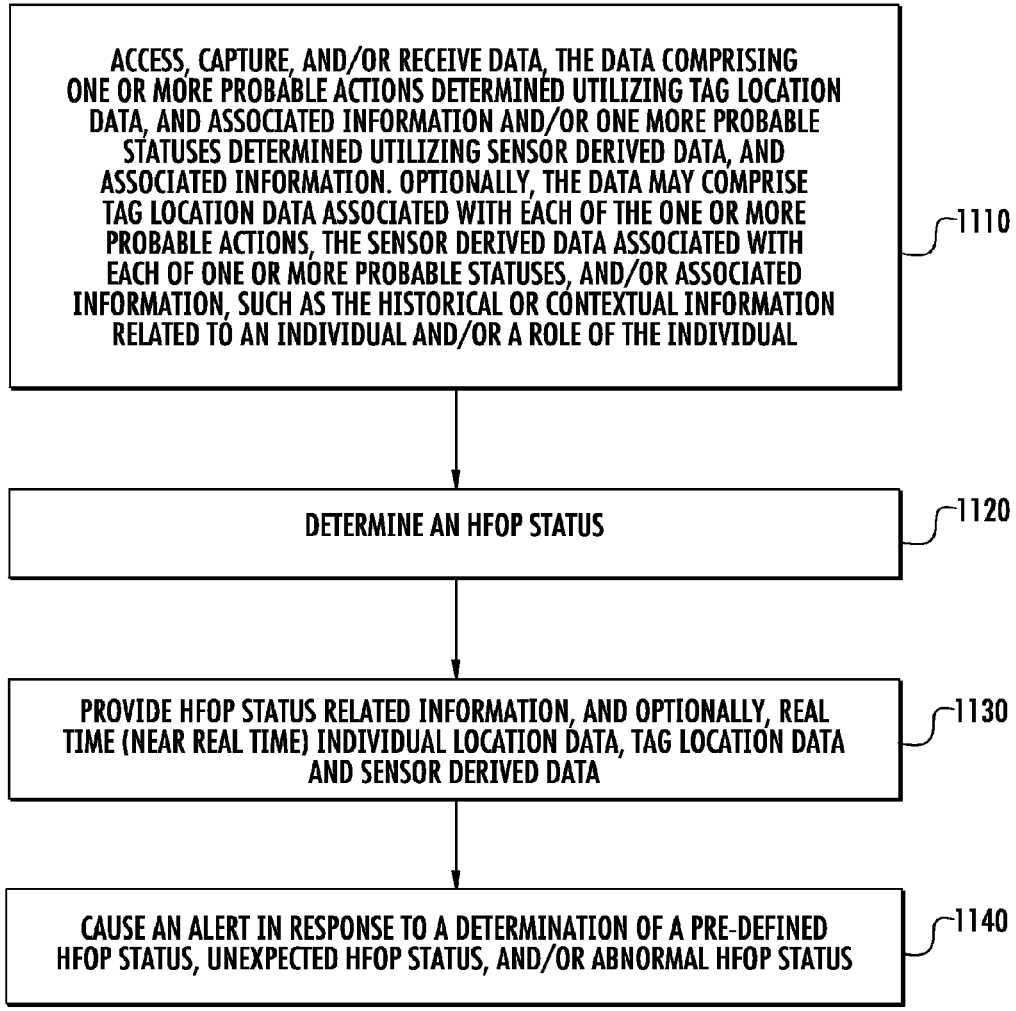
FIG. 11 is a flowchart illustrating a method for use in an health, fitness, operation and performance (HFOP) status engine in accordance with an example embodiment.

FIG. 11 shows an example method that may be executed by one or more machines (some examples of which are discussed in connection with FIGS. 1. 4A, and 4B) to determine a HFOP status of an individual based on tag data and sensor derived data related to the individual, in accordance with some embodiments discussed herein.

As shown in block 1110 of FIG. 11, an apparatus, such as an HFOP status engine 124 or receiver processing and analytics system 110 or 110', may be configured for accessing, capturing, and/or receiving data. In some embodiments, the apparatus may be configured for receiving one or more probable actions and/or multi-dimensional individual location data per unit time determined utilizing tag data, and associated information and/or receiving one or more probable statuses determined utilizing sensor derived data, and associated information. In some embodiments, the apparatus may further be configured for receiving the tag location data (or other tag derived data) associated with each of the one or more probable actions, the sensor derived data associated with each of one or more probable statuses, and/or associated information, such as the historical or contextual information related to an individual and/or a role of the individual. In one embodiment, the one or more statuses are ranked in order of likelihood based on the comparison in the HFOP engine 116.

As shown in block 1120 of FIG. 11, an apparatus, such as an HFOP status engine 124 or receiver processing and analytics system 110 or 110', may be configured for determining an HFOP status.

HFOP status determination may be made utilizing the one or more probable actions and/or the multi-dimensional individual location data per unit time determined by the individual dynamics/kinetics engine 120 utilizing tag data, and associated information and/or the one or more probable statuses determined by the HFOP engine 116 utilizing sensor derived data, and associated information. In some embodiments, HFOP status determination may utilize one or more of the tag location data associated with each of the one or more probable actions, the sensor derived data associated with each of one or more probable statuses, and/or associated information, such as the historical or contextual information related to an individual and/or a role of the individual.

As shown in block 1130 of FIG. 11, an apparatus, such as an HFOP status engine 124 or receiver processing and analytics system 110 or 110', may be configured for providing HFOP status related information. In one embodiment, HFOP status related information may be provided to a processing system for storing and/or displaying real time (or near real time) HFOP status related information. Additionally or alternatively, real time or near real time action data, multi-dimensional location data and/or sensor derived data may be provided for storage or viewing.

In some embodiment, as shown in block 1140 of FIG. 11, an apparatus, such as an HFOP status engine 124 or receiver processing and analytics system 110 or 110', may be configured for causing an alert in response to a determination of a pre-defined HFOP status, unexpected HFOP status, and/or abnormal HFOP status. In one embodiment, the HFOP status engine 124 may be configured for sending a message or HFOP status related information to a parent, trainer, doctor, nurse, paramedic or the like.

Associating Location and Sensor Derived Data to a Specific Individual

In some embodiments, the receiver processing and analytics system 110 or 110' may be configured to send a message or HFOP status related information to a parent, trainer, doctor, nurse, paramedic or the like indicating that help is requested and/or required. The message and/or information may comprise information indicating where the individual is (e.g., the tag location data) and/or the HFOP status. In another embodiment, the message may comprise particular sensor derived data or tag derived data (including tag location data) related to the determined HFOP status.

In one embodiment of the present invention, to utilize a person's medical history in conjunction with tag derived data or sensor derived data to monitor the health and fitness of the person, data received from location tags and/or sensors may be associated with a particular individual. FIG. 12A shows an example method that may be executed by one or more machines (some examples of which are discussed in connection with FIGS. 1, 4A and 4B) to associate data from one or more location tags or sensors with a particular individual, in accordance with some embodiments discussed herein.

As shown in block 1202 of FIG. 12A, an apparatus, such as a receiver processing and analytics system 110, may be configured for accessing, capturing or receiving sensor derived data associated with one or more sensors. In one embodiment, as discussed above, such sensor derived data is received from a receiver hub/locate engine. As shown in block 1204 of FIG. 12, an apparatus, such as a receiver processing and analytics system 110 or 110', may be configured for extracting or determining one or more sensor-individual correlators from the sensor derived data.

As shown in block 1206 of FIG. 12, an apparatus, such as a receiver processing and analytics system 110 or 110', may be configured for looking up or determining individual information (e.g., an individual identifier, individual profile information, individual location models, etc.). As shown in block 1208 of FIG. 12A, an apparatus, such as a receiver processing and analytics system 110 or 110', may be configured for associating the sensor derived data with the individual information.

Figure 12B:
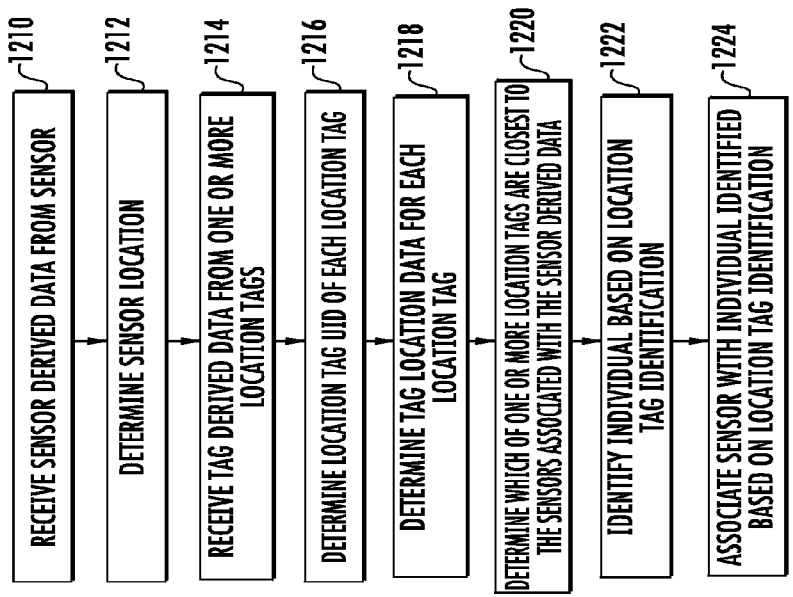
FIGS. 12A-12C are flowcharts showing methods of use in associating sensor data to particular individuals in accordance with an example embodiment.
Figure 12A:
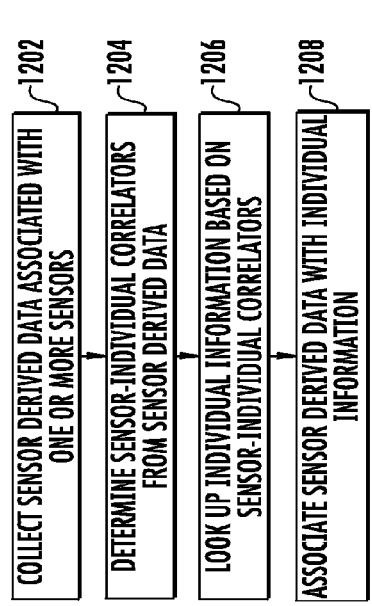

FIG. 12B shows another example method that may be executed by one or more machines (some examples of which are discussed in connection with FIGS. 1, 4A and 4B) to associate sensor derived data from one or more sensors with a particular individual where only an individual and corresponding location tag UID are known in accordance with some embodiments discussed herein.

As shown in block 1210 of FIG. 12, an apparatus, such as a receiver processing and analytics system 110 or 110', may be configured for accessing, capturing or receiving sensor derived data from one or more sensors. As shown in block 1212 of FIG. 12B, an apparatus, such as a receive hub/locate engine 108, may be configured for determining a location of the sensors. For example, in one embodiment, the sensor may be a triangulation positioner that is configured to determine a position calculation. In another embodiment, the sensor may be a proximity label having a position encoded therein. In each of these embodiments, the respective position calculations and position information may be used by the receiver hub/locate engine 108 to determine a location within the monitored area 100. This location is sent from the receiver hub/locate engine 108 and received by the receiver processing and analytics system 110 or 110' as part of the sensor derived data.

As shown in block 1214 of FIG. 12B, an apparatus, such as a receiver processing and analytics system 110 or 110', may be configured for accessing, capturing or receiving tag derived data from one or more location tags. As shown in block 1216 of FIG. 12B, an apparatus, such as a receiver processing and analytics system 110 or 110', may be configured for extracting or determining a location tag UID from the tag derived data captured from one or more location tags.

As shown in block 1218 of FIG. 12B, an apparatus, such as a receiver processing and analytics system 110 or 110', may be configured for extracting or determining tag location data for each of the one or more location tags. As shown in block 1220 of FIG. 12B, an apparatus, such as a receiver processing and analytics system 110 or 110', may be configured for determining which of one or more location tags are most proximately located to the locations of the sensors associated with the sensor derived data.

As shown in block 1222 of FIG. 12B, an apparatus, such as a receiver processing and analytics system 110 or 110', may be configured for identifying an individual associated with location tags (e.g., perhaps based on tag-individual correlators, etc.) determined to be closest to the sensors of interest.

As shown in block 1224 of FIG. 12B, an apparatus, such as a receiver processing and analytics system 110 or 110', may be configured for associating sensor derived data with the individual identified based on his/her association with one or more location tags. For example, sensor derived data having been captured and determined to be captured from a first location is associated with one or more location tags identified as associated with an individual located nearest the first location.

Figure 12C:
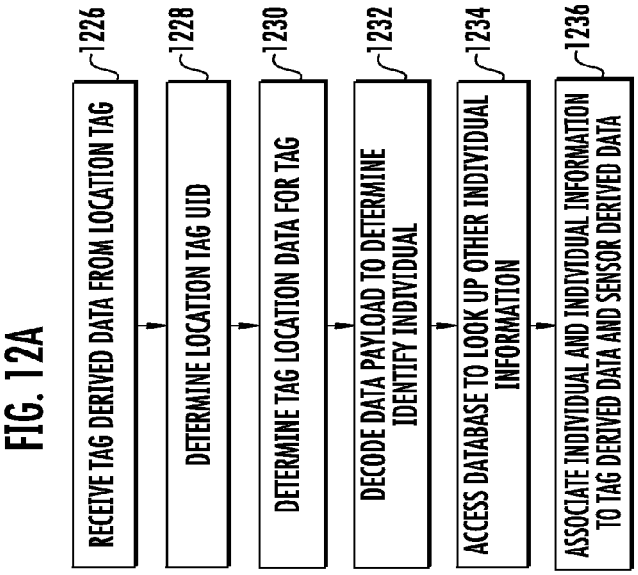

In another embodiment, it may be useful to capture sensor derived data from one or more sensors associated with or near a particular location tag and packetize the data for sending to a receiver, processing system or the like. FIG. 12C shows an example method that may be executed by one or more machines (some examples of which are discussed in connection with FIGS. 1, 4A and 4B) to capture and packetize sensor derived data from one or more sensors, in accordance with some embodiments discussed herein.

As shown in block 1226 of FIG. 12C, an apparatus, such as a receiver processing and analytics system 110 or 110', may be configured for accessing, capturing or receiving data from a receiver. The data may comprise tag derived data and sensor derived data from one or more location tags and one or more sensors, each location tag and/or sensor having a unique identifier (e.g., a tag UID, a sensor UID, etc.). As shown in block 1228 of FIG. 12C, an apparatus, such as a receiver processing and analytics system 110 or 110', may be configured for extracting one or more location tag identifiers from the tag derived data.

As shown in block 1230 of FIG. 12C, an apparatus, such as a receiver hub/locate engine 108, may be configured for determining a location (i.e., tag location data) of the one or more RF location tags from one or more receiver signals. As shown in block 1232 of FIG. 12C, an apparatus, such as a receive hub/locate engine 108 or a receiver processing and analytics system 110 or 110', may be configured for decoding the data payload of the tag derived data and the sensor derived data to determine an individual identity. As shown in block 1234 of FIG. 12C, an apparatus, such as a receive hub/locate engine 108 or a receiver processing and analytics system 110 or 110', may be configured for accessing a database to determine associated information, such as for example individual information associated with the location tags (e.g., perhaps based on tag-individual correlators, tag UIDs identified at block 1232). As shown in block 1236 of FIG. 12C, an apparatus, such as a receive hub/locate engine 108 or a receiver processing and analytics system 110 or 110', may be configured for associating the tag derived data, and the sensor derived data to the associated information, such as the individuals associated with any one or more of the received data.

First Example Embodiment

In one example embodiment, FIG. 13 shows a first individual 1310, a second individual 1320 and an observer 1330 (e.g., a coach). In a situation where the observer 1330 is close enough, and he or she may be able to tell that the first individual 1310 is not ok (e.g., does not satisfy a predetermined HFOP threshold) and the second individual 1320 is ok (e.g., does satisfy a predetermined HFOP threshold) based on the fact that the first individual 1310 is on the ground 1340 and the second individual 1320 is standing. However, in this case, the observer 1330 may have to leave the scene to find help.

In one exemplary embodiment of the present invention, where the first individual 1310 is wearing first location tag 1350 on, for example, their shoulder or chest area, a receiver processing and analytics system 110 or 110' may be configured to utilize tag derived data from the location tag to determine if the first individual 1310 is ok (e.g. not on the ground, unmoving).

In one example embodiment, a comparison of tag derived data from the first location tag 1350 with one or more individual dynamics/kinetics models may determine one or more probable actions. In one embodiment, a HFOP status may be determined based on the comparison. If the determined status exceeds a threshold, and thereby for example, indicates a presence of an abnormality, an alert may be caused. For example, one HFOP model may indicate a falling action if tag location data indicates a person is on the ground.

In another example embodiment, a receiver processing and analytics system 110 or 110' may be configured to utilize tag derived data from the location tag and historical data and/or contextual data to determine if the first individual 1310 is ok. For example, where the first individual 1310 is on the ground for a short period of time, a comparison of tag derived data from the first location tag 1350 in conjunction with historical and/or contextual data may be associated with one or more probable actions, as determined by HFOP or individual dynamics/kinetics models that indicate that there is no problem. However, in some embodiments, when the first individual 1310 is on the ground for a pre-defined period of time, a different HFOP or individual dynamics/kinetics model may be implicated, which may yield a determination of a different action (e.g., injured).

In another example, the first individual may be equipped with two location tags, such as for example, a first location tag 1350, 1350' on their chest or shoulder area and a second location tag 1360, 1360' on their feet area. A receiver processing and analytics system 110 or 110' may be configured to utilize data from the first location tag 1350 and the second location tag 1360 to determine if the first individual 1310 is ok. For example, based on a height or distance between the location tag 1350, 1350' and the second location tag 1360, 1360', the receiver processing and analytics system 110 or 110' may determine that the first individual 1310 is not ok and the second individual 1320 is ok, because for example the height or distance between the first location tag 1350 and the second location tag 1360 on the first individual 1310 is less than a predetermined threshold. Whereas on the second individual 1320, the first location tag 1350' is greater than a predetermined threshold above the second location tag 1360'.

Second Example Embodiment

In one example embodiment of the present invention, historical and contextual data, such as an individual's medical history data, may be utilized in conjunction with location data and sensor derived data to monitor the health and fitness of a person.

Figure 14:
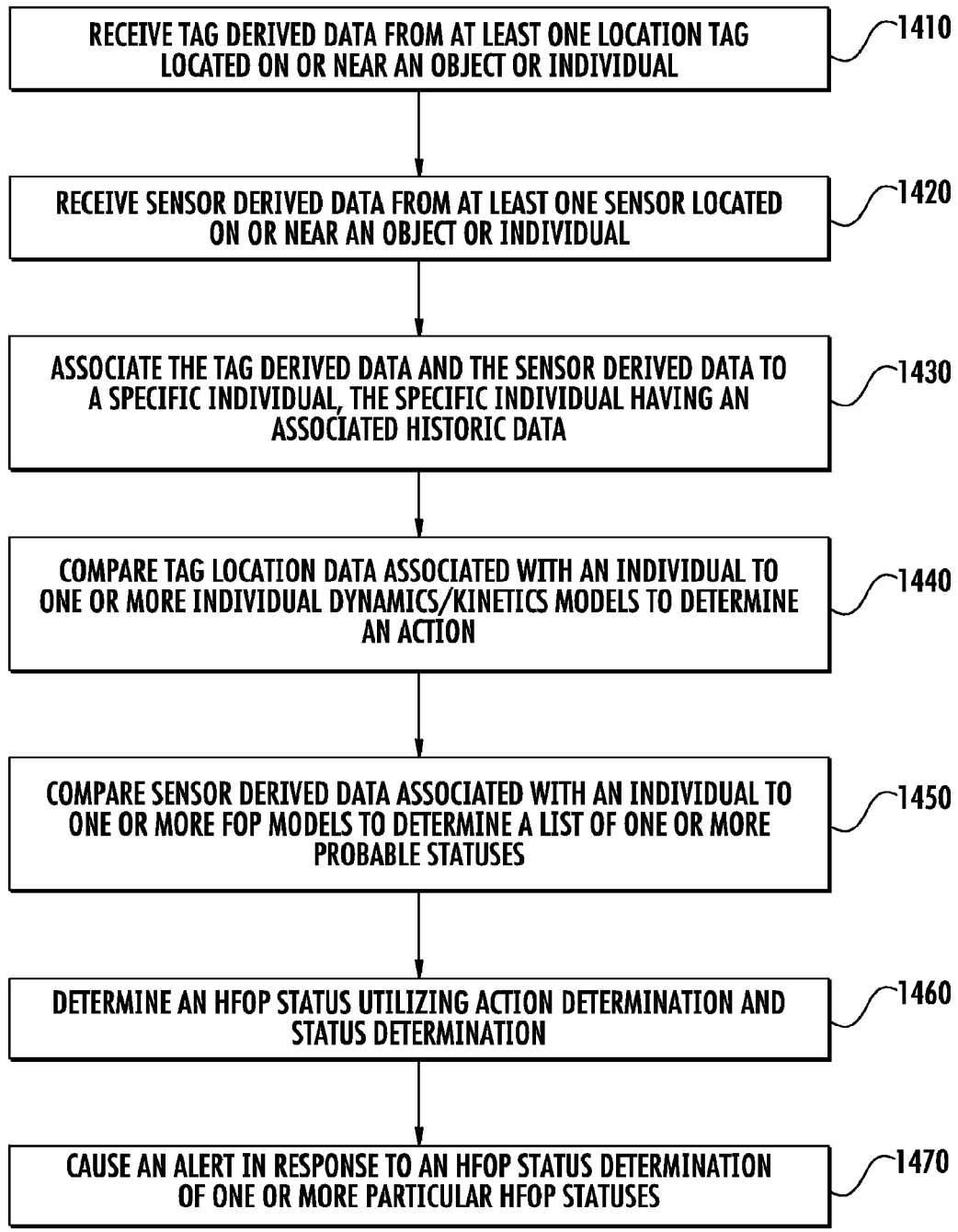
FIG. 14 is a flowchart showing an example embodiment of the monitoring of the health, fitness, operation, or performance of an individual, in accordance with an example embodiment.

FIG. 14 shows an example method that may be executed by one or more machines (some examples of which are discussed in connection with FIGS. 1, 4A and 4B) to monitor the health and fitness of individuals using real time data processing and factoring in associated historical data, in accordance with some embodiments discussed herein.

As shown in block 1410 of FIG. 14, an apparatus, such as receiver processing and analytics system 110 or 110', may be configured for accessing, capturing, and/or receiving tag derived data based on at least one location tag located on or near an object or person.

As shown in block 1420 of FIG. 14, an apparatus, such as receiver processing and analytics system 110 or 110', may be configured for accessing, capturing, and/or receiving sensor derived data based on at least one sensor located on or near an individual such as an object, person or animal.

In one embodiment, where the individual is a human being or an animal, as discussed above, a sensor may be one of a blood pressure sensor for measuring blood pressure, a heart rate sensor for measuring heart rate, a body temperature sensor for measuring body temperature, a microphone (e.g., other sensors configured to determining or representing sounds, etc.) for determining sounds such as speech, whimpers, or screams, a mental response sensor for measuring a mental response time, an eye dilation sensor for measuring dilation of the eyes, and a breathing rate sensor for measuring a breathing rate.

In another embodiment, where the individual is an object such as a car, a sensor may be one of a throttle position sensor, brake position sensor, steering position sensor, axle, wheel or drive shaft sensor, rotary position sensor, crankshaft position sensor, engine coolant temperature sensor, water temperature sensor, oil temperature sensor, fuel gauge sensor, oil gauge sensor, suspension travel sensor, accelerometer, pressure sensor.

In some embodiments, where for example, a human being or an animal is associated with an object, such as a race car, sensors may be provided from both embodiments above, such as for example throttle position sensor, ambient temperature sensor and the like in a race car, and heart rate sensor, sweat rate sensor and the like on the driver.

As shown in block 1430 of FIG. 14, an apparatus, such as receiver processing and analytics system 110 or 110', may be configured for associating the tag derived data from at least one of a location tag and the sensor derived data from the at least one sensor to a specific individual. In some embodiments, this association may be based on tag-individual correlators, sensor-individual correlators, and/or tag-sensor correlators.

The specific individual may have associated historic data, such as for example, health data, medical history data or the like. Medical history data may comprise for example, baseline measurements for one or more of a person's blood pressure, heart rate, mental response, eye dilation, and breathing rate. Associated historical data may comprise, for example, flexibility related data, top speed, acceleration, reaction time or the like.

In one embodiment, associating tag derived data and/or sensor derived data may include capturing an identifier from the data collected from the location tag or sensor and determining a person that is associated with the identifier. However, other methods may be used for associating data from a location tag or sensor with an athlete and may not necessitate a location tag or sensor having an identifier and/or having an athlete pre-associated with that identifier. FIGS. 12A-12C, which are discussed above, are flowcharts showing various example processes for associating an individual with one or more location tags or sensors.

As shown in block 1440 of FIG. 14, an apparatus, such receiver processing and analytics system 110 or 110', may be configured for comparing tag location data associated with an individual, such as multi-dimensional individual location data, to one or more individual dynamics/kinetics models. In one embodiment, associated historic data, contextual data and adversarial data may be utilized.

In one embodiment, an individual (e.g., a football player) may be equipped with a location tag on each foot. A receive processing and analytics system 110 or 110' may be configured to capture and store tag location data from each of the location tags. The receiver processing and analytics system 110 or 110' may further be configured to determine one or more attributes of the individual utilizing the tag location data, for example, gait, a top speed and acceleration. The receiver processing and analytics system 110 or 110' may be configured to then monitor one or more attributes and determine a probable action based on the currently determined attributes (e.g., running top speed during a pass route). The historic information may be utilized in the action determination.

The action determination may repeatedly, over a period of time, indicate a same or similar action for a particular individual when the attribute data does not change or changes at a particular level (e.g., the first individual does not slow down as the game progresses or the first individual slows down 0.2 kilometers per hour each quarter), which may be determined to be expected and/or normal. Thus, a pre-defined output may include output to a user interface (e.g., GUI) or storing to a hard drive.

However, the receiver processing and analytics system 110 or 110' may be configured to calculate, for example, a speed during a pass route, and determine a second action if an abnormality or unexpected calculation occurs. For example, if a current attribute data calculation shows that a wide receiver is slowing down more than a predetermined amount during a pass route, or if a stride length is shorter by a predetermined amount, of if a gait is off by a predetermined amount, the receiver processing and analytics system 110 or 110' may be configured to determine a second action (e.g., sprained ankle, dehydration, torn ACL, or the like).

In another embodiment, a context may be considered. A context may be related to a particular situation, such as a specific sport, a time of day, a weather condition (e.g., temperature, precipitation, humidity or the like), a game circumstance (e.g., no huddle versus huddling by an offense in football, or base running versus playing defense in baseball) or the like.

For example, the receiver processing and analytics system 110 or 110' may be configured to consider or factor in contextual information before or during action determination. In another embodiment, action determination and in particular, sensor based HFOP models and/or individual dynamics/kinetics models are a function of particular contextual information (e.g., top speed in the rain versus top speed in dry conditions).

In one example, if multi-dimensional individual location data of a person running at top speed is determined to show that the individual slowed down quickly and has fallen to the ground, the receiver processing and analytics system 110 or 110' may be configured to consider contextual information before action determination. For example, contextual information may reveal that the person was running on a base path or carrying a ball toward a line of scrimmage just before going to the ground, and thus, an action determination may yield "sliding" or "tackled". However, alternatively, contextual information may reveal that the individual was in open space and no one was around, thus making an action determination based on the slowing down and falling, any one of a number of unexpected or abnormal actions.

In another embodiment, contextual information may include information regarding one or more zones. For example, a location system may be divided into various zones (e.g., a football field and a sideline area). Thus, attribute data which may be cause for alarm in some cases, such as an individual lying down at home plate, may not be cause for alarm in another location, such as an individual lying down in the dugout. In a care providing facility situation, zone division may indicate a bedroom, bathroom, family room couch, vs. garage, kitchen, etc. For example, an individual lying down in a bathroom may yield one action determination, whereas an individual lying down in a bedroom may yield a second action determination.

In another embodiment of the present invention, adversarial data may be considered. Thus, the receiver processing and analytics system 110 or 110' may be configured to consider or factor in adversarial data before or during action determination. In one embodiment, one or more historical attributes related to a first individual may be a function of tag derived data captured from a second individual. For example, depending on whom a second individual is and/or what a second individual is doing, a first individual may act differently, such as running different speeds, turning, cutting, jumping, positioning himself differently or the like, or in the context of race car driving, accelerating, decelerating, taking a different line around a turn or the like. In one embodiment, the receiver processing and analytics system 110 or 110' may be configured to measure and/or calculate relative position information. In another embodiment, relative reaction, speed or acceleration of a first tag (e.g., individual or body part) relative to a second tag (e.g., a second individual or second body part). The receiver processing and analytics system 110 or 110' may be configured to then utilize the relative attribute data in the action determination (e.g., decreasing elbow tag position and hand tag position may lead to an action determination of a broken arm).

In some example embodiments, the receiver processing and analytics system 110 or 110' may further be configured to consider whom or what the second tag is associated with, what a second the individual associated with the second tag position is doing, how the individual associated with the second tag location is performing as contextual information.

As shown in block 1450 of FIG. 14, an apparatus, such as receiver processing and analytics system 110 or 110', may be configured to generate a list of one or more health, fitness, operation, or performance statuses.

In one embodiment, historical data, for example, from a person's medical history, may be used to provide a list of one or more probable statuses of an individual. For example, by knowing an individual's historical heart rate, breathing rate, and/or sweat rate, a combination of sensor derived data may indicate a moderate level of stress and thus one status determination for a first individual. Whereas the same combination of sensor derived data may indicate a high level of stress in a second individual and thus, a second status determination (e.g., panic attack).

In one embodiment, the sensor based HFOP models that are used in status determination may be a function of medical history data. For example, where medical history data shows one or more concussions, particular thresholds and/or tolerances related to sensor derived data may be adjusted such that status determination of a particular status may be more likely and/or is more conservative (e.g., erring on the side of caution). For example, acceptable tolerances in differences in reaction time, eye dilation data or the like may be lowered in individuals who have suffered concussions in their past.

As shown in block 1460 of FIG. 14, an apparatus, such as receiver processing and analytics system 110 or 110', may be configured to utilize an action determination and a status determination to provide a HFOP status determination.

In one embodiment, HFOP status determination may then be compared to one or more pre-defined normal, abnormal or unexpected HFOP statuses. For example, pre-defined abnormal HFOP status may include pulled muscles, broken bones, concussions, or the like. For example, multi-dimensional location data from a person's knees and/or ankles may show a progression of running at top speed, making a quick turn, and slowing down and/or hopping, where one probable HFOP status may be pulling a muscle, which is turn may be identified as an abnormal or unexpected HFOP status.

As shown in block 1470 of FIG. 14, an apparatus, such as receiver processing and analytics system 110 or 110', may be configured for causing an alert in response to an HFOP status determination of one or more particular HFOP statuses.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

As described above and as will be appreciated based on this disclosure, embodiments of the present invention may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Embodiments of the present invention have been described above with reference to block diagrams and flowchart illustrations of methods, apparatuses, systems and computer program products. It will be understood that each block of the circuit diagrams and process flowcharts, and combinations of blocks in the circuit diagrams and process flowcharts, respectively, can be implemented by various means including computer program instructions. These computer program instructions may be loaded onto a general purpose computer, special purpose computer, or other programmable data processing apparatus to produce a machine, such that the computer program product includes the instructions which execute on the computer or other programmable data processing apparatus create a means for implementing the functions specified in the flowchart block or blocks.

These computer program instructions may also be stored in a computer-readable storage device that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions.

Computing Device Architecture

In some embodiments of the present invention, an apparatus, such as a receiver processing and analytics system 110 or 110', tag data/sensor data filter 112, HFOP engine 116, individual dynamics/kinetics engine 120, or HFOP status engine 124 may be embodied by a computing device. The computing device may include or be associated with an apparatus 1500 as shown in FIG. 15. In this regard, the apparatus may include or otherwise be in communication with a processor 1522, a memory device 1524, a communication interface 1526 and a user interface 1528. As such, in some embodiments, although devices or elements are shown as being in communication with each other, hereinafter such devices or elements should be considered to be capable of being embodied within the same device or element and thus, devices or elements shown in communication should be understood to alternatively be portions of the same device or element.

In some embodiments, the processor 1522 (and/or co-processors or any other processing circuitry assisting or otherwise associated with the processor) may be in communication with the memory device 1524 via a bus for passing information among components of the apparatus. The memory device may include, for example, one or more volatile and/or non-volatile memories. In other words, for example, the memory device may be an electronic storage device (e.g., a computer readable storage medium) comprising gates configured to store data (e.g., bits) that may be retrievable by a machine (e.g., a computing device like the processor). The memory device may be configured to store information, data, content, applications, instructions, or the like for enabling the apparatus 1500 to carry out various functions in accordance with an example embodiment of the present invention. For example, the memory device could be configured to buffer input data for processing by the processor. Additionally or alternatively, the memory device could be configured to store instructions for execution by the processor.

As noted above, the apparatus 1500 may be embodied by a computing device 10 configured to employ an example embodiment of the present invention. However, in some embodiments, the apparatus may be embodied as a chip or chip set. In other words, the apparatus may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The apparatus may therefore, in some cases, be configured to implement an embodiment of the present invention on a single chip or as a single "system on a chip." As such, in some cases, a chip or chipset may constitute means for performing one or more operations for providing the functionalities described herein.

The processor 1522 may be embodied in a number of different ways. For example, the processor may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor may include one or more processing cores configured to perform independently. A multi-core processor may enable multiprocessing within a single physical package. Additionally or alternatively, the processor may include one or more processors configured in tandem via the bus to enable independent execution of instructions, pipelining and/or multithreading.

In an example embodiment, the processor 1522 may be configured to execute instructions stored in the memory device 1524 or otherwise accessible to the processor. Alternatively or additionally, the processor may be configured to execute hard coded functionality. As such, whether configured by hardware or software methods, or by a combination thereof, the processor may represent an entity (e.g., physically embodied in circuitry) capable of performing operations according to an embodiment of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform the algorithms and/or operations described herein when the instructions are executed. However, in some cases, the processor may be a processor of a specific device (e.g., a head mounted display) configured to employ an embodiment of the present invention by further configuration of the processor by instructions for performing the algorithms and/or operations described herein. The processor may include, among other things, a clock, an arithmetic logic unit (ALU) and logic gates configured to support operation of the processor. In one embodiment, the processor may also include user interface circuitry configured to control at least some functions of one or more elements of the user interface 1528.

Meanwhile, the communication interface 1526 may be any means such as a device or circuitry embodied in either hardware or a combination of hardware and software that is configured to receive and/or transmit data between the computing device 10 and a server 12. In this regard, the communication interface 1526 may include, for example, an antenna (or multiple antennas) and supporting hardware and/or software for enabling communications wirelessly. Additionally or alternatively, the communication interface may include the circuitry for interacting with the antenna(s) to cause transmission of signals via the antenna(s) or to handle receipt of signals received via the antenna(s). For example, the communications interface may be configured to communicate wirelessly with displays, such as via Wi-Fi, Bluetooth or other wireless communications techniques. In some instances, the communication interface may alternatively or also support wired communication. As such, for example, the communication interface may include a communication modem and/or other hardware/software for supporting communication via cable, digital subscriber line (DSL), universal serial bus (USB) or other mechanisms. For example, the communication interface may be configured to communicate via wired communication with other components of the computing device.

The user interface 1528 may be in communication with the processor 1522, such as the user interface circuitry, to receive an indication of a user input and/or to provide an audible, visual, mechanical, or other output to a user. As such, the user interface may include, for example, a keyboard, a mouse, a joystick, a display, a touch screen display, a microphone, a speaker, and/or other input/output mechanisms. In some embodiments, a display may refer to display on a screen, on a wall, on glasses (e.g., near-eye-display), in the air, etc. The user interface may also be in communication with the memory 1524 and/or the communication interface 1526, such as via a bus.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for associating environmental measurements with an individual, the apparatus comprising a processor and a memory having computer code stored therein, the computer code configured, when executed by the processor, to cause the apparatus to:
   receive blink data and time measurements from a plurality of receivers disposed about a monitored area, wherein the blink data is generated by at least one tag carried by the individual moving about the monitored area, wherein the plurality of receivers are configured to assign the time measurements to the blink data;
   determine tag location data based on the blink data and the time measurements, wherein the tag location data comprises a tag location estimate;
   associate the tag location data with an individual profile;
   receive, from a sensor, a sensor signal comprising one or more environmental measurements indicative of at least one of a health, a fitness, an operation level, or a performance level for the individual;
   receive a sensor location associated with the sensor;
   compare the tag location estimate to the sensor location;
   determine a sensor-individual correlator based on the tag location estimate being within a threshold distance of the sensor location; and
   associate the sensor-individual correlator with the one or more environmental measurements.

2. The apparatus according to claim 1, wherein the blink data comprises a tag-individual correlator, and wherein the associating of the tag location data with the individual profile is based on the tag-individual correlator.

3. The apparatus according to claim 1, wherein the computer code is further configured, when executed by the processor, to cause the apparatus to receive a tag-individual correlator from an individual database, and wherein the associate the tag location data with the individual profile is based on the tag-individual correlator.

4. The apparatus according to claim 1, wherein the computer code is further configured, when executed by the processor, to cause the apparatus to:
receive second blink data from the plurality of receivers disposed about the monitored area, wherein the second blink data is generated by the at least one tag carried by the individual moving about the monitored area;
determine second tag location data based on the second blink data, wherein the second tag location data comprises a second tag location estimate;
associate the second tag location data with the individual profile;
receive, from a second sensor, a second sensor signal comprising one or more second environmental measurements indicative of at least one of a second health, a second fitness, a second operation level, or a second performance level for the individual;
receive a second sensor location associated with the second sensor, wherein the second sensor location is different than the sensor location;
compare the second tag location estimate to the second sensor location;
determine a second sensor-individual correlator based on the second tag location estimate being within a threshold distance of the second sensor location; and
associate the second sensor-individual correlator with the one or more second environmental measurements.

5. The apparatus according to claim 1, wherein the computer code is further configured, when executed by the processor, to cause the apparatus to:
determine a health, fitness, operation, or performance (HFOP) status for the individual based both on the environmental measurements and on the tag location data.

6. The apparatus according to claim 1, wherein the computer code is further configured, when executed by the processor, to cause the apparatus to:
receive second blink data from the plurality of receivers disposed about the monitored area, wherein the second blink data is generated by a second tag mounted proximate the sensor within the monitored area;
determine second tag location data based on the second blink data, wherein the second tag location data comprises a sensor location estimate; and
determine the sensor location based on the sensor location estimate.

7. The apparatus according to claim 1, wherein the computer code is further configured, when executed by the processor, to cause the apparatus to:
receive position calculations from a triangulation positioner mounted proximate the sensor within the monitored area; and
determine the sensor location based on the position calculations.

8. A computer program product for associating environmental measurements with an individual comprising at least one non-transitory computer-readable storage medium having computer-executable program code instructions stored therein, the computer-executable program code instructions comprising program code instructions for:
receiving blink data and time measurements from a plurality of receivers disposed about a monitored area, wherein the blink data is generated by at least one tag carried by the individual moving about the monitored area, wherein the plurality of receivers are configured to assign the time measurements to the blink data;
determining tag location data based on the blink data and the time measurements, wherein the tag location data comprises a tag location estimate;
associating the tag location data with an individual profile;
receiving, from a sensor, a sensor signal comprising one or more environmental measurements indicative of at least one of a health, a fitness, an operation level, or a performance level for the individual;
receiving a sensor location associated with the sensor;
comparing the tag location estimate to the sensor location;
determining a sensor-individual correlator based on the tag location estimate being within a threshold distance of the sensor location; and
associating the sensor-individual correlator with the one or more environmental measurements.

9. The computer program product according to claim 8, wherein the blink data comprises a tag-individual correlator, and wherein the associating of the tag location data with the individual profile is based on the tag-individual correlator.

10. The computer program product according to claim 8, wherein the computer-executable program code instructions further comprise program code instructions for receiving a tag-individual correlator from an individual database, and wherein the associating the tag location data with the individual profile is based on the tag-individual correlator.

11. The computer program product according to claim 8, wherein the computer-executable program code instructions further comprise program code instructions for:
receiving second blink data from the plurality of receivers disposed about the monitored area, wherein the second blink data is generated by the at least one tag carried by the individual moving about the monitored area;
determining second tag location data based on the second blink data, wherein the second tag location data comprises a second tag location estimate;
associating the second tag location data with the individual profile;
receiving, from a second sensor, a second sensor signal comprising one or more second environmental measurements indicative of at least one of a second health, a second fitness, a second operation level, or a second performance level for the individual;
receiving a second sensor location associated with the second sensor, wherein the second sensor location is different than the sensor location;
comparing the second tag location estimate to the second sensor location;
determining a second sensor-individual correlator based on the second tag location estimate being within a threshold distance of the second sensor location; and
associating the second sensor-individual correlator with the one or more second environmental measurements.

12. The computer program product according to claim 8, wherein the computer-executable program code instructions further comprise program code instructions for:
determining a health, fitness, operation, or performance (HFOP) status for the individual based both on the environmental measurements and on the tag location data.

13. The computer program product according to claim 8, wherein the computer-executable program code instructions further comprise program code instructions for:
receiving second blink data from the plurality of receivers disposed about the monitored area, wherein the second blink data is generated by a second tag mounted proximate the sensor within the monitored area;

determining second tag location data based on the second blink data, wherein the second tag location data comprises a sensor location estimate; and determining the sensor location based on the sensor location estimate.

14. The computer program product according to claim 8, wherein the computer-executable program code instructions further comprise program code instructions for:

receiving position calculations from a triangulation positioner mounted proximate the sensor within the monitored area; and determining the sensor location based on the position calculations.

15. A system for associating environmental measurements with an individual moving about a monitored area, the system comprising:

at least one tag carried by the individual, wherein the at least one tag is configured to generate blink data;

a plurality of receivers disposed about the monitored area, wherein the plurality of receivers are configured to assign time measurements to the blink data;

a receiver/hub locate engine, the receiver/hub locate engine comprising a processor and a memory having computer code stored therein, the computer code configured, when executed by the processor, to cause the receiver/hub locate engine to:

receive the blink data and the time measurements from the plurality of receivers;

determine tag location data based on the blink data and the time measurements, wherein the tag location data comprises a tag location estimate;

associate the tag location data with an individual profile;

receive, from a sensor, a sensor signal comprising one or more environmental measurements indicative of at least one of a health, a fitness, an operation level, or a performance level for the individual;

receive a sensor location associated with the sensor;

compare the tag location estimate to the sensor location;

determine a sensor-individual correlator based on the tag location estimate being within a threshold distance of the sensor location; and associate the sensor-individual correlator with the one or more environmental measurements.

16. The system according to claim 15, wherein the blink data comprises a tag-individual correlator, and wherein the associate the tag location data with the individual profile is based on the tag-individual correlator.

17. The system according to claim 15, wherein the computer code is further configured, when executed by the processor, to cause the receiver/hub to receive a tag-individual correlator from an individual database, and wherein the associating of the tag location data with the individual profile is based on the tag-individual correlator.

18. The system according to claim 15, wherein the computer code is further configured, when executed by the processor, to cause the receiver/hub to:

receive second blink data from the plurality of receivers disposed about the monitored area, wherein the second blink data is generated by the at least one tag carried by the individual;

determine second tag location data based on the second blink data, wherein the second tag location data comprises a second tag location estimate;

associate the second tag location data with the individual profile;

receive, from a second sensor, a second sensor signal comprising one or more second environmental measurements indicative of at least one of a second health, a second fitness, a second operation level, or a second performance level for the individual;

receive a second sensor location associated with the second sensor, wherein the second sensor location is different than the second location;

compare the second tag location estimate to the second sensor location;

determine a second sensor-individual correlator based on the second tag location estimate being within a threshold distance of the sensor location; and associate the second sensor-individual correlator with the one or more second environmental measurements.

19. The system according to claim 15, wherein the computer code is further configured, when executed by the processor, to cause the receiver/hub to:

determine a health, fitness, operation, or performance (HFOP) status for the individual based both on the environmental measurements and on the tag location data.

20. The system according to claim 15, wherein the computer code is further configured, when executed by the processor, to cause the receiver/hub to:

receive second blink data from the plurality of receivers disposed about the monitored area, wherein the second blink data is generated by a second tag mounted proximate the sensor within the monitored area;

determine second tag location data based on the second blink data, wherein the second tag location data comprises a sensor location estimate; and determine the sensor location based on the sensor location estimate.

21. The system according to claim 15, wherein the computer code is further configured, when executed by the processor, to cause the receiver/hub to:

receive position calculations from a triangulation positioner mounted proximate the sensor within the monitored area; and determine the sensor location based on the position calculations.

\* \* \* \* \*